(12) United States Patent
Notni et al.

(10) Patent No.: US 9,260,483 B2
(45) Date of Patent: Feb. 16, 2016

(54) TRIAZACYCLONONANE-BASED PHOSPHINATE LIGAND AND ITS USE FOR MOLECULAR IMAGING

(75) Inventors: Johannes Notni, Hohenbrunn (DE); Hans-Jürgen Wester, Ilmmünster (DE)

(73) Assignee: TECHNISCHE UNIVERSITÄT MÜNCHEN, München (DE)

( * ) Notice: Subject to any disclaimer, the term of this patent is extended or adjusted under 35 U.S.C. 154(b) by 76 days.

(21) Appl. No.: 13/978,859

(22) PCT Filed: Jan. 5, 2012

(86) PCT No.: PCT/EP2012/050123
§ 371 (c)(1),
(2), (4) Date: Oct. 7, 2013

(87) PCT Pub. No.: WO2012/095347
PCT Pub. Date: Jul. 19, 2012

(65) Prior Publication Data
US 2014/0030820 A1    Jan. 30, 2014

Related U.S. Application Data

(60) Provisional application No. 61/460,954, filed on Jan. 10, 2011.

(30) Foreign Application Priority Data

Jan. 10, 2011 (EP) ..................... 11150496

(51) Int. Cl.
*A61K 51/00* (2006.01)
*A61M 36/14* (2006.01)
*C07K 7/64* (2006.01)
*G01N 21/75* (2006.01)
*C07F 9/6515* (2006.01)
*C07F 9/6558* (2006.01)
*A61K 51/04* (2006.01)

(52) U.S. Cl.
CPC ............... *C07K 7/64* (2013.01); *C07F 9/6515* (2013.01); *C07F 9/65583* (2013.01); *C07F 9/65586* (2013.01); *G01N 21/75* (2013.01); *A61K 51/0482* (2013.01)

(58) Field of Classification Search
CPC ................................ A61K 51/0482
See application file for complete search history.

(56) References Cited

PUBLICATIONS

Notni et al., "A Triazacyclononane-Based Bifunctional Phosphinate Ligand for the Preparation of Multimeric 68Ga Tracers for Positron Emission Tomography," Chemistry A European Journal, vol. 16, 2010, pp. 7174-7185.
Schottelius et al., "Rapid and high-yield solution-phase synthesis of DOTA-Tyr3-octreotide and DOTA-Tyr3-octreotate using unprotected DOTA," Tetrahedron Letters, vol. 44, 2003, pp. 2393-2396.

*Primary Examiner* — Michael G Hartley
*Assistant Examiner* — Melissa Perreira
(74) *Attorney, Agent, or Firm* — Birch, Stewart, Kolasch & Birch, LLP

(57) ABSTRACT

The present invention relates to the field of molecular imaging, i.e. nuclear and fluorescent imaging using metal ion radionuclides in combination with chelates highly functionalized with peptidic, nonpeptidic or protein ligands or additional signalling moieties.

6 Claims, 8 Drawing Sheets

Figure 3.
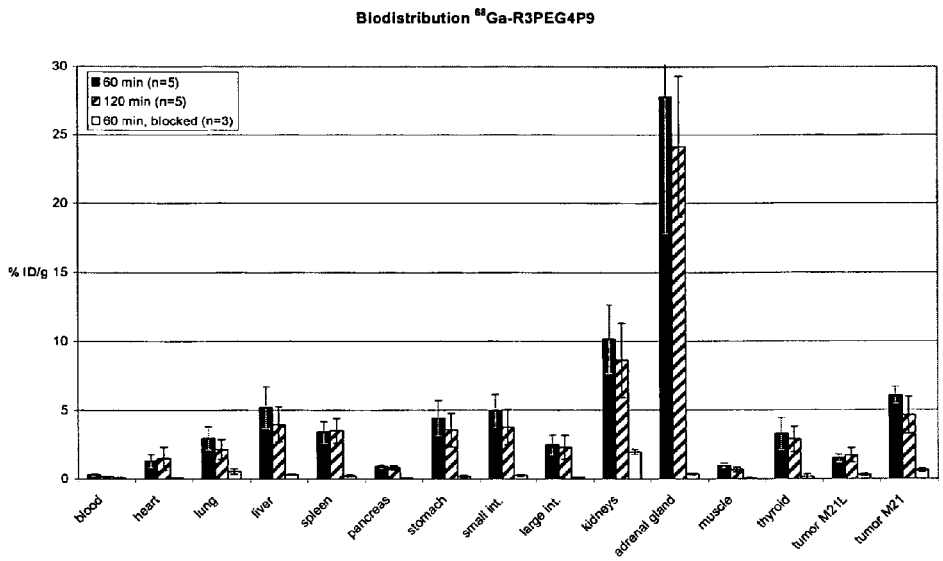
Figure 4a- $^{68}$Ga-R3PEG4P9 tracer after synthesis.
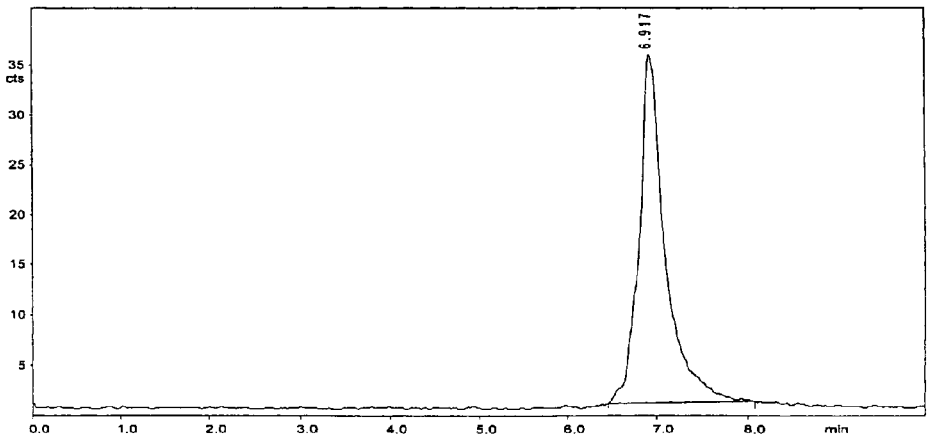

Figure 4b -Urine.
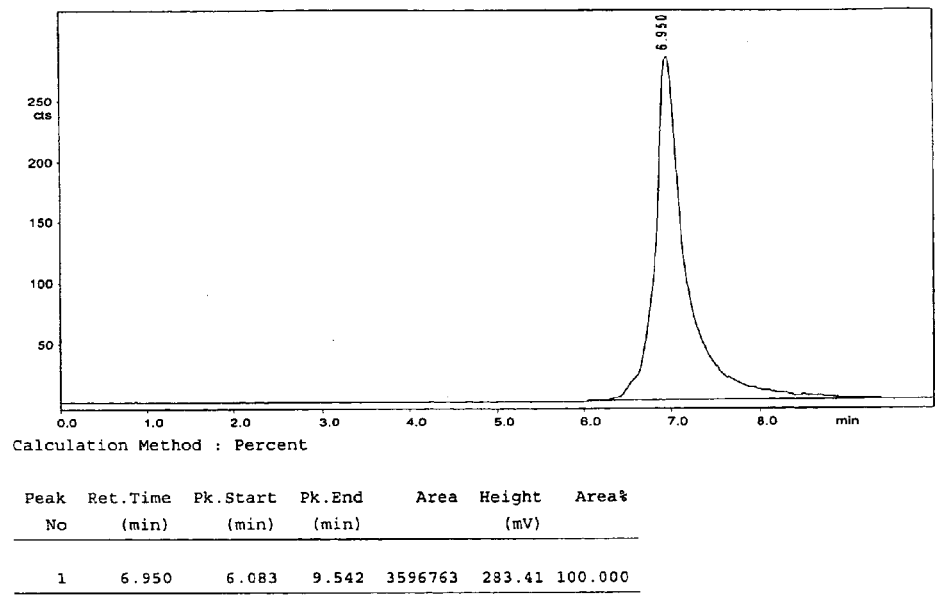
Figure 4c-Blood plasma.
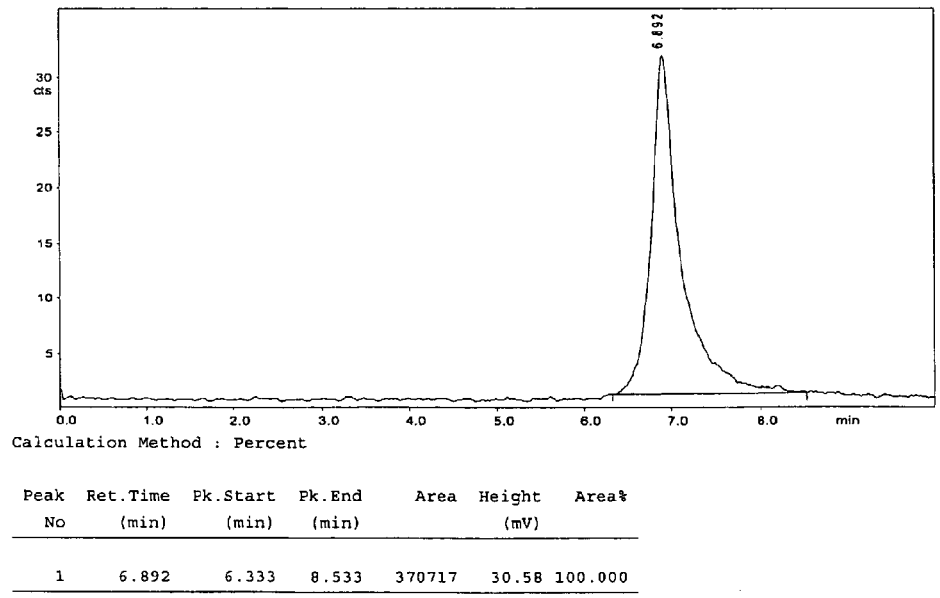

Figure 4d- Kidney.
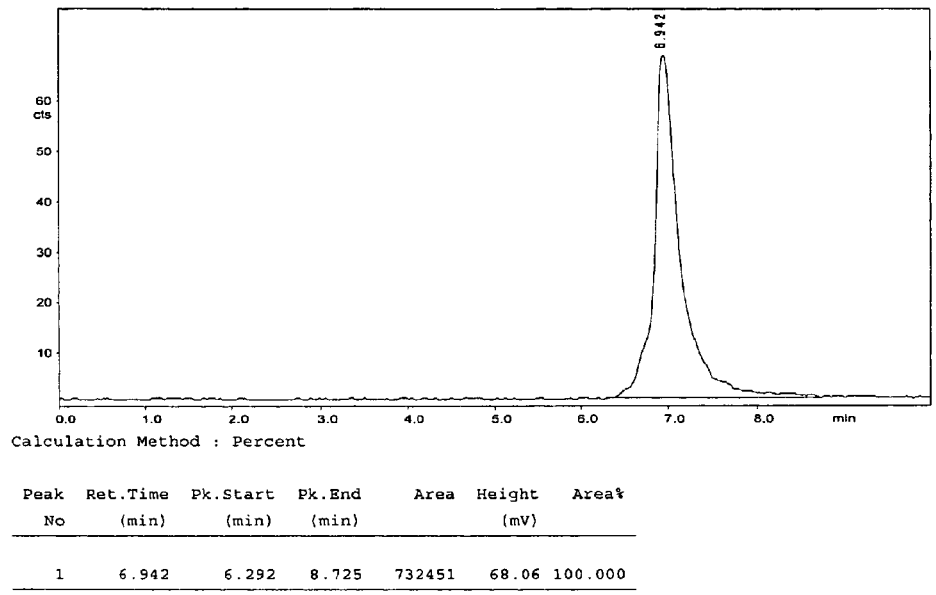
Calculation Method : Percent
| Peak No | Ret.Time (min) | Pk.Start (min) | Pk.End (min) | Area | Height (mV) | Area% |
|---|---|---|---|---|---|---|
| 1 | 6.942 | 6.292 | 8.725 | 732451 | 68.06 | 100.000 |
Figure 4e- Liver.
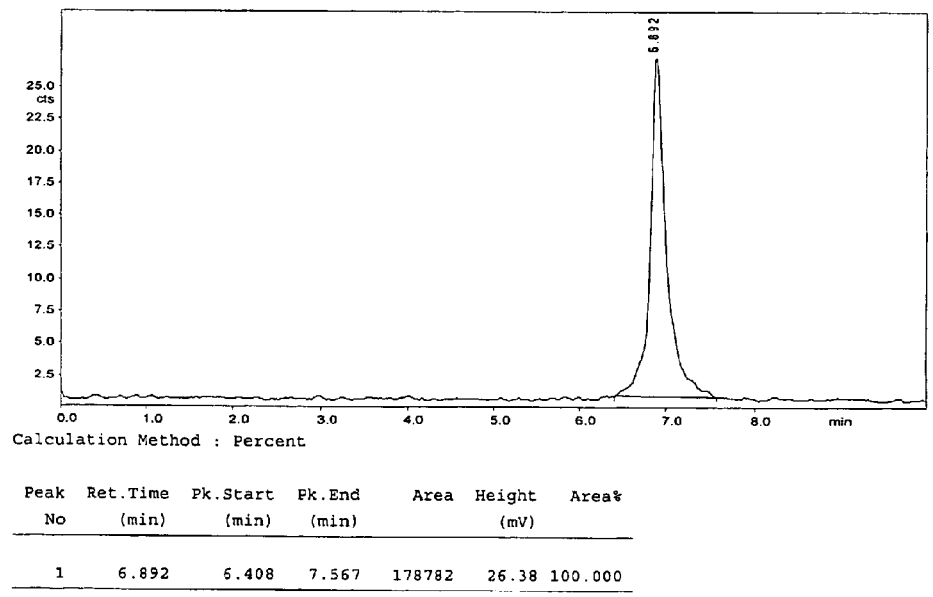
Calculation Method : Percent
| Peak No | Ret.Time (min) | Pk.Start (min) | Pk.End (min) | Area | Height (mV) | Area% |
|---|---|---|---|---|---|---|
| 1 | 6.892 | 6.408 | 7.567 | 178782 | 26.38 | 100.000 |

Figure 4f- Spleen / pancreas.
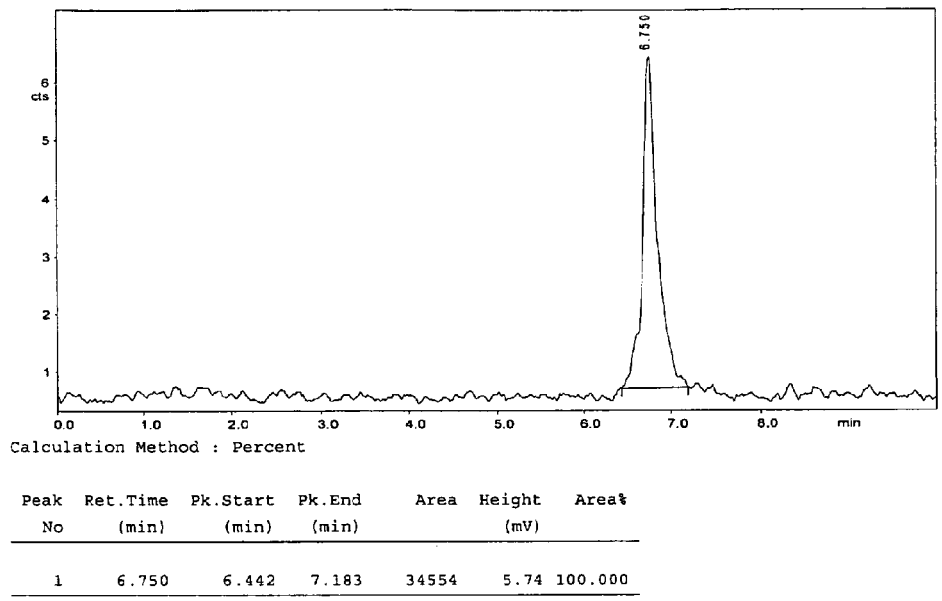
Figure 4g- Adrenal gland.
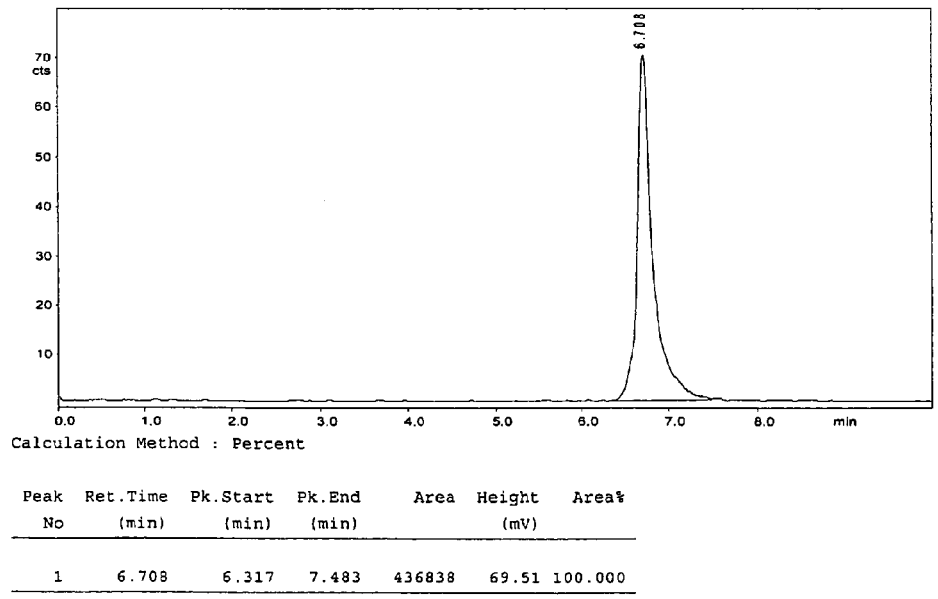

Figure 4h- Tumor M21.
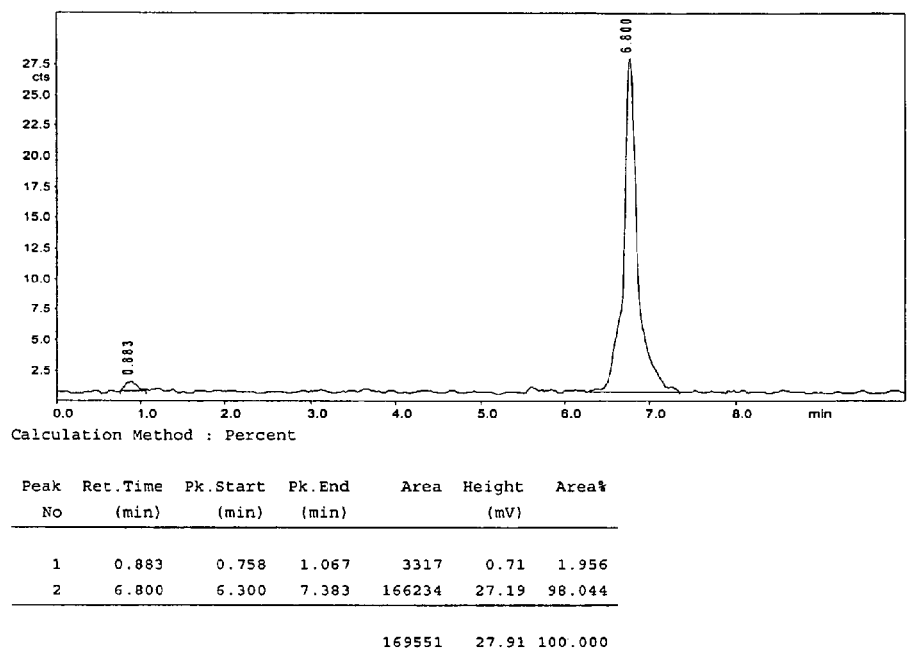
Figure 5.
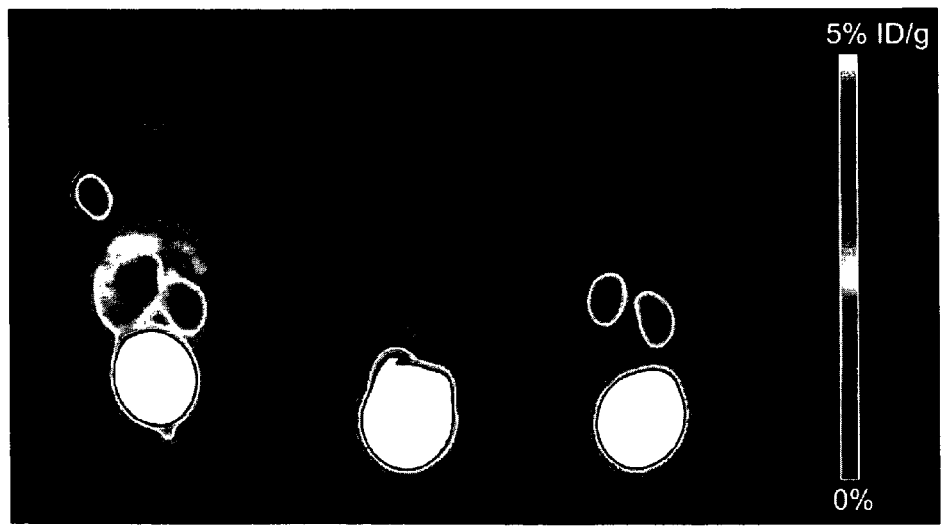

Figure 6a- $^{68}$Ga-R3PEG4P9.
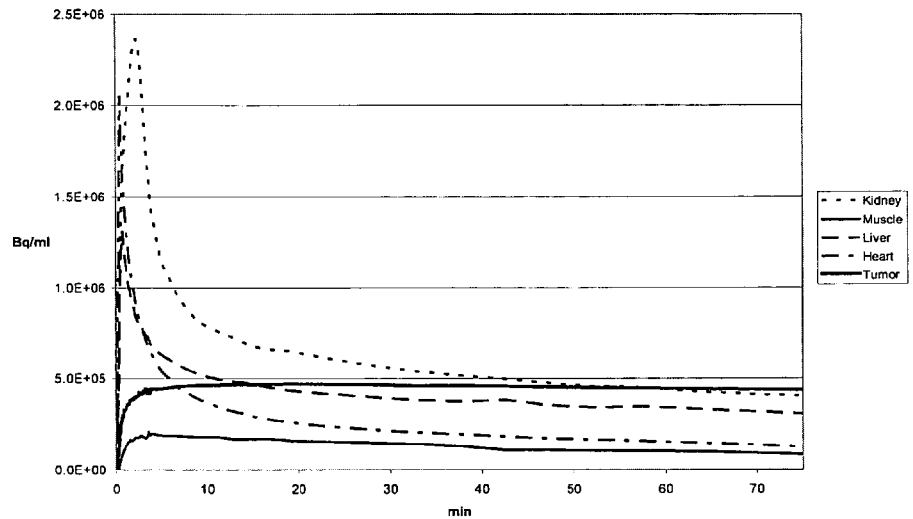
Figure 6b- $^{68}$Ga-R3PEG4P9, blockade with 100 µg unlabelled R3PEG4P9.
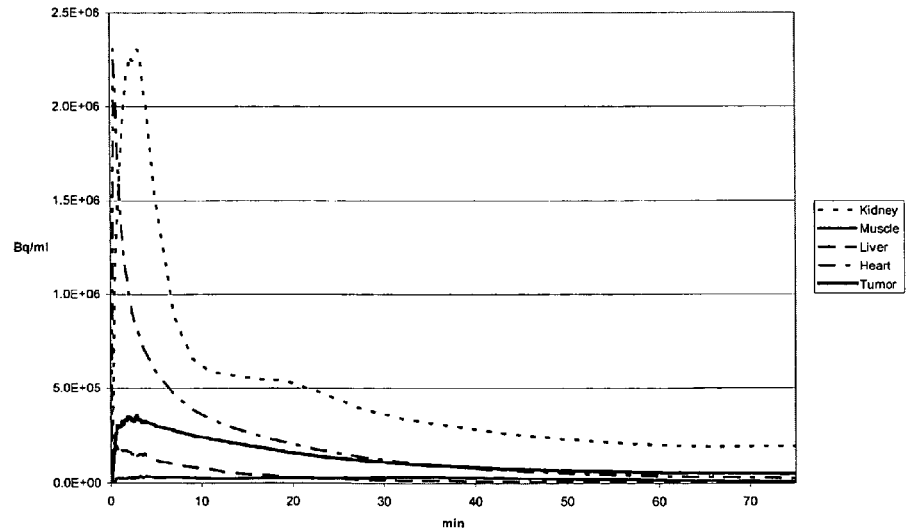

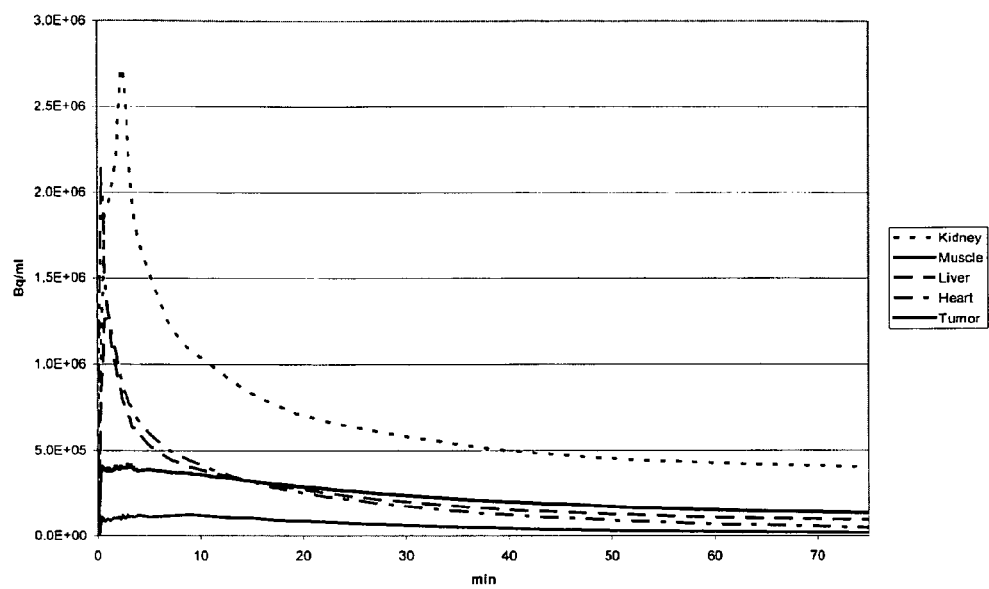
Figure 6c- $^{68}$Ga-isoR3PEG4P9 (inverse sequence non-binding peptide conjugate).

TRIAZACYCLONONANE-BASED PHOSPHINATE LIGAND AND ITS USE FOR MOLECULAR IMAGING

CROSS-REFERENCE TO RELATED APPLICATIONS

This application is the National Phase of PCT/EP2012/050123 filed on Jan. 5, 2012, which claims priority under 35 U.S.C. 119(e) to U.S. Provisional Application No. 61/460,954 filed on Jan. 10, 2011 and under 35 U.S.C. 119(a) to patent application Ser. No. 11/150,496.5 filed in Europe on Jan. 10, 2011, all of which are hereby expressly incorporated by reference into the present application.

TECHNICAL FIELD

The present invention relates to the field of molecular imaging, i.e. nuclear and fluorescent imaging using metal ion radionuclides in combination with chelates highly functionalized with peptidic, nonpeptidic or protein ligands or additional signalling moieties.

BACKGROUND ART

Metal radionuclides are frequently used in nuclear imaging and therapy. Fluorescently labelled ligands are commonly used for optical imaging in animal models or in vivo imaging during i.e. surgical interventions. Related tracers are usually formed from a metal binding group (chelate ligand) or fluorescent units and moieties, which are bound, with or without linkers, to one or more targeting vectors.

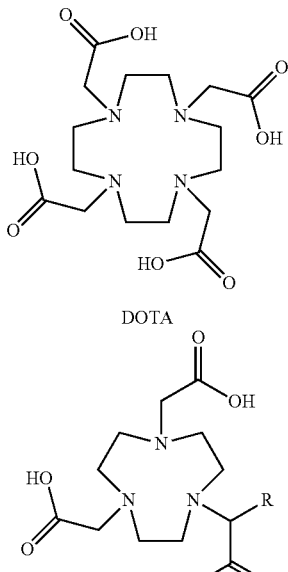

DOTA

NOTA: R = H
NODAGA: R = CH$_2$—CH$_2$—COOH

Currently, DOTA (1,4,7,10-tetraazacyclododecane-1,4,7,10-tetraacetic acid) is the most frequently used compound for the purpose of nuclear imaging with radiometals. It forms stable complexes with many transition metal ions as well as lanthanide ions. Very frequently, one of the acetic acid side arms of this molecule is used to for conjugation of DOTA to the targeting vector resulting in the formation of an amide. For imaging purposes, the metal ion is finally added in the last step, thereby forming the complex which serves as the tracer or radiopharmaceutical. Particularly for complexation of lanthanide ions, the most established chelators are DOTA and derivatives of this structure, such as 1,4,7,10-tetraazacyclododecane-1,4,7-triacetic acid (DO3A). For smaller metal ions such as Ga(III), bifunctional chelators based on the 1,4,7-triaza-1,4,7-triacetic acid (NOTA) structural motif, such as NODAGA (1,4,7-triaza-1-glutaric acid-4,7-diacetic acid), have recently gained popularity because the resulting complexes are more thermodynamically stable and are formed more easily.

All of these chelators bind the radioactive metal ion by coordination on the nitrogen atoms of the azamacrocycle backbone and on the deprotonated carboxyl groups of the acetic acid substituents. These carboxylic acid moieties thus have to be deprotonated in order to act as coordination sites, which is why a pH value exceeding their $pK_a$ of approx. 3.5-4.5 must be maintained during the labelling procedure. Labelling at a lower pH is substantially hampered. In case of the radionuclide $^{68}$Ga(III) this is somewhat contradictory due to the fact that at pH>3, formation of colloidal Ga(OH)$_3$ commences which is also inhibiting the complex formation. For labelling of all iminopolyacetic acid ligands, like the above mentioned ones, a careful adjustment of pH value to 3-3.5 is thus mandatory. In addition, labelling of DOTA-like structures requires either heating, usually up to 80-95° C., or comparably high ligand concentrations, in the range of for example 1 mM.

In order to prepare bioconjugates of chelators, that is, molecules consisting of a targeting vector covalently bound to a chelating unit, the use of protecting groups on either side is mandatory in most cases according to the prior art. Particularly in case of DOTA or DO3A, the carboxylate moieties intended for metal complexation are often protected during amide coupling, see for example Schottelius M, Schwaiger M, Wester H J. Rapid and high-yield solution phase synthesis of DOTA-Tyr$^3$-octreotide and DOTA-Tyr$^3$-octreotate using unprotected DOTA. Tetrahedron Lett. 2003, 44 (11), 2393-2396. Tris-tert-butyl esters of these compounds are thus employed for conjugation. In most cases, an additional subsequent deprotection step is necessary in order to obtain the desired fully deprotected bioconjugate.

In the context of bioconjugates, the term multimer refers to molecules which comprise more than one targeting vector of the same kind. Multimers are desirable because in comparison to monomers, they can exhibit increased affinity to the respective target, thus often resulting in higher target uptake, higher target/background ratios, and thus better images. For preparation of multimeric radiometal tracers, DOTA-like chelators are usually bound to a linker which allows more than one targeting vector to be bound. The assembly of such molecules usually involves multistep syntheses with low overall yield. In addition and especially in the case of Ga-68 labelled peptides, two carboxylic groups of DOTA have been used for the formation of dimers by amide formation.

Combination of more than one imaging modality is usually referred to as multimodal imaging. Imaging technologies that can be combined include positron emission tomography (PET), single photon emission computed tomography (SPECT), planar scintigraphy, fluorescence imaging, magnet resonance tomography (MRT), optical imaging (either fluorescence or bioluminescence imaging) and combinations thereof, i.e. PET/CT and PET/MRT. To perform multimodal imaging, tracers are required possessing more than one reporter unit, e.g. combining the presence of a chelate unit for radiometals (for e.g. PET) with a so called fluorophor (for fluorescence). For such an approach, the presence of targeting vectors in the same molecule is, however not mandatory, still necessary for functional imaging.

Recently, a novel chelating unit based on 1,4,7-triazacyclononane, PrP9 (I), has been introduced, see for example Notni J., Hermann P., Havlickova J., Kotek J., Kubicek V., Plutnar J., Loktionova N., Riss P. J., Rosch F., Lukes I., A Triazacyclononane-Based Bifunctional Phosphinate Ligand for the Preparation of Multimeric Ga-68 Tracers for Positron Emission Tomography. Chemistry—A European Journal. 2010; 16(24):7174-7185.

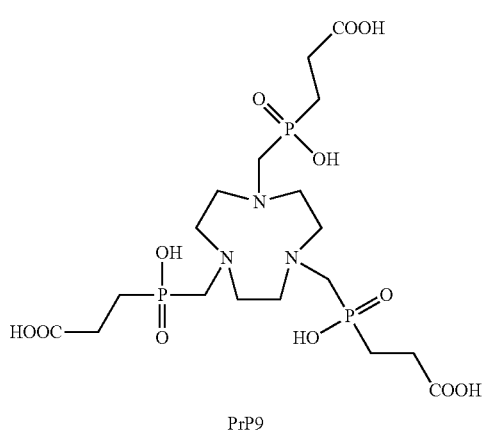

PrP9

(I)

3PrP9 (I) is particularly suitable for complexation of smaller radiometal ions, such as $^{68}Ga^{3+}$. In contrast to the above mentioned chelators bearing carboxylates, phosphinic acid moieties exhibit pKa values below 1. Thus, labelling can be performed at pH<2, thus circumventing formation of colloids.

AIMS OF THE INVENTION

The invention aims at chelate ligands for radiometals, which are equipped with biomolecules, such as cyclic peptides, to be used for molecular imaging and/or therapy.

In addition, the invention aims at said chelate ligands, bearing additional reporter units for other imaging modalities such as fluorescence imaging.

The invention further aims at the fast and high yield radiolabelling of the aforementioned chelators and their derivatives with radiometals, preferably with $^{68}Ga$, particularly preferably with $^{68}Ga^{3+}$, at very low chelator concentrations in the reaction mixture, resulting in radiopharmaceuticals with exceptionally high specific activity.

Another aim of the invention is the application of said radiopharmaceuticals for nuclear and fluorescence imaging purposes.

DISCLOSURE OF THE INVENTION

The inventors of the present invention have found that chelate ligands which are based on amide-functionalized 1,4,7-triazacyclononane-1,4,7-tris[methyl(2-carboxyethyl) phosphinic acid](II)

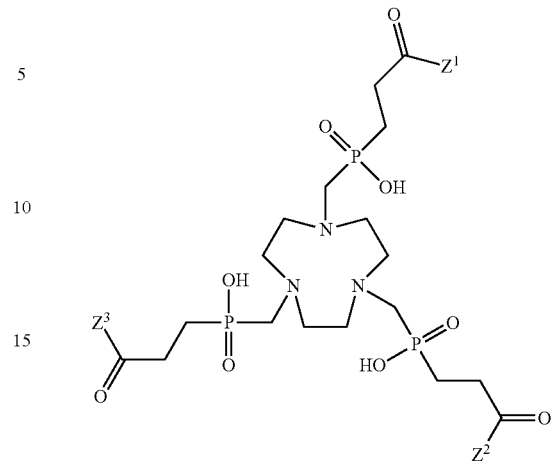

(II)

give rise to corresponding nuclear chelates which may advantageously used for molecular imaging and/or therapy, bearing additional reporter units for other imaging modalities such as fluorescence imaging. In addition the chelate ligands according to the present invention make fast and high yield radiolabelling of the aforementioned chelators and their derivatives with radiometals, preferably with $^{68}Ga$, particularly preferably with $^{68}Ga^{3+}$, at very low chelator concentrations in the reaction mixture, possible. These circumstances result in radiopharmaceuticals with exceptionally high specific activity.

The present invention therefore relates to chelate ligands according to general formula (II)

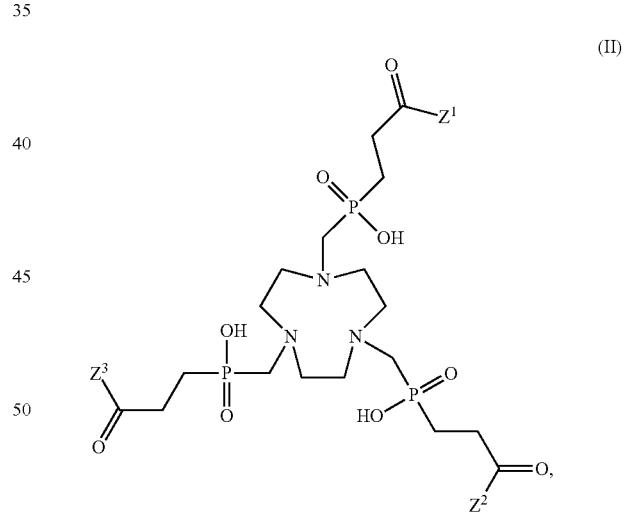

(II)

wherein
$Z^1$ is OH or $NR^1R^4$,
$Z^2$ is OH or $NR^2R^5$,
$Z^3$ is OH or $NR^3R^6$,
$R^1$, $R^2$, $R^3$ is independently of another selected from the group consisting of linear or cyclic, substituted or unsubstituted, aliphatic, heteroaliphatic, aromatic, heteroaromatic, saturated or unsaturated radicals, wherein said $R^1$, $R^2$ and/or $R^3$ is optionally attached to the core molecule via at least one linking group,
$R^4$, $R^5$, $R^6$ is independently of another selected from the group consisting of hydrogen, linear or cyclic, substituted or unsubstituted, aliphatic, heteroaliphatic, aromatic, heteroaromatic, saturated or unsaturated radicals,
wherein at least one of $Z^1$, $Z^2$ and $Z^3$ is different from OH.

In a preferred embodiment $Z^1$, $Z^2$ and $Z^3$ are different from OH, meaning that $Z^1$ is $NR^1R^4$, $Z^2$ is $NR^2R^5$ and $Z^3$ is $NR^3R^6$.

In another embodiment of the present invention two of $Z^1$, $Z^2$ and $Z^3$ are different from OH, meaning that $Z^1$ is $NR^1R^4$ and $Z^2$ is $NR^2R^5$ and $Z^3$ is OH, or $Z^1$ is $NR^1R^4$ and $Z^2$ is OH and $Z^3$ is $NR^3R^6$, or $Z^1$ is OH and $Z^2$ is $NR^2R^5$ and $Z^3$ is $NR^3R^6$.

In another embodiment of the present invention one of $Z^1$, $Z^2$ and $Z^3$ is different from OH, meaning that $Z^1$ is $NR^1R^4$ and $Z^2$ is OH and $Z^3$ is OH, or $Z^1$ is OH and $Z^2$ is $NR^2R^5$ and $Z^3$ is OH, or $Z^1$ is OH and $Z^2$ is OH and $Z^3$ is $NR^3R^6$.

According to the present invention, the core molecule is PrP9 according to formula (I). Compounds according to general formula (II) are in general obtained by reaction of compound of general formula (I) and amines $R^1R^4NH$, $R^2R^5NH$, $R^3R^6NH$, wherein $R^1$, $R^2$, $R^3$, $R^4$, $R^5$, $R^6$ have the same meanings as mentioned above.

The present invention further relates to a process for the preparation of chelate ligands according to the present invention by reaction of chelate ligands of formula (I)

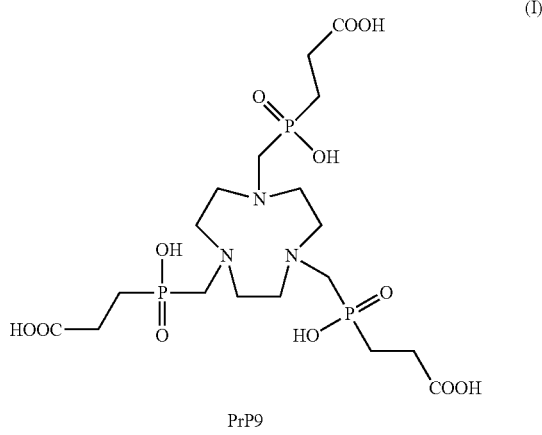 [SMILES: "PrP9" ; O=C(O)CCP(=O)(O)CN1CCN(CP(=O)(O)CCC(=O)O)CCN(CP(=O)(O)CCC(=O)O)CC1]

(I)

PrP9 with amines of general formula $R^1R^4NH$, $R^2R^5NH$, $R^3R^6NH$, wherein $R^1$, $R^2$, $R^3$, $R^4$, $R^5$, $R^6$ have the same meanings as mentioned above.

The present invention further relates to a chelate complex which comprises at least one chelate ligand according to general formula (II) and at least one metal or radiometal.

Of particular interest is furthermore the labelling of the ligands and amide derivatives with radioisotopes, where in this context, the term labelling is referring to binding of the radioactive metal ions by the chelator by means of complex formation. Suitable radioisotopes include $^{44}$Sc, $^{46}$Sc, $^{55}$Co, $^{99m}$Tc, $^{203}$Pb, $^{66}$Ga, $^{67}$Ga, $^{68}$Ga, $^{72}$As, $^{111}$In, $^{113m}$In, $^{114m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{117m}$Sn, $^{121}$Sn, $^{127}$Te, $^{142}$Pr, $^{143}$Pr, $^{198}$Au, $^{199}$Au, $^{149}$Tb, $^{161}$Tb, $^{109}$Pd, $^{165}$Dy, $^{149}$Pm, $^{51}$Pm, $^{153}$Sm, $^{157}$Gd, $^{166}$Ho, $^{172}$Tm, $^{169}$Yb, $^{175}$Yb, $^{177}$Lu, $^{105}$Rh, and $^{111}$Ag, preferably $^{44}$Sc, $^{99m}$Tc, $^{67}$Ga, $^{68}$Ga, $^{111}$In, $^{64}$Cu, $^{188}$Re, $^{90}$Y, $^{177}$Lu.

The present invention further relates to a process for the preparation of a chelate according to the present invention, wherein at least one ligand according to general formula (II) and at least one metal and/or at least one metal comprising precursor are reacted.

The present invention further relates to the method of using chelate ligands or chelates according to the present invention in molecular imaging, preferably in multimodal molecular imaging. Examples of molecular imaging are positron emission tomography (PET), single photon emission computed tomography (SPECT), planar scintigraphy, fluorescence imaging, magnet resonance tomography (MRT), optical imaging, either fluorescence or bioluminescence imaging and combinations thereof, i.e. PET/CT and PET/MRT.

In a preferred embodiment of the present invention, the compounds according to general formula (II) can be divided into compounds according to general formula (IIa), (IIb) and (IIc) as shown in the following.

In a preferred embodiment of compounds according to the present invention radicals $R^1$, $R^2$ and/or $R^3$ are connected to the core molecule via at least one linking group (LINKER). The preferred embodiment that all groups $Z^1$, $Z^2$ and $Z^3$ are different from OH is, for example, shown in general formula (IIa)

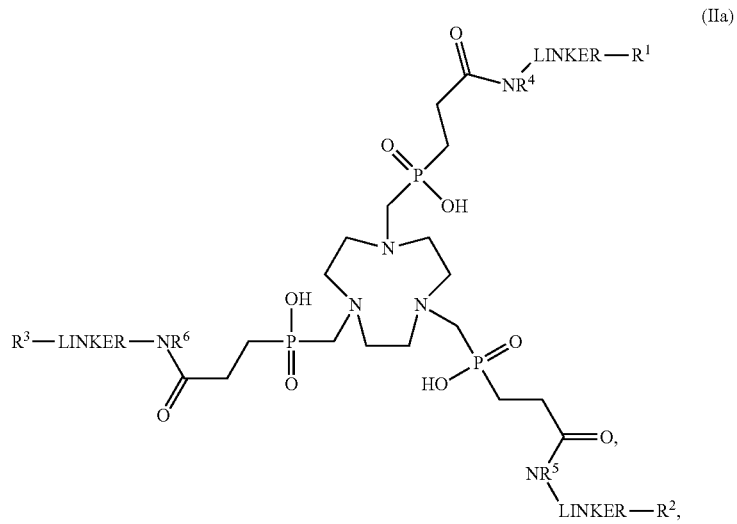

(IIa)

wherein $R^1$, $R^2$, $R^3$, $R^4$, $R^5$ and $R^6$ have the same meanings as mentioned above. In this embodiment of the present invention, not all radicals $R^1$, $R^2$ and $R^3$ have to be connected via a linking group. It is also possible that only one or two of $R^1$, $R^2$ and $R^3$ are connected via at least one linking group, whereas the remaining radicals are directly attached to the core molecule. In addition, also in case, wherein not all groups $Z^1$, $Z^2$, $Z^3$ are different from OH, linking groups my be present between $R^1$, $R^2$ or $R^3$ and the core molecule, as defined above.

In a further preferred embodiment of compounds according to the present invention radicals $R^1$, $R^2$ and/or $R^3$ are connected to the core molecule via at least one linking group (LINKER) and $R^1$, $R^2$ and/or $R^3$ are so called biomolecules, the preferred embodiment that all groups $Z^1$, $Z^2$ and $Z^3$ are different from OH is, for example, shown in general formula (IIb). It is also possible that none, only one or two of so called biomolecules are connected via at least one linking group, whereas the remaining radicals are directly attached to the core molecule.

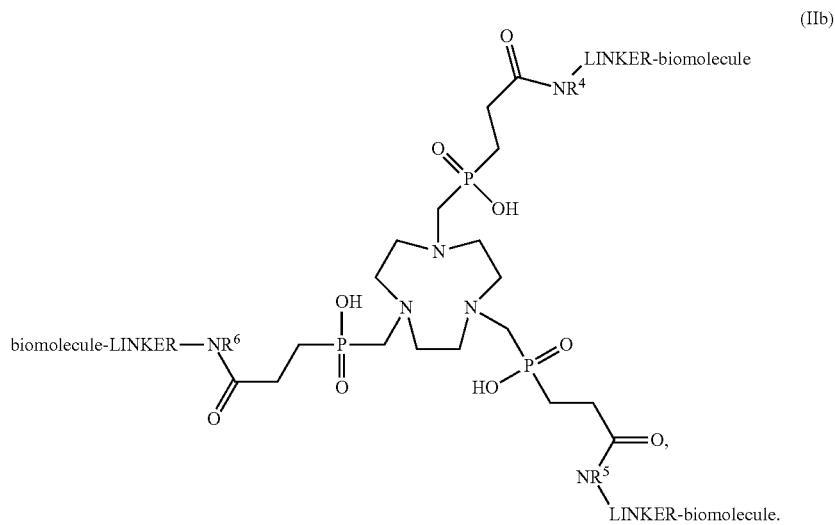

(IIb)

In addition, also in case, wherein not all groups $Z^1$, $Z^2$, $Z^3$ are different from OH, linking groups may be present between $R^1$, $R^2$ or $R^3$ and the core molecule, as defined above.

In a further preferred embodiment of the compounds according to the present invention, radicals $R^1$, $R^2$ and/or $R^3$ are so called biomolecules and/or additional signalling units, the preferred embodiments that all groups $Z^1$, $Z^2$ and $Z^3$ are different from OH are, for example, shown in general formulae (IIc)

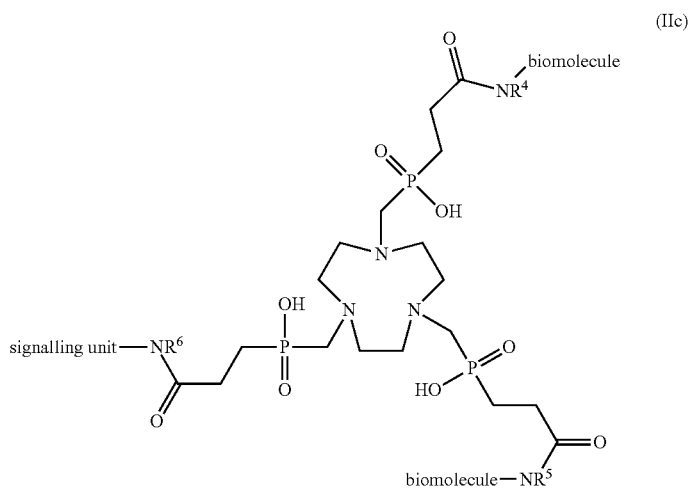

(IIc)

-continued

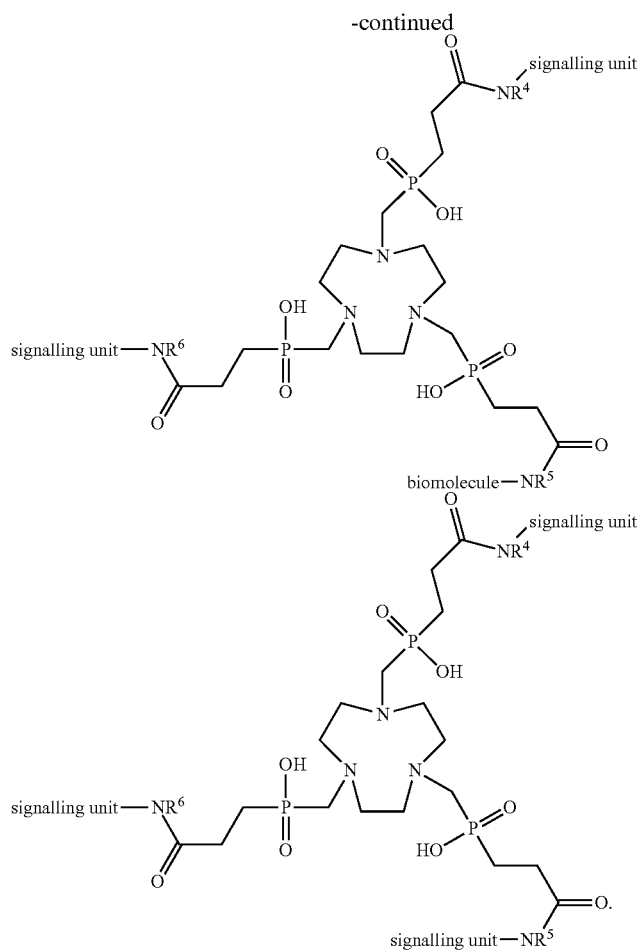

In this embodiment of the present invention, additional signalling units and/or biomolecule radicals may also be connected via a linking group. In addition, also in case, wherein not all groups $Z^1, Z^2, Z^3$ are different from OH, linking groups may be present between $R^1$, $R^2$ or $R^3$ and the core molecule, as defined above.

Additional signalling units can include chromophores, fluorophores, magnet resonance imaging (MRI) contrast agents such as chemical exchange saturation transfer (CEST) or paramagnetic chemical exchange saturation transfer (PARACEST) agents.

Compounds according to the present invention, where linking groups (LINKERS) are present, additional functional groups, for example carboxylic acid, amine, terminal alkyne, are present that allow for further functionalization of the linker groups on the other end.

According to the present invention, core molecule PrP9 (I) and the corresponding linker conjugates are further functionalized with biomolecules, e.g. the cyclic pentapeptide moiety cyclo(RGDfK). (see experimental section). In this way, precursors for radio tracers suitable for imaging of integrin expression are obtained, see for example general formula (IIa).

Also, derivatives of core molecule PrP9 (I) bearing biomolecules and additional reporter molecules, e.g. fluorophores, can be synthesized, see general formula (IIc), giving rise to tracers for application in multimodal imaging, e.g., the simultaneous application of nuclear and fluorescence imaging methods.

In general formula (II), $R^1$, $R^2$ and $R^3$ are preferably identical. Furthermore, $R^1$, $R^2$ and/or $R^3$ preferably comprise 1 to 200 carbon atoms, particularly preferably 1 to 100 carbon atoms.

$R^4$, $R^5$ and/or $R^6$ are preferably hydrogen.

In case that $R^4$, $R^5$ and/or $R^6$ are not hydrogen, they may in general comprise 1 to 200 carbon atoms, particularly preferably 1 to 100 carbon atoms.

In a further preferred embodiment, $R^1$, $R^2$ and $R^3$ are independently of another based on amines being selected from the group consisting of cyclic, aliphatic amines, amino acids esters, amino acid esters, biotin, aliphatic phosphonates, peptides, proteins, residues thereof, antibodies, antibody fragments and engineered antibody formats, anticalines, biomolecules that bind with high affinity (low nM affinity) to other proteins, receptors, transporters of other molecular targets in vivo and in vitro, biomolecules, fluorophores and mixtures thereof.

In a preferred embodiment, $R^1$, $R^2$ and $R^3$ are independently of another not based on amines being selected from the group consisting of cyclohexyl-amine, methyl-glycine, benzyl-glycine, tert-butyl-L-phenyl-alanine and mixtures thereof.

The present invention therefore preferably relates to chelate ligands according to the present invention, wherein chelate ligands having $R^1$, $R^2$ and $R^3$ that are independently of another based on amines being selected from the group consisting of cyclohexyl-amine, methyl-glycine, benzyl-glycine, tert-butyl-L-phenyl-alanine and mixtures thereof, are excluded.

In a further preferred embodiment, $R^1$, $R^2$ and $R^3$ are independently of another biomolecules selected from the group consisting of c(RGDfK)(Pbf,tBu), c(DGRKf)(Pbf,tBu), cyclo(D-Tyr$^1$-D-Orn$^2$-Arg$^3$-NaI$^4$-Gly$^5$) linked via D-Orn$^2$ (CPCR$^4$), H-D-Phe-Cys-Phe-D-Trp-Lys-Thr-Cys-Thr-ol (Disulfide bridge: 2-7), linked via D-Phe$^1$, H-D-Phe-Cys-Phe-D-Trp-Lys-Thr-Cys-Thr-OH (Disulfide bridge: 2-7), linked via D-Phe$^1$, H-D-Phe-Cys-BzThi$^3$-D-Trp-Lys-Thr-Cys-Thr-OH (Disulfide bridge: 2-7, linked via D-Phe$^1$, H-D-Phe-Cys-BzThi$^3$-D-Trp-Lys-Thr-Cys-Thr-ol (Disulfide bridge: 2-7), linked via D-Phe$^1$, linked via D-Phe$^1$, H-D-Phe-Cys-1-NaI$^3$-D-Trp-Lys-Thr-Cys-Thr-OH (Disulfide bridge: 2-7), linked via D-Phe$^1$, H-D-Phe-Cys-1-NaI$^3$-D-Trp-Lys-Thr-Cys-Thr-ol (Disulfide bridge: 2-7), [Lys$^{40}$(Ahx-DTPA)NH$_2$]-exendin-4, [Lys$^{40}$(Ahx-DOTA)NH2]-exendin-4, [Lys$^4$,Phe$^7$,Pro$^{34}$]NPY (linked via Lys$^4$) Demobesin 1, pan-bombesin, minigastrin 11 and 9, Demogastrin, CCK8 (non-sulfated), pan-somatostatin (KE-88) and mixtures thereof.

In a further preferred embodiment, $R^1$, $R^2$ and $R^3$ are independently of another selected from fluorophores selected from the group consisting of derivates of acridine, derivates of anthraquinone, arylmethane dyes, diarylmethane dyes, triarylmethane dyes, azo dyes, diazonium dyes, nitro dyes, nitroso dyes, derivates of phthalocyanine, derivates of quinone, azin dyes, eurhodin dyes, safranin dyes, indamins, indophenol dyes, oxazin dyes, oxazone dyes, thiazin dyes, thiazole dyes, derivates of thiazole, xanthene dyes, fluorene dyes, pyronin dyes, fluorone dyes, Rhodamine dyes, Porphyrine dyes, Cyanine dyes (Merocyanine, Indocyanine), coumarine dyes, stilbene derivatives, anthracene derivatives, styrylpyridinium dye, naphthalimid derivatives, squarine dyes, carbazoles, perylene derivatives, pyrene/benzopyrene derivatives, indol derivatives (tryptophan etc.), flavones, quinolinium dyes, pyridin derivatives, BODIPY dyes, ethidium dyes, naphthalene derivatives, ruthenium complexes, e.g. Ru bipyridine, Pd porphyrin complexes and mixtures thereof.

In a further preferred embodiment, $R^1$, $R^2$ and $R^3$ are independently of another selected from CEST or PARACEST agents selected from the group of lanthanoid metal ion chelates, particularly those based on azamacrocyclic chelating units, such as DOTA complexes.

In a further preferred embodiment, linking groups (LINKER) that attach radicals $R^1$, $R^2$ and/or $R^3$ to the core molecule (I) are independently of another selected from natural and unnatural amin acids, like glutamic acid, aspartic acid, lysine, glycine, alanine, proline, serine, threonine, phenylalanine, tyrosine, to mention only a few, peptide linkers, amino acid esters, difunctional molecules, such as co-amino-carboxylic acids (H$_2$N—(CH$_2$)$_n$—COOH, n=1–12) or polyalkyleneoxide based molecules, e.g. polyethyleneoxide based amino carboxylic acid esters, and mixtures thereof.

Particularly preferred radicals $R^1$, $R^2$, $R^3$, linking groups, biomolecules, fluorophores according to the present invention are shown in the examples.

Particularly preferred chelate ligands according to the present invention have the following formulae

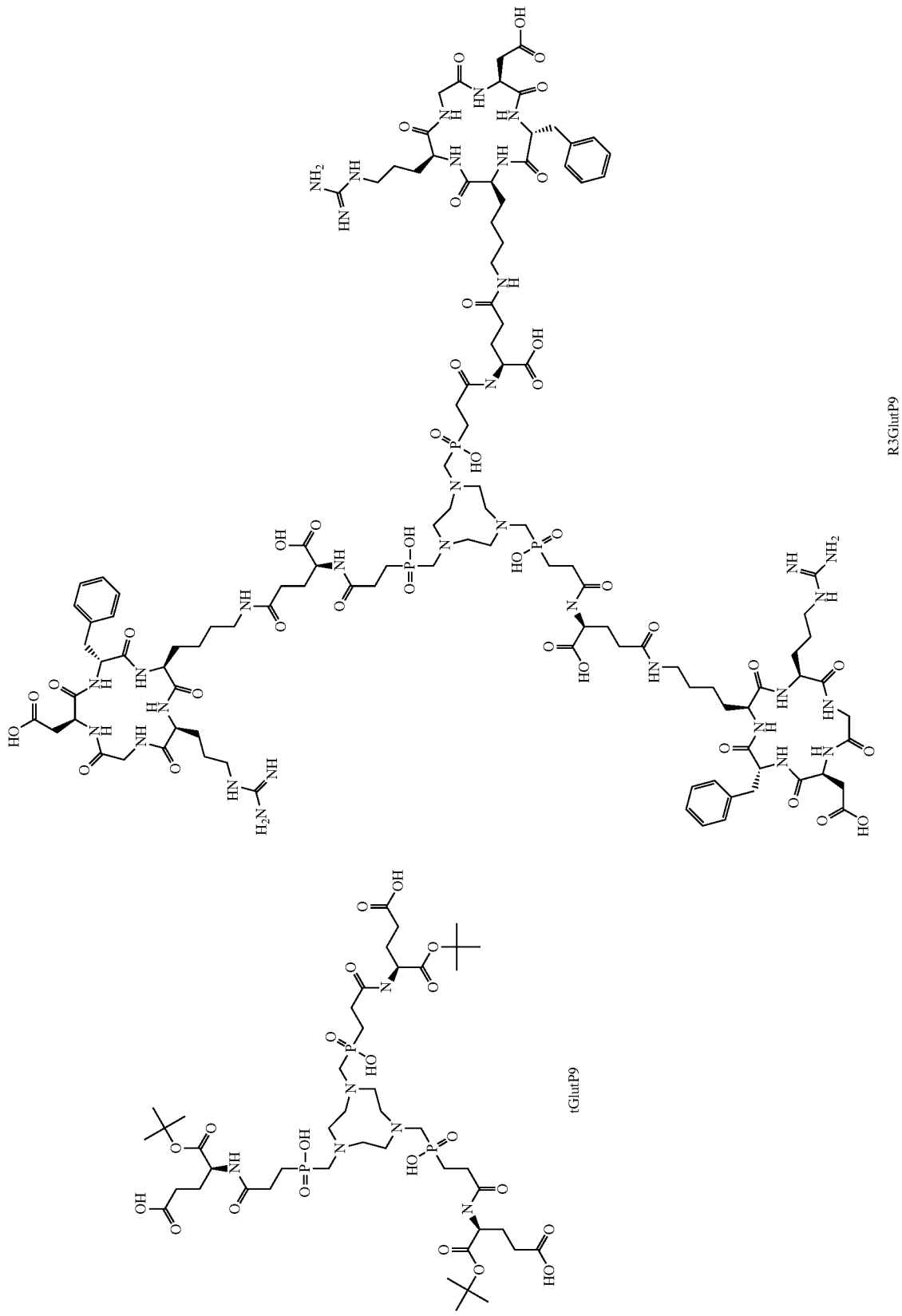

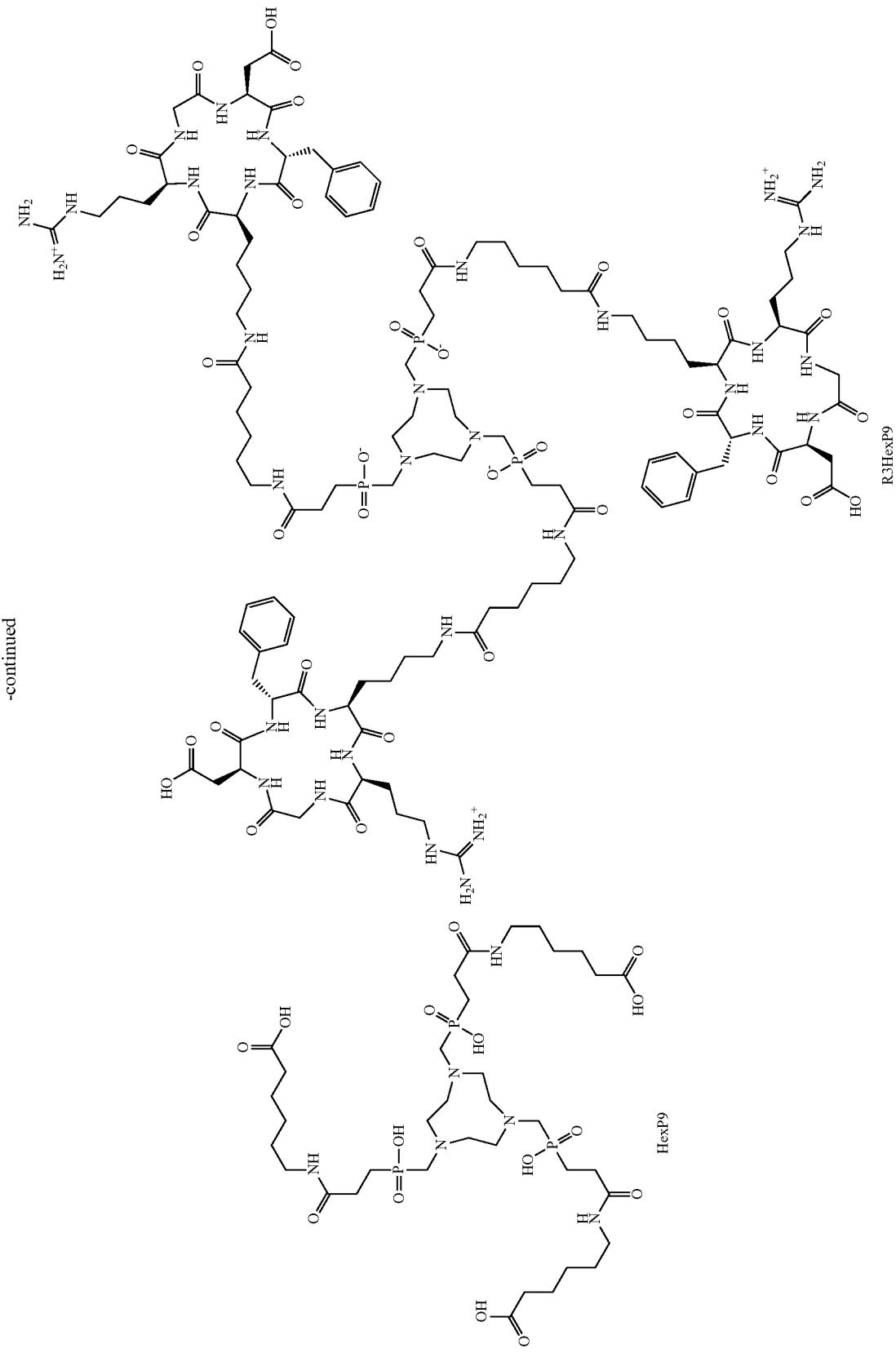

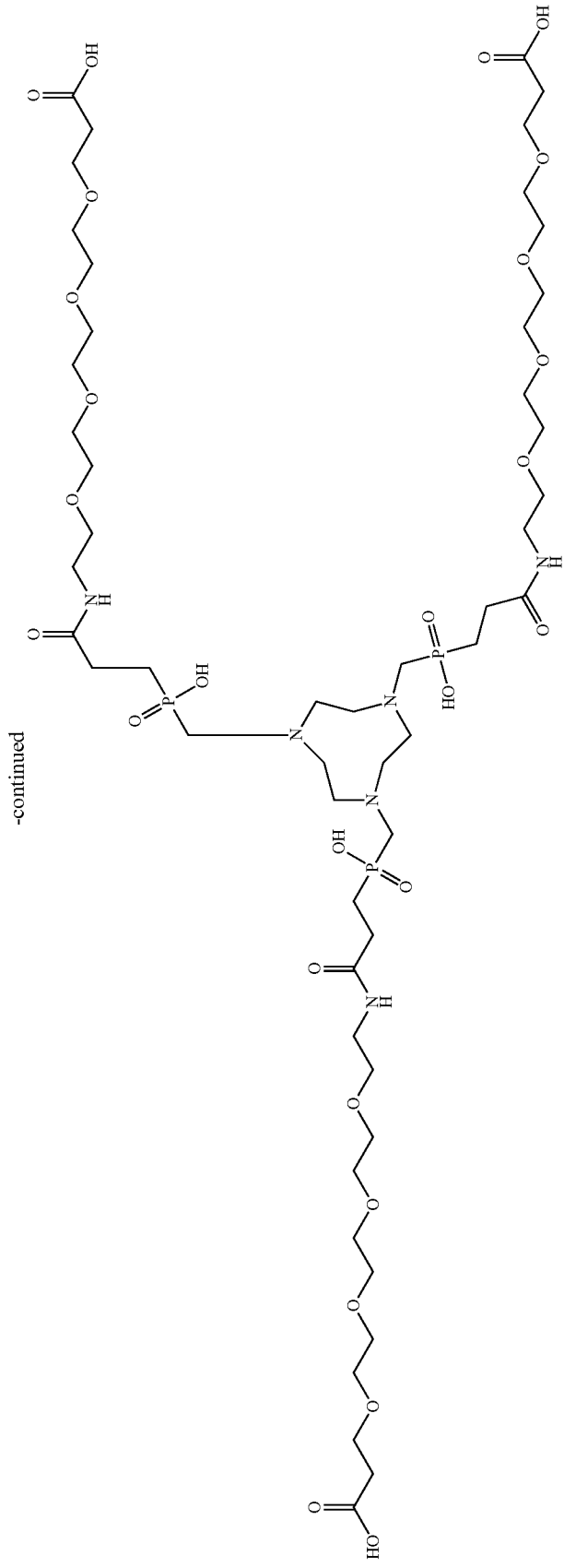
-continued
PEG4P9

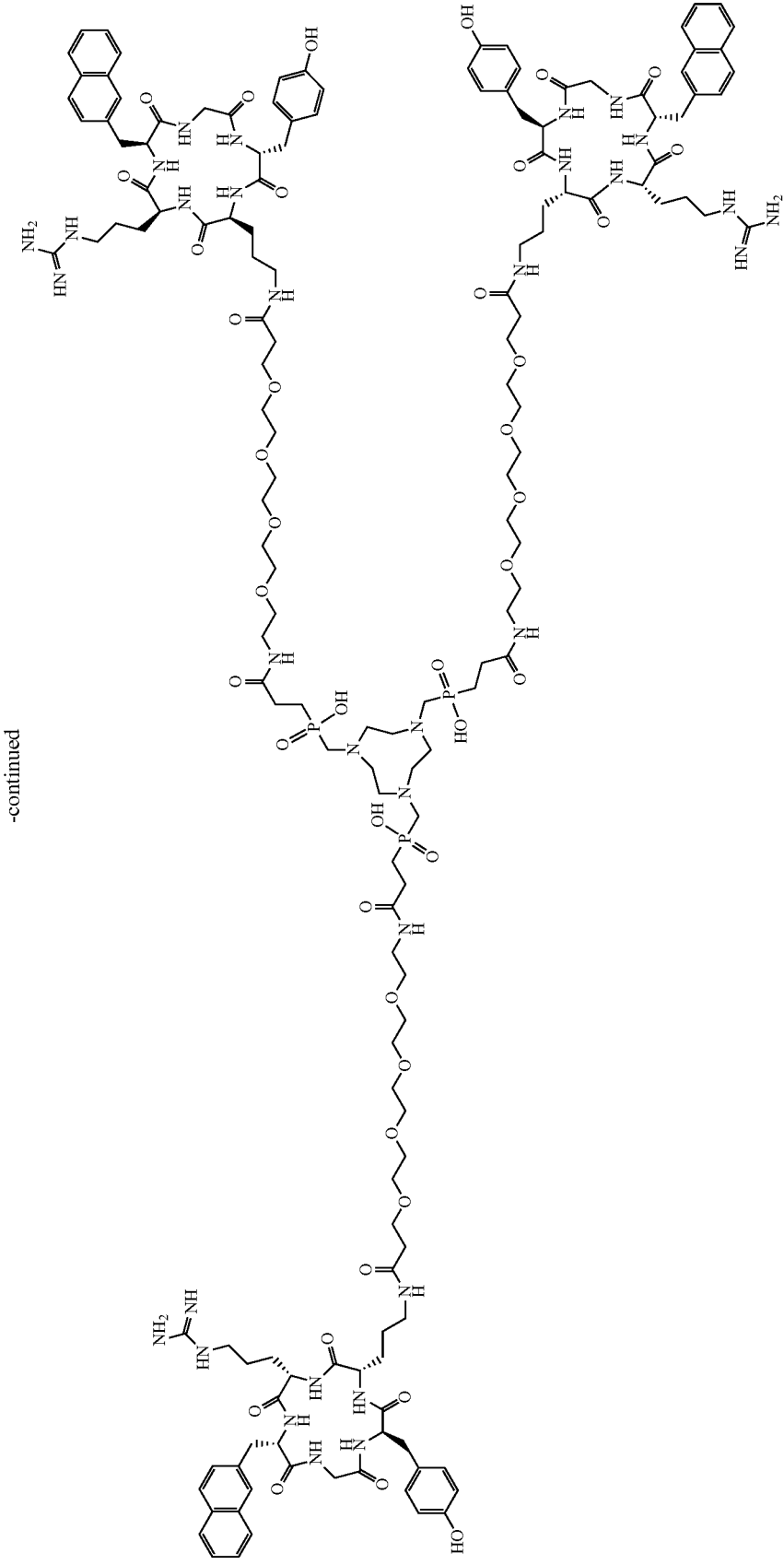
C3PEG4P9

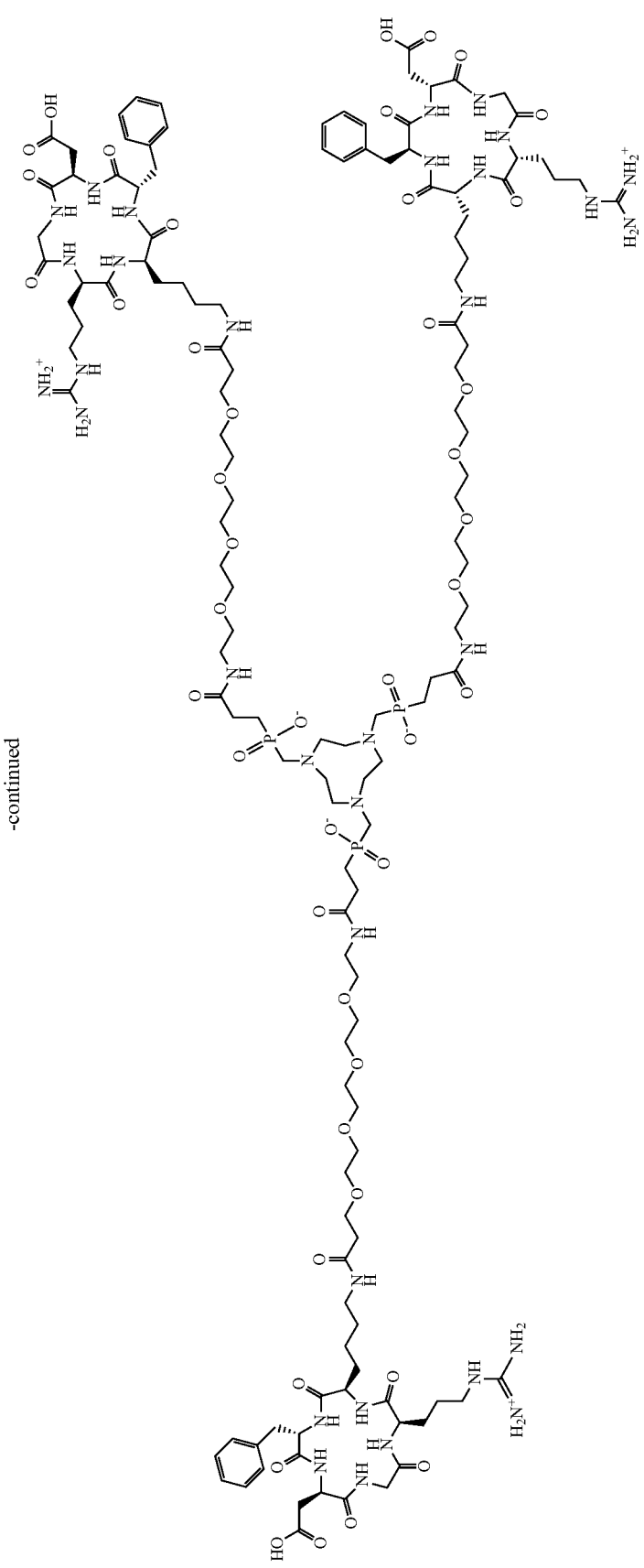
isoR3PEG4P9

-continued
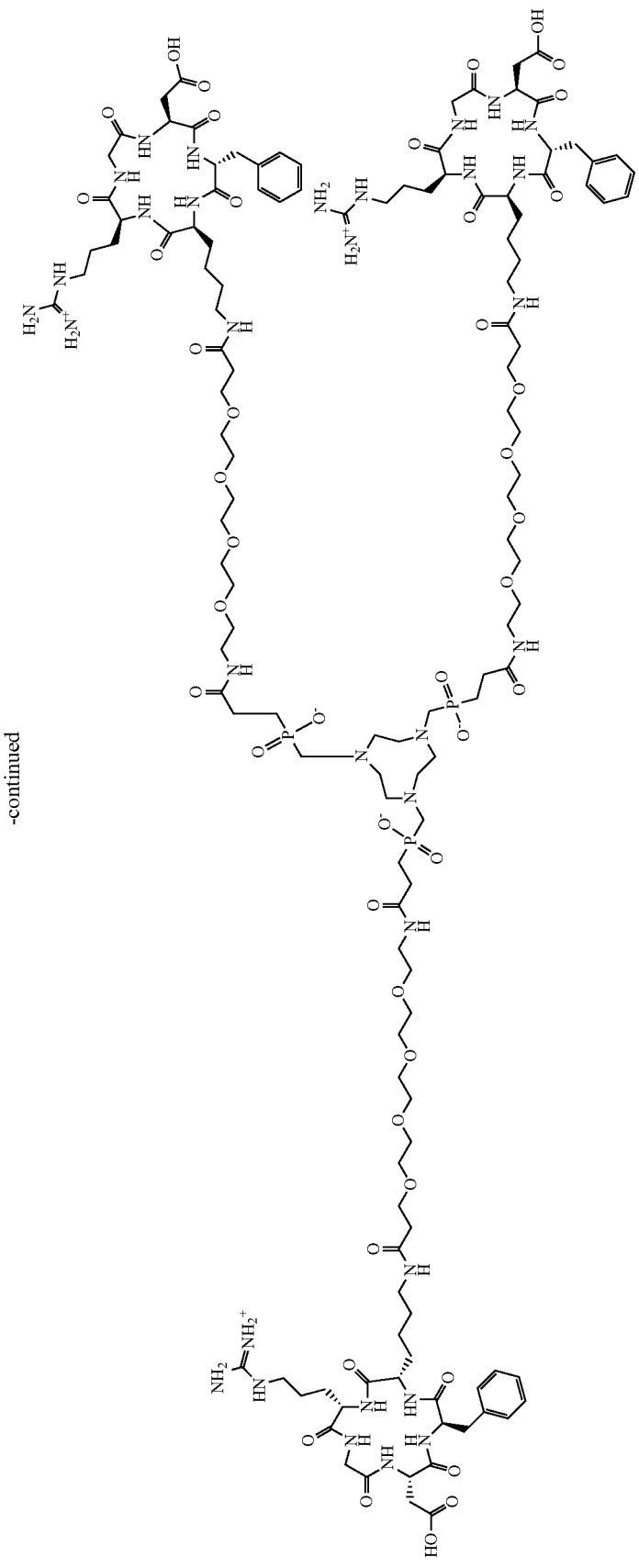
R3PEG4P9

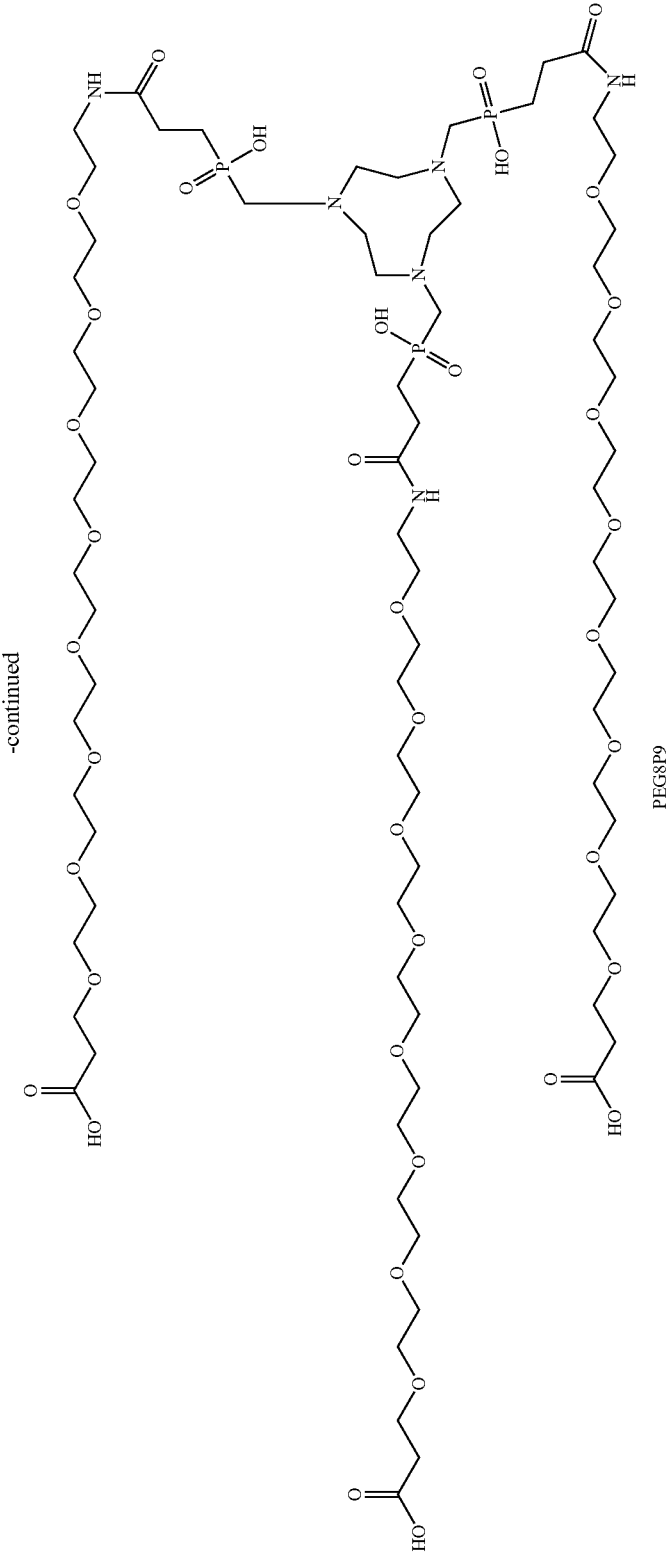

-continued
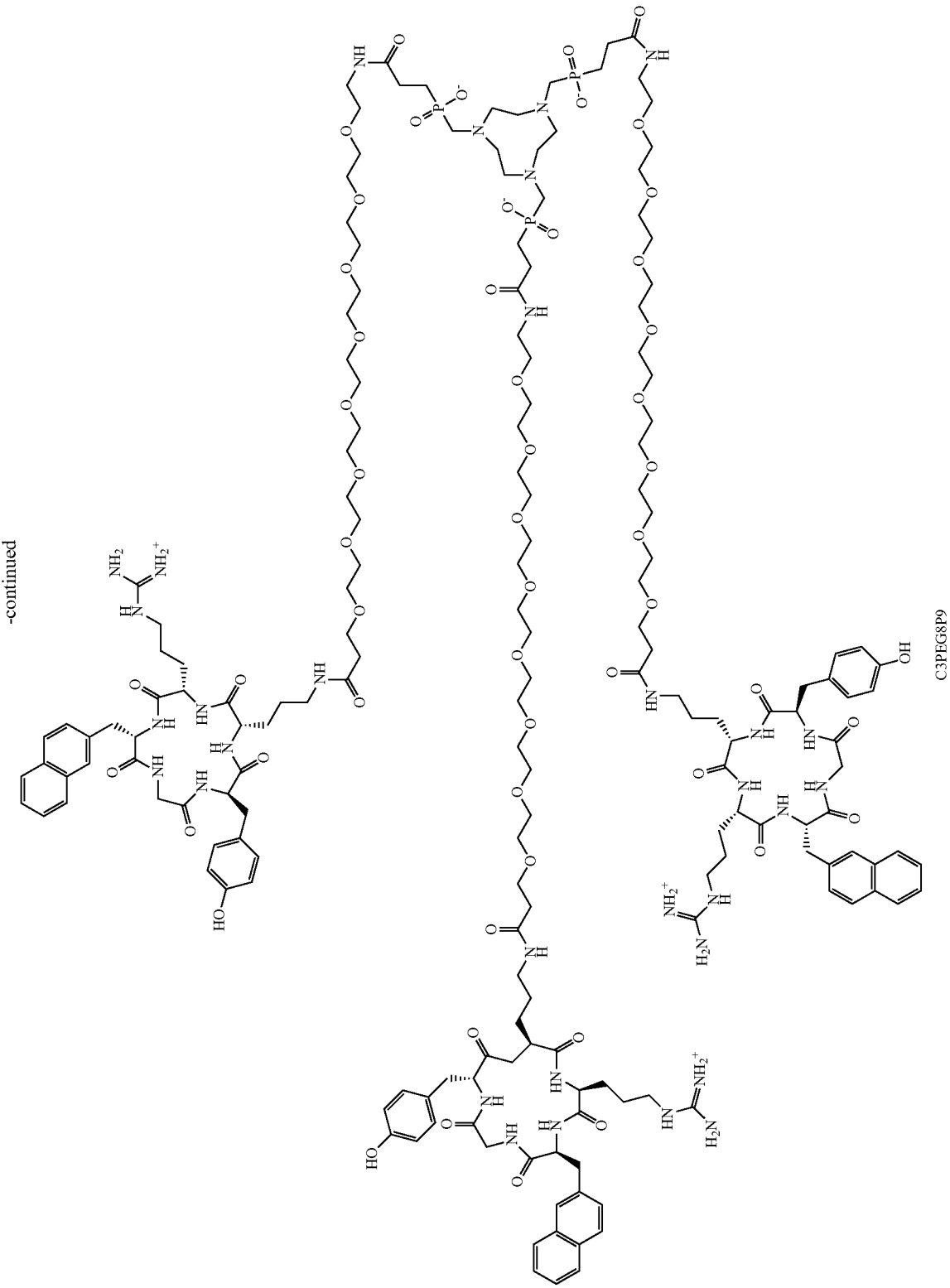
C3PEG8P9

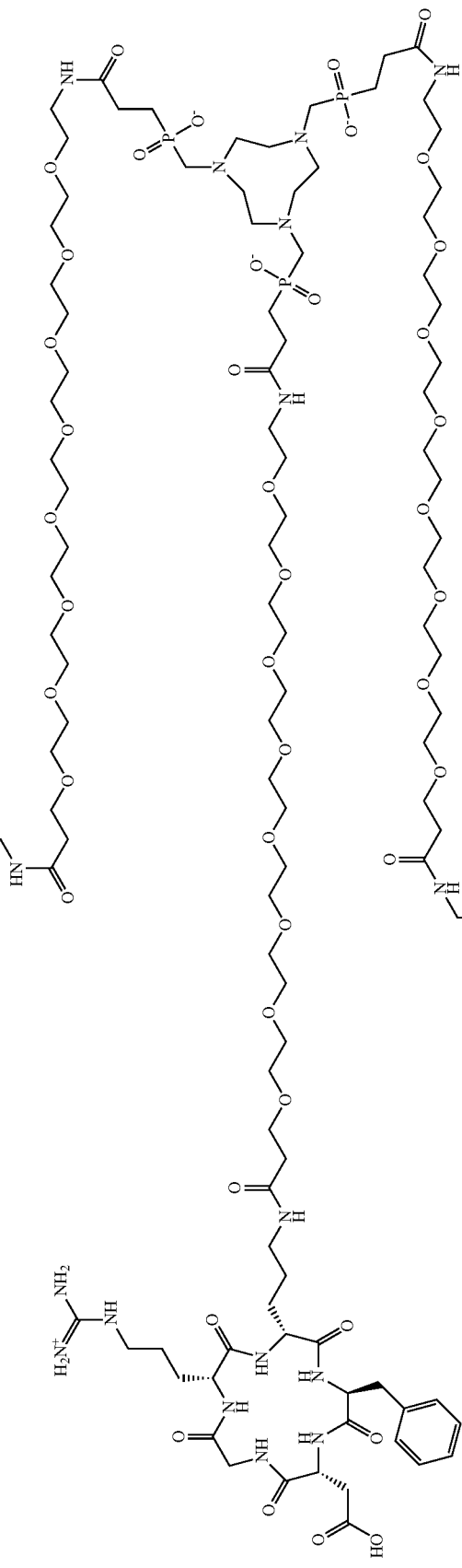

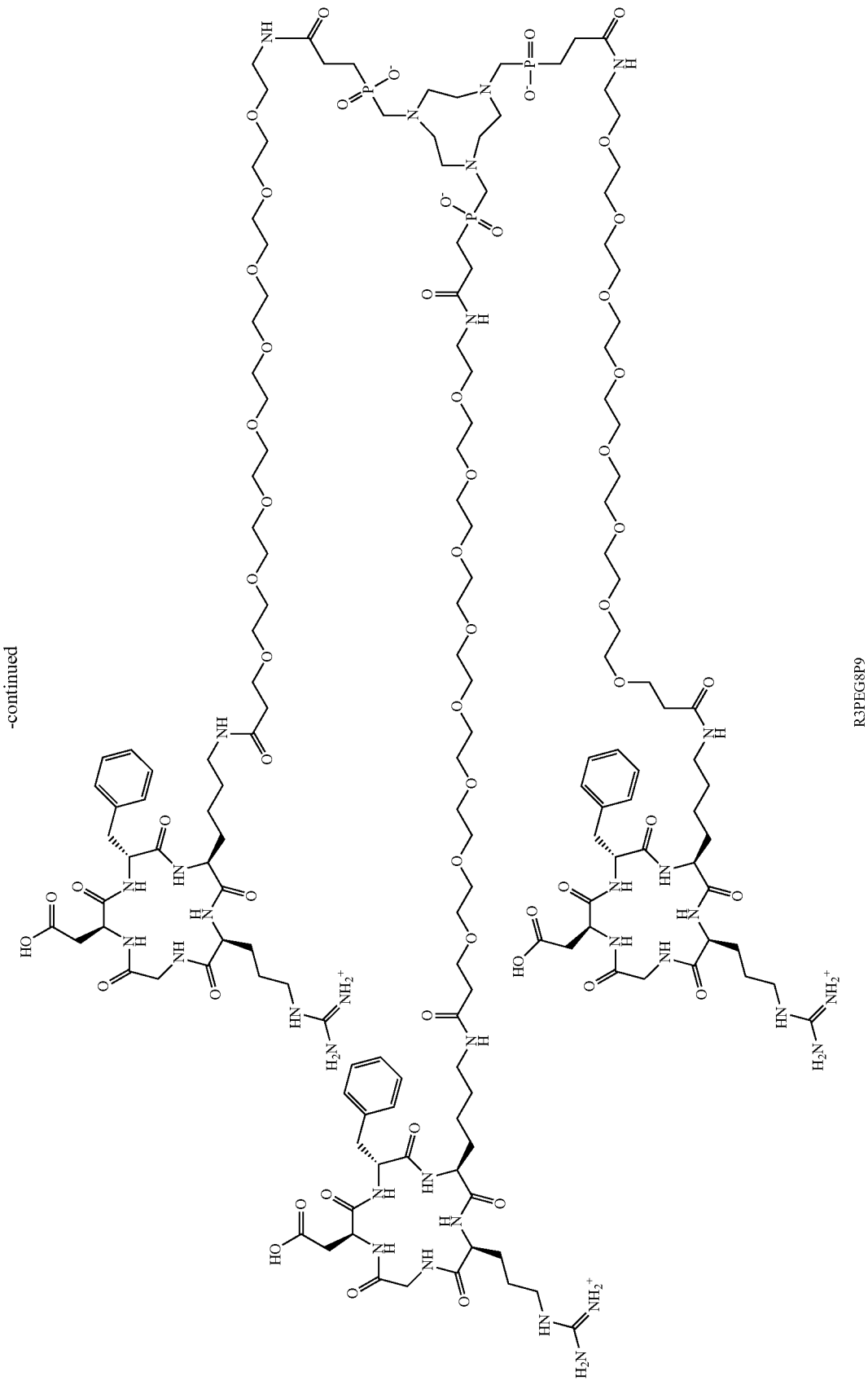

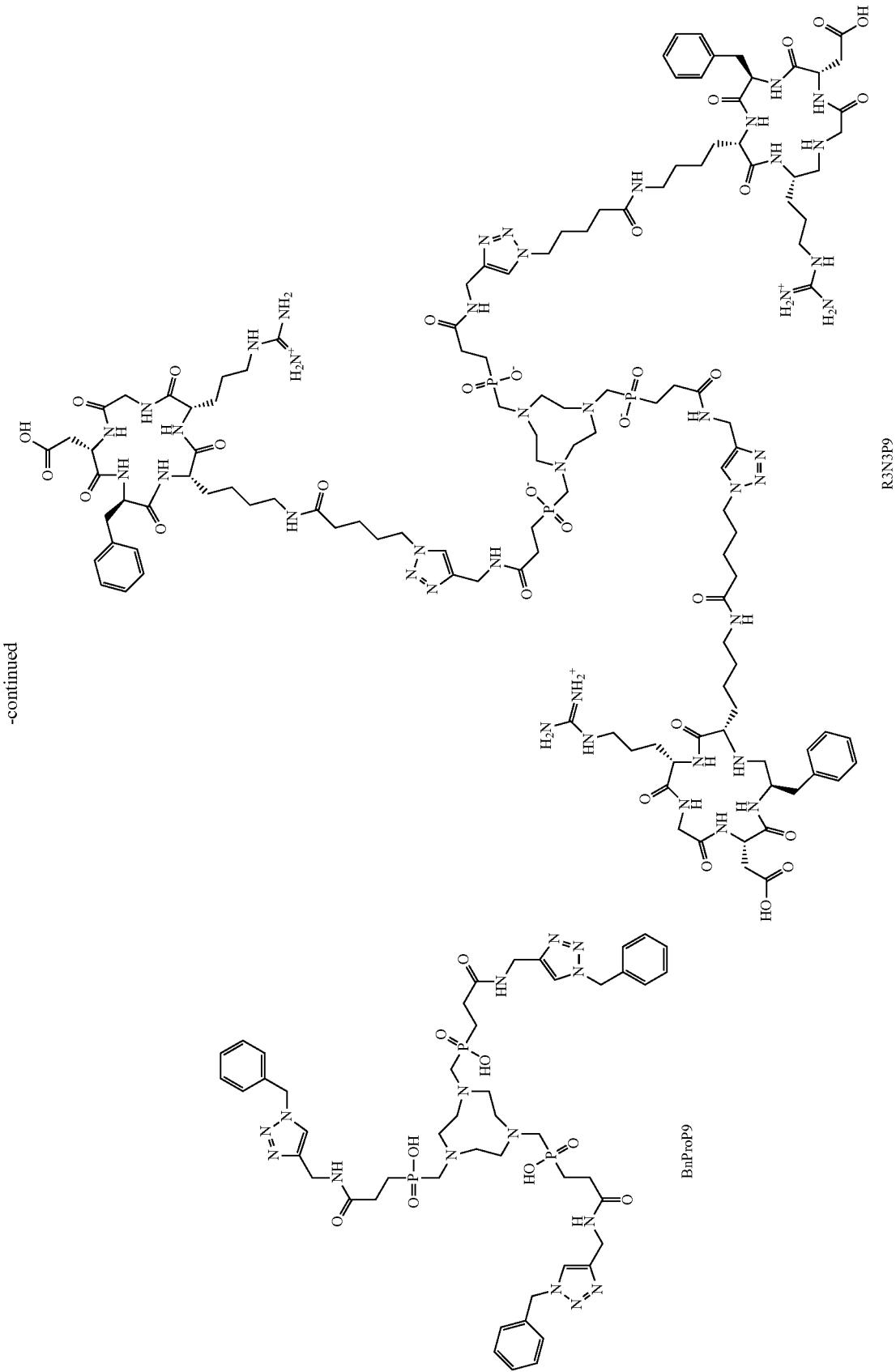

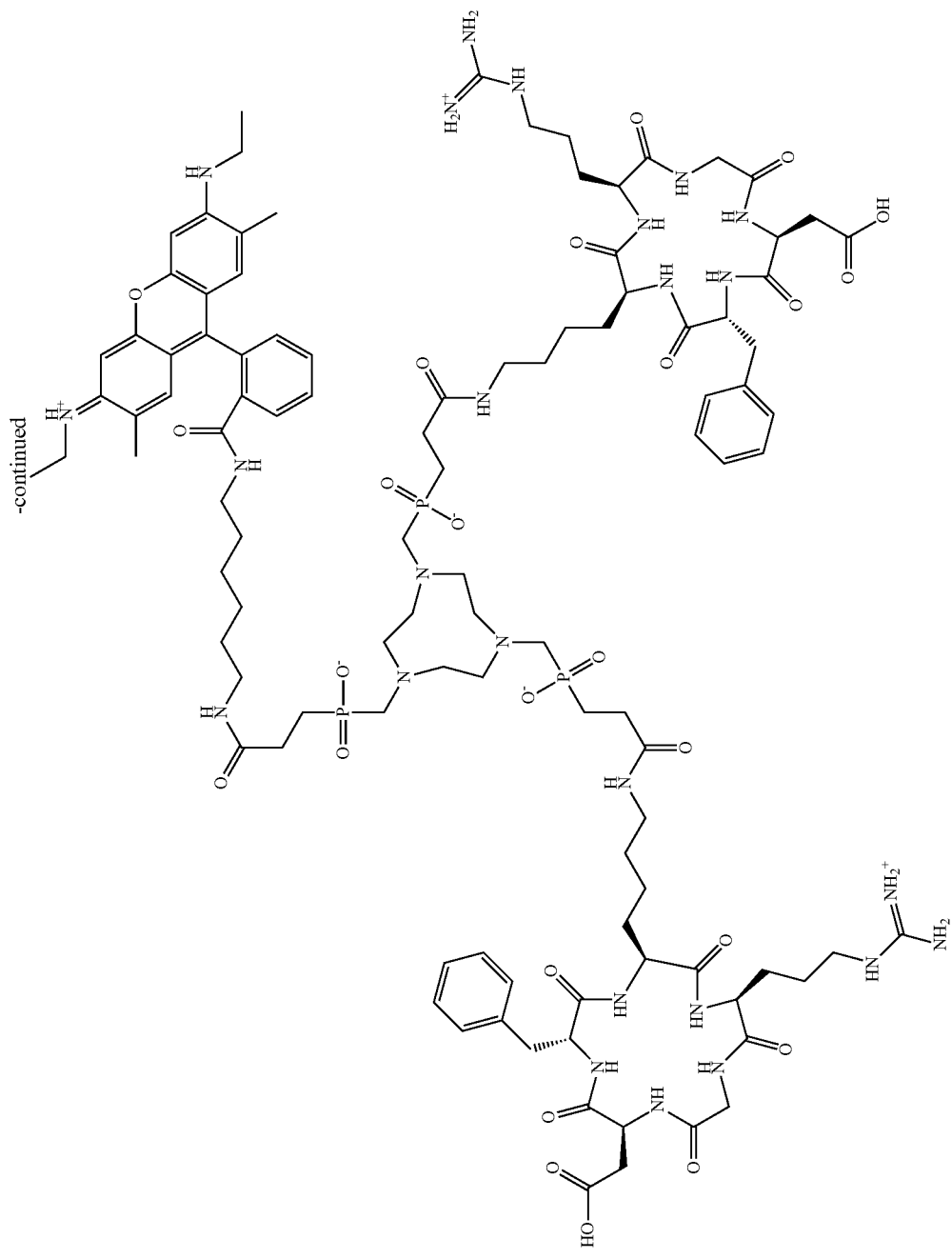
R2RhoP9

The present invention further relates to a process for the preparation of chelate ligands according to general formula (II) by reaction of chelate ligands of formula (I)

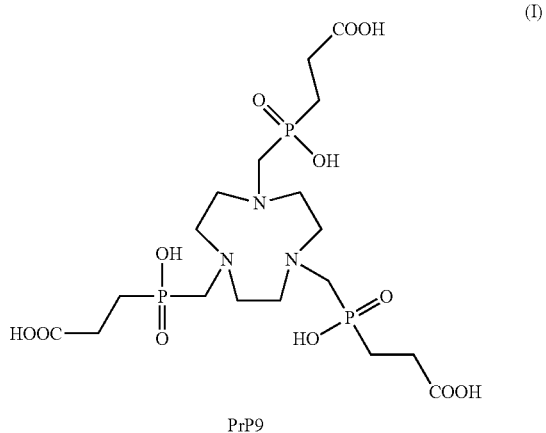

PrP9 with $R^1R^4NH$, $R^2R^5NH$, $R^3R^6NH$, wherein $R^1$, $R^2$, $R^3$, $R^4$, $R^5$, $R^6$ have the same meanings as to mentioned above.

PrP9 according to compound formula (I) bears three carboxylic acid groups which allow for functionalization by amide formation with e.g. amines comprising $R^1$, $R^2$, $R^3$, $R^4$, $R^5$ and/or $R^6$ as mentioned above, biomolecules and/or fluorophores, optionally attached via linking groups, in order to obtain radiotracers.

Coupling of PrP9 according to formula (I) and suitable amines can in general be conducted according to methods known to the skilled artisan and described for example in Chem. Eur. J. 2010, 16, 7174-7185.

The process according to the present invention can be conducted in any suitable solvent, for example dimethylformamide (DMF), dimethyl sulfoxide (DMSO), dimethylacetamide (DMA), N-methylpyrrolidinone (NMP) or mixtures thereof.

The process according to the present invention can be conducted using any suitable additive that is known to the skilled artisan for supporting amide coupling reactions, for example di-iso-propyl-ethyl-amine (DIPEA), triethylamine (TEA), 1,8-Diazabicyclo[5.4.0]undec-7-en (DBU), 1,5-Diazabicyclo[4.3.0]non-5-ene (DBN), or mixtures thereof.

The process according to the present invention can be conducted using any suitable coupling agent, for example 2-(1H-7-azabenzotriazol-1-yl)-1,1,3,3-tetramethyluronium hexafluorophosphate methanaminium (HATU), 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (HBTU), O-(benzotriazol-1-yl)-N,N,N',N'-tetramethyluronium tetrafluoroborate (TBTU), benzotriazole-1-yl-oxy-tris-(dimethylamino)phosphonium hexafluorophosphate (BOP), (benzotriazol-1-yloxy)tripyrrolidinophosphonium hexafluorophosphate (PyBOP), 3(ethyliminomethyleneamino)-N,N-dimethyl-propan-1-amine (EDC), N,N'-dicyclohexylcarbodiimide (DCC), N,N'-diisopropylcarbodiimide (DIC), 3-(diethoxyphosphoryloxy)-3H-benzo[d][1,2,3]triazin-4-one (DEPBT), N,N'-carbonyldiimidazole (CDI), O-(6-chloro-1-hydroxybenzotriazol-1-yl)-1,1,3,3-tetramethyluronium tetrafluoroborate (TCTU), O-(7-azabenzotriazole-1-yl)-N,N,N'N'-tetramethyluronium tetrafluoroborate (TATU), bromo-tris-pyrrolidinophosphonium hexafluorophosphate (PyBrOP), 2-(6-chloro-1H-benzotriazole-1-yl)-1,1,3,3-tetramethylaminium hexafluorophosphate) or mixtures thereof.

In respect of amines $R^1R^4NH$, $R^2R^5NH$ and/or $R^3R^6NH$, wherein $R^1$, $R^2$, $R^3$, $R^4$, $R^5$, $R^6$ have the same meanings as mentioned above. Furthermore, the specific definitions that have been made according to general formula (II), also apply here.

The present invention further relates to a chelate comprising at least one chelate ligand according to general formula (II) as defined above and at least one metal or radiometal.

In a preferred embodiment, the present invention relates to a chelate according to the present invention, wherein the at least one metal or radiometal is selected from the group consisting of $La^{3+}$, $Ce^{3+}$, $Pr^{3+}$, $Nd^{3+}$, $Sm^{3+}$, $Eu^{2+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, $Sc^{3+}$, $Y^{3+}$, $Al^{3+}$, $Ga^{3+}$, $Ge^{4+}$, $In^{3+}$, $As^{3+}$, $Sn^{2+}$, $Sn^{4+}$, $Sc^{3+}$, $Ti^{4+}$, $V^{5+}$, $Cr^{3+}$, $Mn^{2+}$, $Fe^{3+}$, $Co^{2+}$, $Co^{3+}$, $Ni^{2+}$, $Cu^{1+}$, $Cu^{2+}$, $Zn^{2+}$, $Cd^{2+}$ and mixtures thereof.

In a particular preferred embodiment, the present invention relates to a chelate according to the present invention, wherein the at least one radiometal is selected from the group consisting of $^{44}Sc$, $^{46}Sc$, $^{55}Co$, $^{99m}Tc$, $^{203}Pb$, $^{66}Ga$, $^{67}Ga$, $^{68}Ga$, $^{72}Ga$, $^{111}In$, $^{113m}In$, $^{114m}In$, $^{97}Ru$, $^{62}Cu$, $^{64}Cu$, $^{52}Fe$, $^{52m}Mn$, $^{51}Cr$, $^{186}Re$, $^{188}Re$, $^{77}As$, $^{90}Y$, $^{67}Cu$, $^{169}Er$, $^{117m}Sn$, $^{121}Sn$, $^{127}Te$, $^{142}Pr$, $^{143}Pr$, $^{198}Au$, $^{199}Au$, $^{149}Tb$, $^{161}Tb$, $^{109}Pd$, $^{165}Dy$, $^{149}Pm$, $^{151}Pm$, $^{153}Sm$, $^{157}Gd$, $^{166}Ho$, $^{172}Tm$, $^{169}Yb$, $^{175}Yb$, $^{177}Lu$, $^{105}Rh$, $^{111}Ag$ and mixtures thereof, preferably selected from the group consisting of $^{44}Sc$, $^{99m}Tc$, $^{67}Ga$, $^{68}Ga$, $^{111}In$, $^{64}Cu$, $^{188}Re$, $^{90}Y$, $^{177}Lu$ and mixtures thereof. In respect of the mentioned radiometals, preferably the oxidation state as mentioned above is present.

A particularly preferred metal is Ga, in particular $^{68}Ga$, very particularly $^{68}Ga^{3+}$. Nuclear metal atoms and ions are prepared according to methods known to the skilled artisan, for example by generator based preparation. Suitable compounds comprising the mentioned metal ions are for example aqueous or other solutions of metal salts, such as clorides, nitrates, sulfates, phosphates, carbonates, hydrogencarbonates.

In a preferred embodiment of the chelates according to the present invention, $R^1$, $R^2$ and $R^3$ are independently of another not based on amines being selected from the group consisting of cyclohexyl-amine, methyl-glycine, benzyl-glycine, tert-butyl-L-phenyl-alanine and mixtures thereof.

The present invention therefore preferably relates to chelates according to the present invention, wherein chelates having $R^1$, $R^2$ and $R^3$ that are independently of another based on amines being selected from the group consisting of cyclohexyl-amine, methyl-glycine, benzyl-glycine, tert-butyl-L-phenyl-alanine and mixtures thereof, are excluded.

Complexation with Metals and Complexation with Radiometals

The present invention further relates to a process for the preparation of a chelate according to the present invention, wherein at least one residue $R^1$, $R^2$, $R^3$ according to general formula (II) and the PrP9 core is labelled with at least one metal or radiometal.

Preferably, the present invention relates to the process according to the present invention, wherein the at least one metal or radiometal is selected from the group consisting of $La^{3+}$, $Ce^{3+}$, $Pr^{3+}$, $Nd^{3+}$, $Sm^{3+}$, $Eu^{2+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, $Sc^{3+}$, $Y^{3+}$, $Al^{3+}$, $Ga^{3+}$, $Ge^{4+}$, $In^{3+}$, $As^{3+}$, $Sn^{2+}$, $Sn^{4+}$, $Sc^{3+}$, $Ti^{4+}$, $V^{5+}$, $Cr^{3+}$, $Mn^{2+}$, $Fe^{3+}$, $Co^{2+}$, $Co^{3+}$, $Ni^{2+}$, $Cu^{1+}$, $Cu^{2+}$, $Zn^{2+}$, $Cd^{2+}$ and mixtures thereof.

Particularly preferably, the present invention relates to the process according to the present invention, wherein the at least one radiometal is selected from the group consisting of $^{44}Sc$, $^{46}Sc$, $^{55}Co$, $^{99m}Tc$, $^{203}Pb$, $^{66}Ga$, $^{67}Ga$, $^{68}Ga$, $^{72}As$, $^{111}In$, $^{113m}In$, $^{14m}In$, $^{97}Ru$, $^{62}Cu$, $^{64}Cu$, $^{52}Fe$, $^{52m}Mn$, $^{51}Cr$, $^{186}Re$, $^{188}Re$, $^{77}As$, $^{90}Y$, $^{67}Cu$, $^{169}Er$, $^{117m}Sn$, $^{121}Sn$, $^{127}Te$, $^{142}Pr$, $^{143}Pr$, $^{198}Au$, $^{199}Au$, $^{149}Tb$, $^{161}Tb$, $^{109}Pd$, $^{165}Dy$, $^{149}Pm$, $^{151}Pm$, $^{153}Sm$, $^{157}Gd$, $^{166}Ho$, $^{172}Tm$, $^{169}Yb$, $^{175}Yb$, $^{177}Lu$, $^{105}Rh$, $^{111}Ag$ and mixtures thereof, preferably selected from the group consisting of $^{44}Sc$, $^{99m}Tc$, $^{67}Ga$, $^{68}Ga$, $^{111}In$, $^{64}Cu$, $^{188}Re$, $^{90}Y$, $^{177}Lu$ and mixtures thereof. In respect of the mentioned radiometals, preferably the oxidation state as mentioned above is present.

For example, the $^{68}Ga$ labelling of a symmetrical c(RGDfK)-PEG4-conjugate of PrP9, R3PEG4P9 (see below), has been performed with generator-produced $^{68}Ga$ using an automated system for labelling (for details see experimental section). On the same system, peptide conjugates of the competing chelators DOTA and NODAGA, namely DOTATOC and NODAGA-RGD (see figure) have been labelled.

Preclinical Studies

Due to the high specific activity, tracers, being chelates comprising chelate ligands according to the present invention and metals obtained as described above can be used directly for preclinical studies using small animals, without the necessity of prior separation of the labelled compound from the precursor, i.e., the functionalized chelator without radiometal ion. This is of importance because in small animals such as rodents, the absolute molar amount of injected tracer will affect the result of the study, particularly in case the addressed receptor/tissue is saturable.

As an example, the PEG4-linked cyclo(RGDfK) conjugate R3PEG4P9 was evaluated in mice with tumor xenografts (see Experimental section). Biodistribution studies as well as PET imaging showed the suitability of the tracer for imaging of integrin expression. Moreover, the analysis of metabolites proved that the compound is fully stable in vivo.

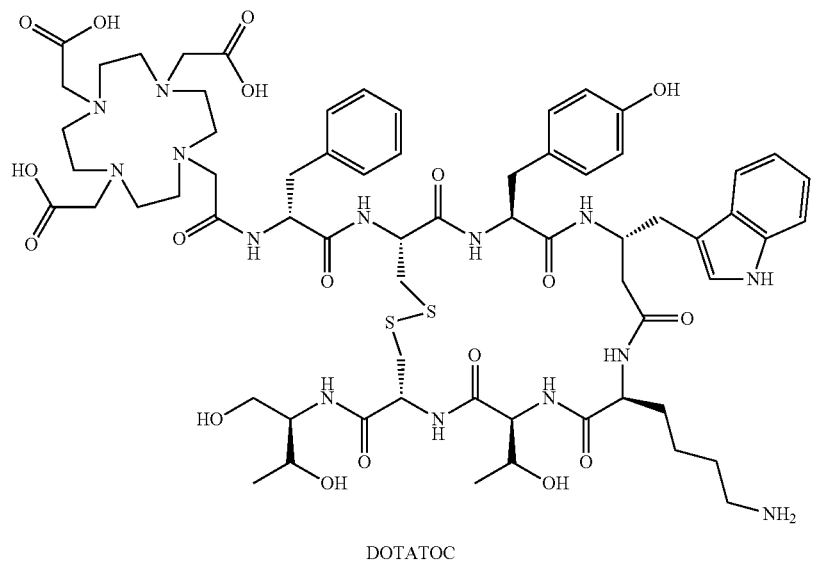

DOTATOC

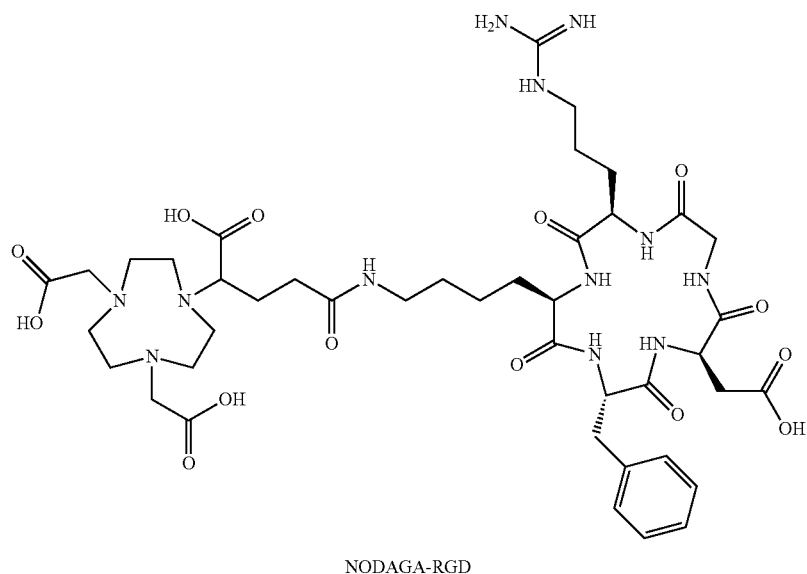

NODAGA-RGD

Figure 1:
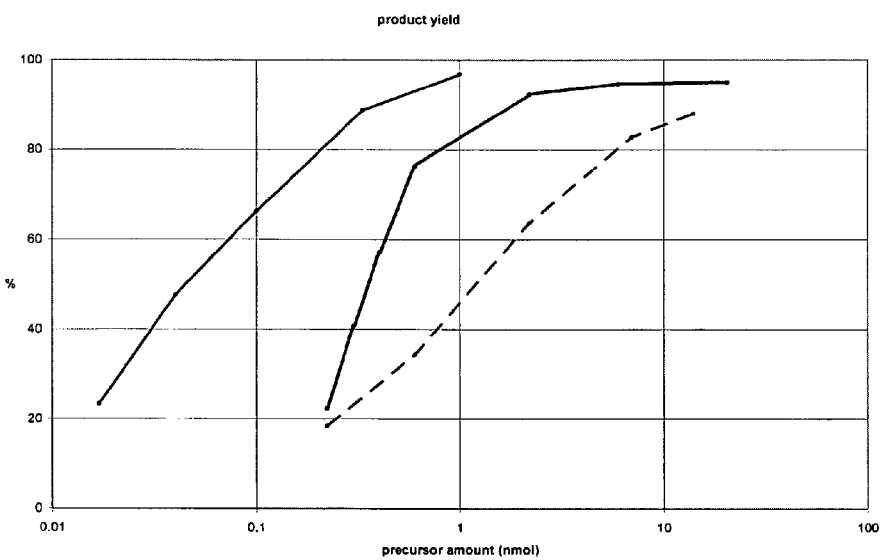
FIG. 1 shows product yields for the preparation of $^{68}$Ga-R3PEG4P9 (solid line), $^{68}$Ga-DOTATOC (dashed line) and $^{68}$Ga-NODAGA-RGD (semi-transparent line), are given as functions of precursor amount.
Figure 2:
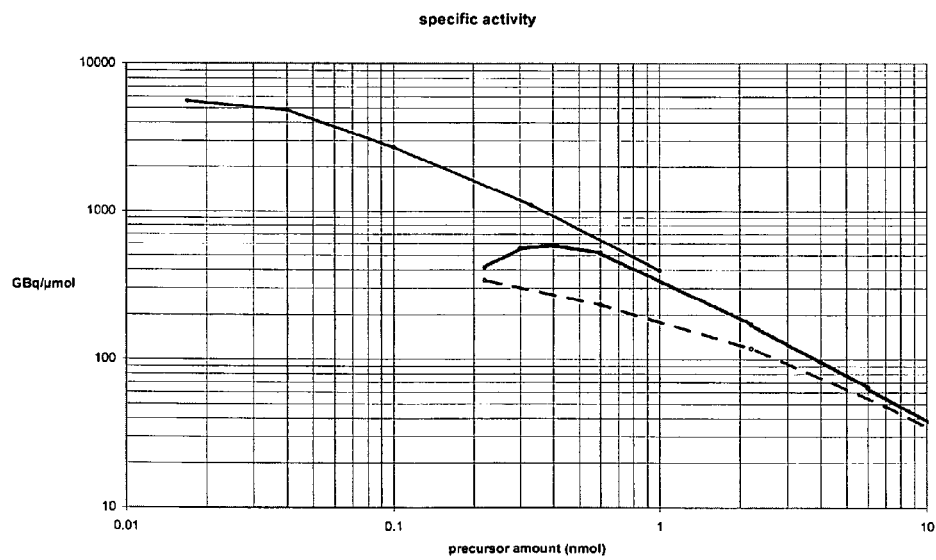
FIG. 2 shows the specific activities for preparations of $^{68}$Ga-R3PEG4P9 (solid line), $^{68}$Ga-DOTATOC (dashed lines) and $^{68}$Ga-NODAGA-RGD (semi-transparent lines) 30 min after the start of the synthesis (t=30 min). The initial $^{68}$Ga activity (t=0) was 15 mCi (555 MBq). (In practice, slightly varying $^{68}$Ga amounts (400-600 MBq) were used; the data thus obtained were normalized.)

The curves show that in comparison, the amount of R3PEG4P9 necessary for high labelling yields is lower than in case of DOATOC and NODAGA-RGD, thus increasing the maximal achievable specific activity (here: >4 TBq/µmol). At optimal pH conditions for labelling of the latter compounds (3.2-3.3, see experimental section), the maximum specific activity of DOTATOC is limited to <400 GBq/µmol and of NODAGA-RGD to <600 GBq/µmol. In contrast, R3PEG4P9 can easily be labelled at pH 1.8, reaching specific activities above 1000 GBq/µmol and up to 5000 GBq/µmol.

FIG. 3: Data from the table under the headline "Biodistribution of $^{68}$Ga-R3PEG4P9" is visualized in the chart.

FIGS. 4a-h: HPLC chromatograms of $^{68}$Ga-R3PEG4P9 (for reference) and the analyzed extracts referred to under the headline "Metabolite studies for $^{68}$Ga-R3PEG4P9" are shown, indicating that no metabolites could be detected.

FIG. 5: The graphic shows PET images derived from data measured 60-90 min after injection (maximum intensity projections; left: R3PEG4P9, center: R3PEG4P9 with blockade, right: isoR3PEG4P9).

FIGS. 6a-c: The charts (FIG. 6) show distribution kinetics derived from PET data.

EXPERIMENTAL & EXAMPLES

General

Analytical HPLC was performed using a Sykam HPLC system with low-pressure gradient mixer, equipped with a Nucleosil C18-RP column (100×4.6 mm, 5 µm particle size), at a flow rate of 1 ml/min. Eluents were water and acetonitrile, both containing 0.1% trifluoroacetic acid (TFA). Two gradients were used: Gradient A, 20-80% MeCN in 24 min and Gradient B, 40-100% MeCN in 24 min.

Preparative HPLC was done using a Sykam system with two separate solvent pumps, equipped with a YMC C18ec column (250×30 mm, 5 µm particle size), at a flow rate of 20 ml/min. Solvents were similar to analytical HPLC. Separations were generally done in isocratic mode with eluent compositions individually optimized for each compound (see below). ESI–MS was measured on a Varian LC-MS system.

Peptide Synthesis

The protected cyclic pentapeptides (see scheme below) were prepared according to literature protocols, using standard methods for solid phase peptide synthesis (Fmoc strategy).

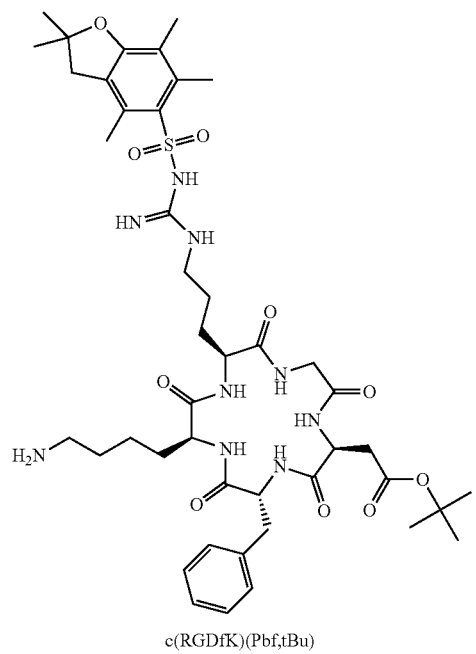

c(RGDfK)(Pbf,tBu)

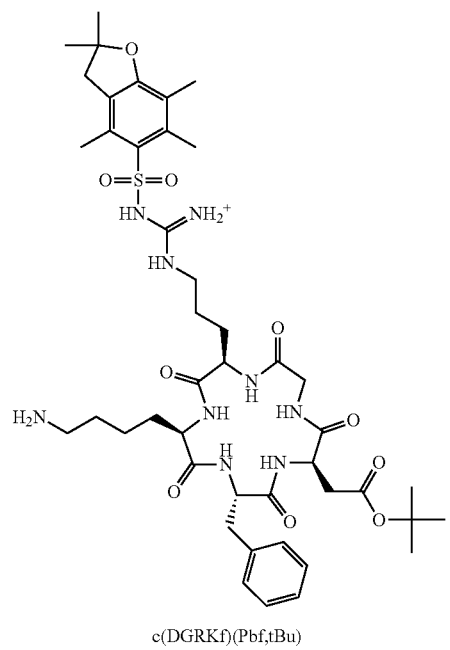

c(DGRKf)(Pbf,tBu)

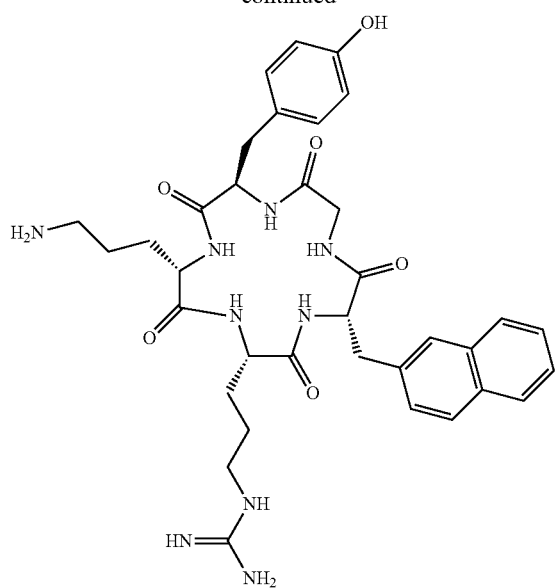

CPCR4

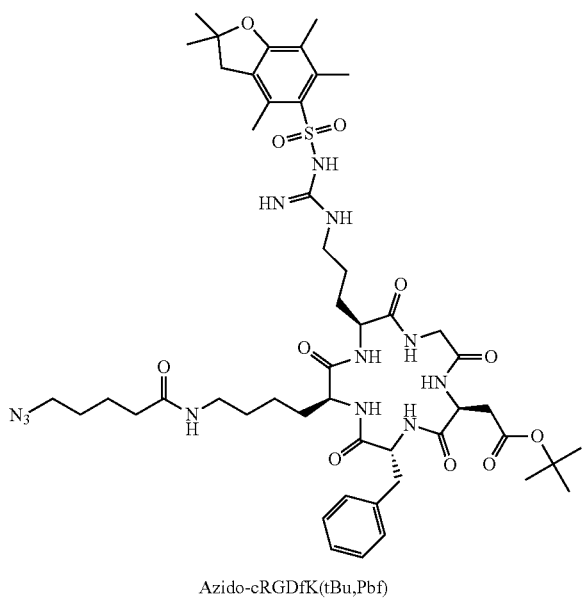

Azido-cRGDfK(tBu,Pbf)

5-Azidopentanoic acid (28.6 mg) and DIPEA (65 mg, 85 µl) were dissolved in DMF (0.5 ml). Then HATU (84 mg) was added with stirring. After 5 min, cRGDfK(Pbf,tBu) (100 mg), dissolved in DMF (0.5 ml) was added. After 10 min, the product was precipitated by slow addition of the reaction mixture to 10 ml of brine, and centrifuged. The liquid was poured off, the solids redissolved in 0.2 ml DMF, and precipitated by addition of diethyl ether (10 ml). After centrifugation and removal of the ether phase the product was stirred in ethanol (1 ml) and again ether was added for precipitation. After another centrifugation, the solid was separated off and dried in vacuo. Yield: 77 mg.

General Synthetic Procedure for Coupling of Amines Using HATU

Molar amounts of reagents used are given below for each synthesis and individual compounds.

PrP9 or its derivatives with linkers, diisopropylethylamine (DIPEA) and the amine were dissolved in DMSO. Then HATU was added with stirring. RP-HPLC was used for reaction control. After the reaction had finished, workup was performed according to solubility of the products. In case of water-soluble compounds, the reaction mixtures were diluted with water and subjected to diafiltration with 0.05 M NaCl solution and then pure water (Amicon stirred cell, membrane with 0.5 kDa MWCO), followed by lyophilisation of the cell contents. Products not soluble in water were precipitated by slow addition of the reaction mixture to brine. The solids were separated by centrifugation and dried in vacuo.

In case some remaining impurities were detected in the crude product, further purification was done using preparative HPLC. Following this step, the organic part of the eluent was removed in vacuo and the remaining aqueous solutions lyophilized to yield the final products.

General Procedure for Removal of Acid-Sensitive Protecting Groups (Pbf, tBu)

The dry compound was dissolved in 0.5-1 ml trifluoroacetic acid and allowed to react for 24 h. Then, the mixture was slowly added to diethyl ether, the precipitate separated by centrifugation and dried in vacuo. If necessary, purification was done using preparative HPLC, followed by concentration of the eluates and lyophilization to yield the final products.

Syntheses

R1P9, R2P9

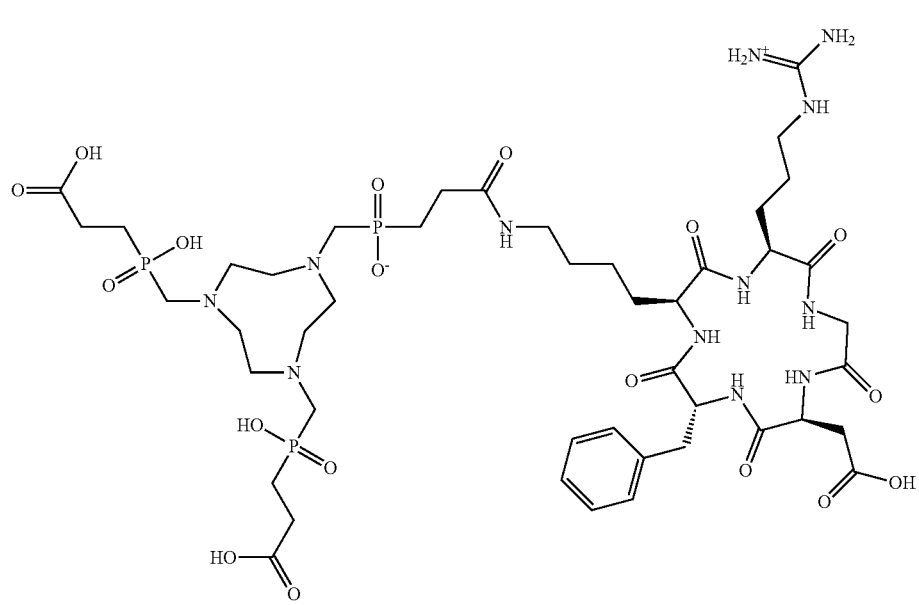

R1P9

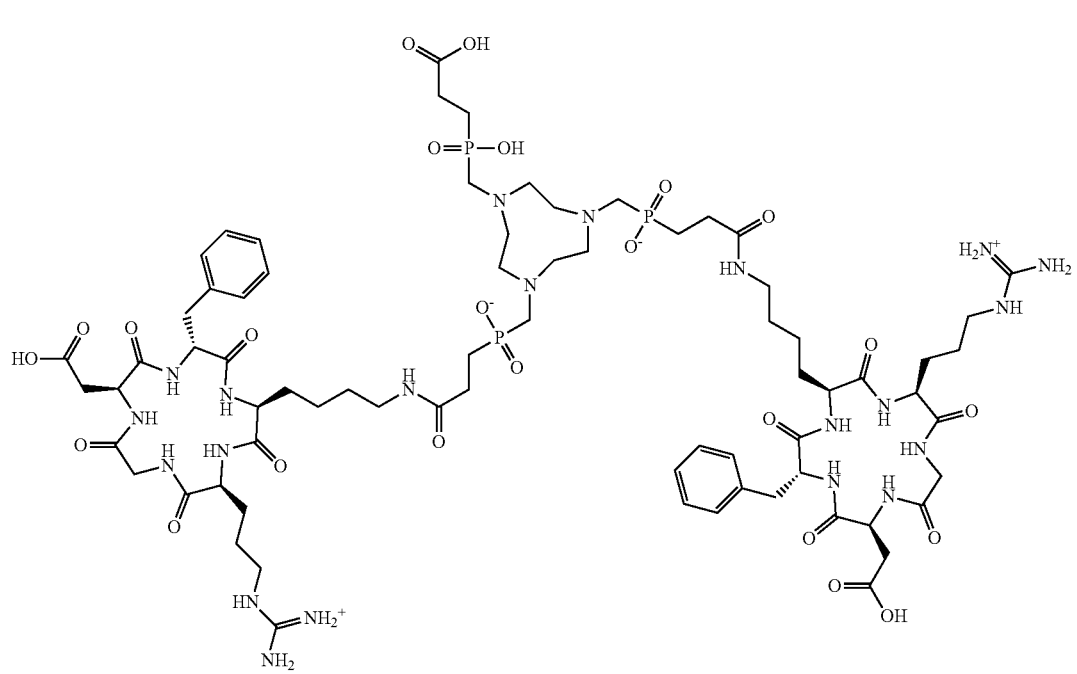

R2P9

General coupling protocol using PrP9 (62 mg), DMSO (1 ml), DIPEA (258 mg, 340 µl), cRGDfK(Pbf,tBu) (100 mg), HATU (305 mg).

Reaction time: 10 min. $t_R$ of R1P9 (Gradient B): 8.5 min; $t_R$ of R2P9 (Gradient B): 14 min. Workup: Ultrafiltration. Purification by preparative HPLC (two-stage isocratic elution: 47% MeCN for 10 min, followed by 63% MeCN for another 10 min, thus providing purified pR1P9 and pR2P9 in one separation run).

Yield: 39 mg of pR1P9 and 22 mg of pR2P9.

Acidic deprotection directly yielded the compounds R1P9 and R2P9 in quantitative yield.

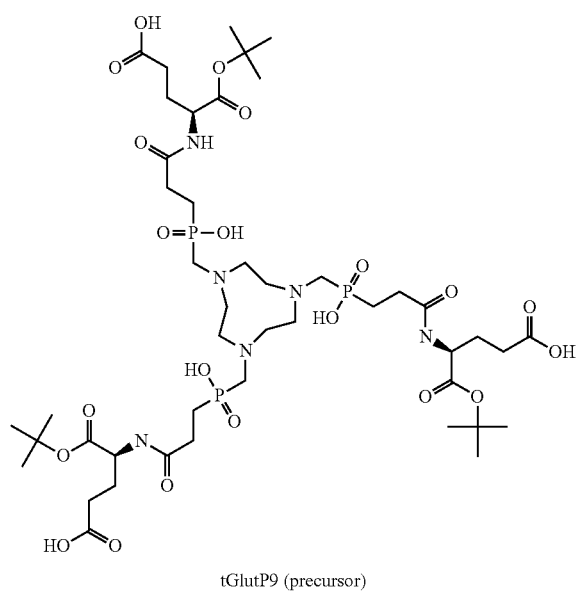 [SMILES: CC(C)(C)OC(=O)[C@H](CCC(=O)O)NC(=O)CCP(=O)(O)CN1CCN(CP(=O)(O)CCC(=O)N[C@@H](CCC(=O)O)C(=O)OC(C)(C)C)CCN(CP(=O)(O)CCC(=O)N[C@@H](CCC(=O)O)C(=O)OC(C)(C)C)CC1]

tGlutP9 (precursor)

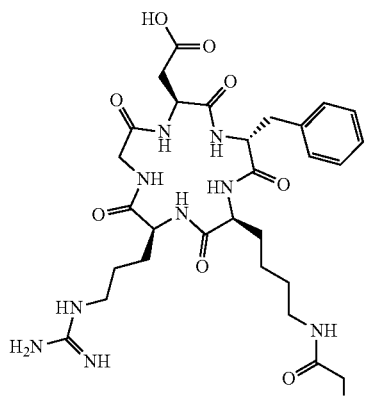

General coupling protocol using PrP9 (512 mg), DMSO (12 ml), DIPEA (1560 mg, 2 ml), benzylglutamic acid tert-butyl ester hydrochloride (1320 mg), HATU (2 g).

Reaction time: 24 h. Workup: Precipitation, then purification by preparative HPLC (80% MeCN, $t_R$=10 min). Collected eluates were concentrated, neutralized by addition of aq. Na—HCO3, the salts precipitated by addition of tert-butanol, and lyophilized. Yield: 880 mg. Debenzylation was done by stirring 220 mg of BtGlutP9 in 5 ml methanol with 50 mg Pd/C under hydrogen atmosphere for 3 h. The mixture was filtered through celite and the solvent removed in vacuo. Yield: 115 mg.

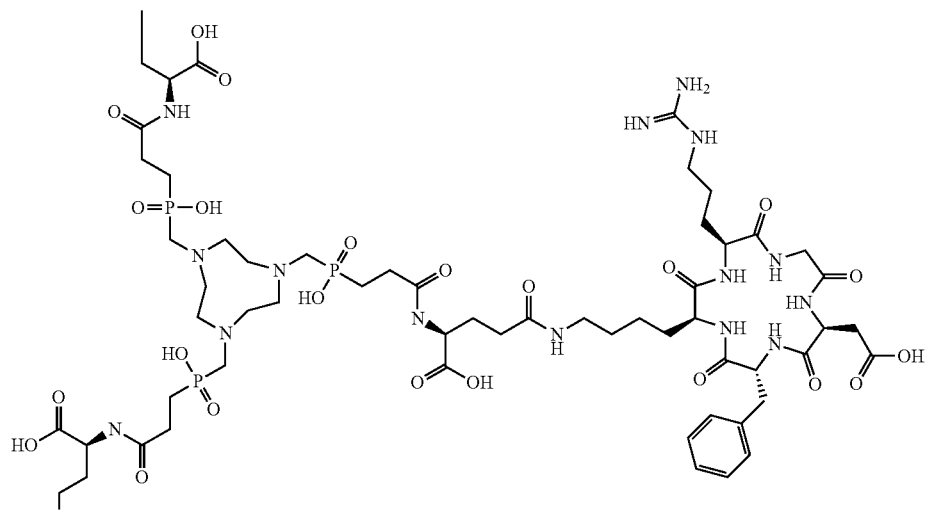

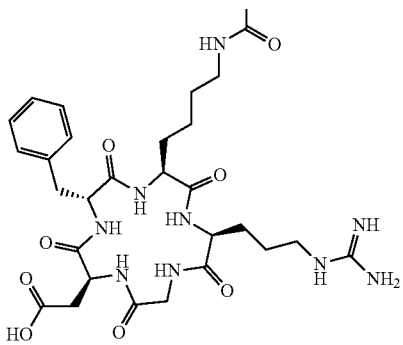

R3GlutP9

General coupling protocol using tGlutP9 (20 mg) DMSO (0.5 ml), DIPEA (41 mg, 54 µl), cRGDfK(Pbf,tBu) (80 mg), HATU (49 mg).

Reaction time: 10 min. $t_R$ (Gradient B): 20 min. Workup: Precipitation, followed by acidic deprotection. Purification: preparative HPLC (22% MeCN, $t_R$ ca. 15 min). Yield: 28 mg.

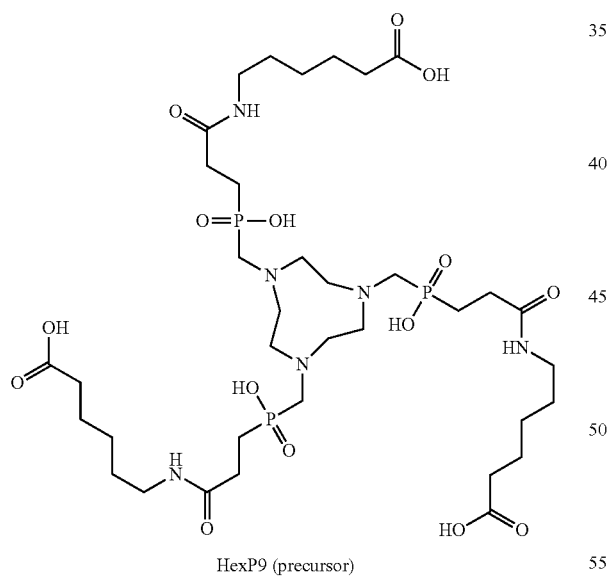

HexP9 (precursor)

General coupling protocol using PrP9 (308 mg), DIPEA (967 mg, 1280 µl), DMSO (5 ml), methyl-6-aminohexanoic acid hydrochloride (455 mg), HATU (1.52 g).

Reaction time: 10 min. $t_R$ (Gradient A): 11.5 min. Workup: Ultrafiltration. Deprotection was done by dissolving the methyl ester in a mixture of water (2 ml) and methanol (6 ml) MeOH containing LiOH (100 mg) and allowing to react at 4° C. for 72 h. $t_R$ (Gradient A): ca. 7 min. Purification by preparative HPLC (19% MeCN, $t_R$ ca. 14 min). Yield: 183 mg.

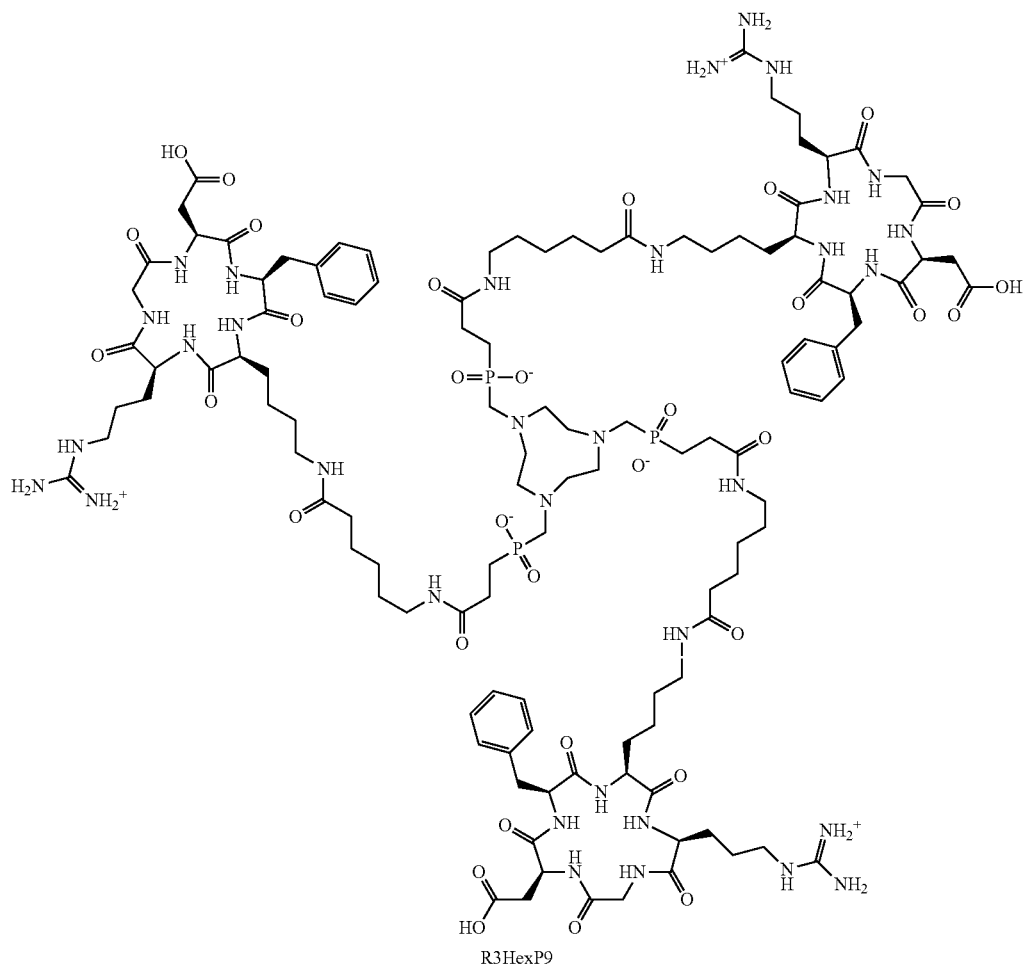

R3HexP9

General coupling protocol using HexP9 (16 mg) DMSO (0.7 ml), DIPEA (39 mg, 51 µl) cRGDfK(Pbf,tBu) (80 mg), HATU (46 mg). Reaction time: 10 min. $t_R$ (Gradient B): 11.4 min. Workup: Precipitation, followed by acidic deprotection. Purification by preparative HPLC (26% MeCN, $t_R$ ca. 15 min). Yield: 23 mg.

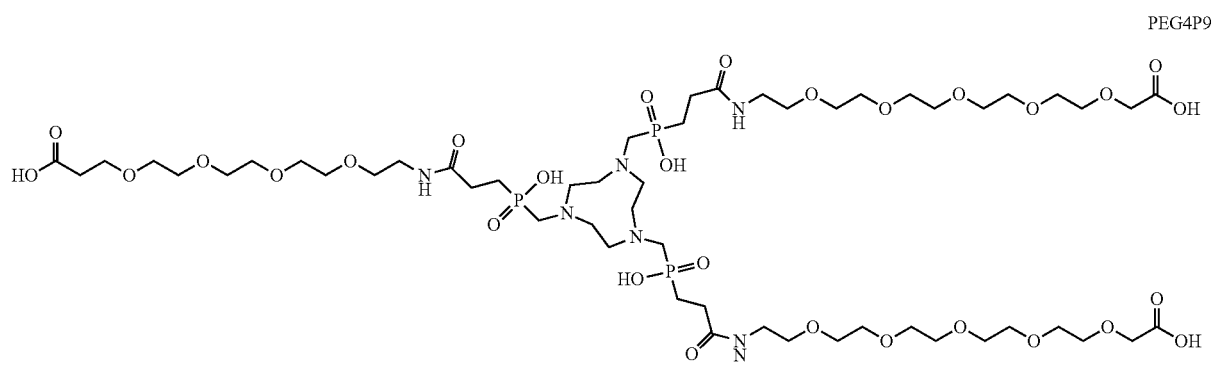

PEG4P9

General coupling protocol using PrP9 (246 mg), DIPEA (516 mg, 680 µl), DMSO (4 ml), H$_2$N-dPEG™ (4)-COOtBu (from Iris Biotech, Marktredwitz, Germany; 455 mg), HATU (1.22 g). Reaction time: 10 min. $t_R$ (Gradient A): 16 min. Workup: Ultrafiltration, followed by acidic deprotection. Purification by preparative HPLC (21% MeCN, $t_R$ ca. 12 min). Yield: 410 mg.

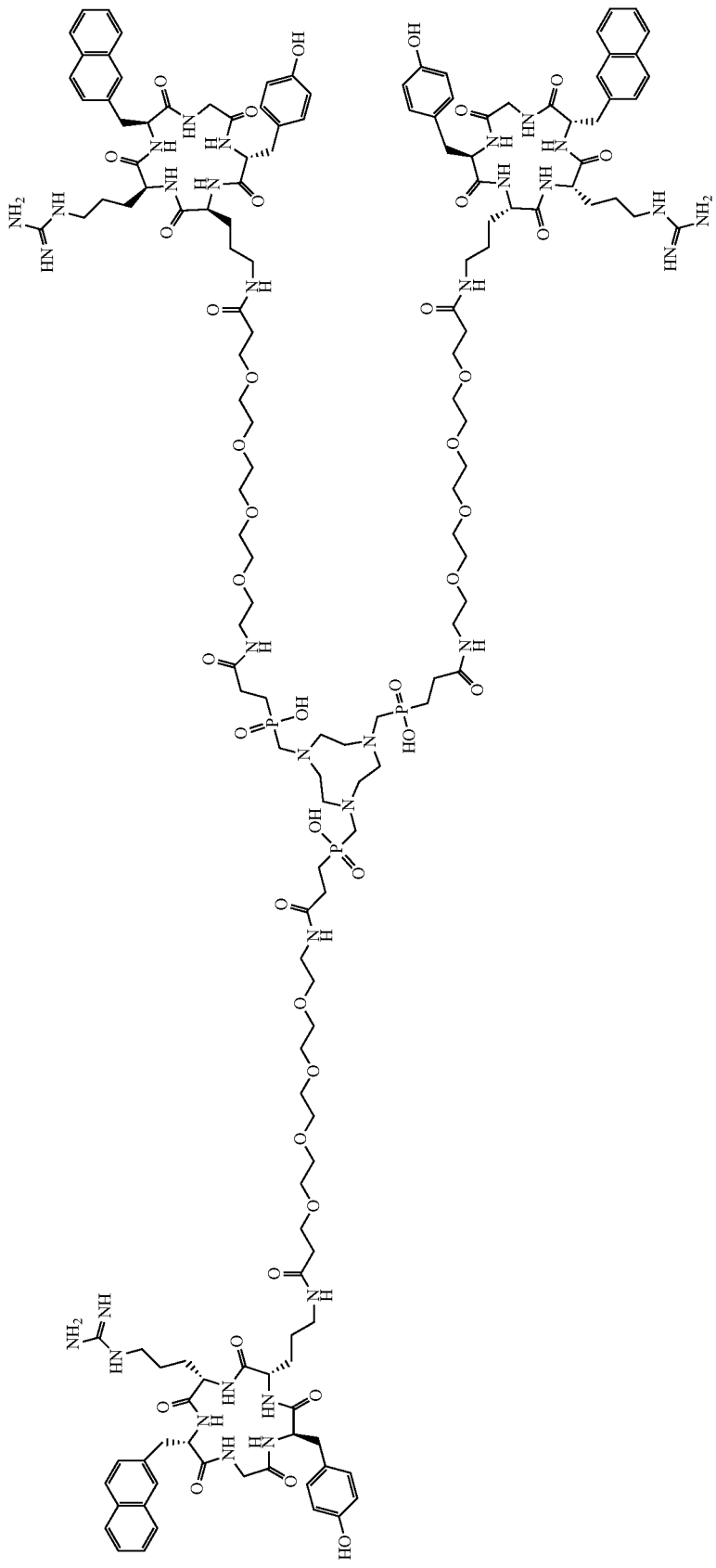

General coupling protocol using PEG4P9 (21 mg), DMSO (0.3 ml), DIPEA (36 mg, 48 μl), CPCR4 (50 mg), HATU (43 mg). Reaction time: 10 min. $t_R$ (Gradient A): 6.7 min. Purification: Precipitation, followed by preparative HPLC (46% MeCN, $t_R$ ca. 13 min). Yield: 23 mg.

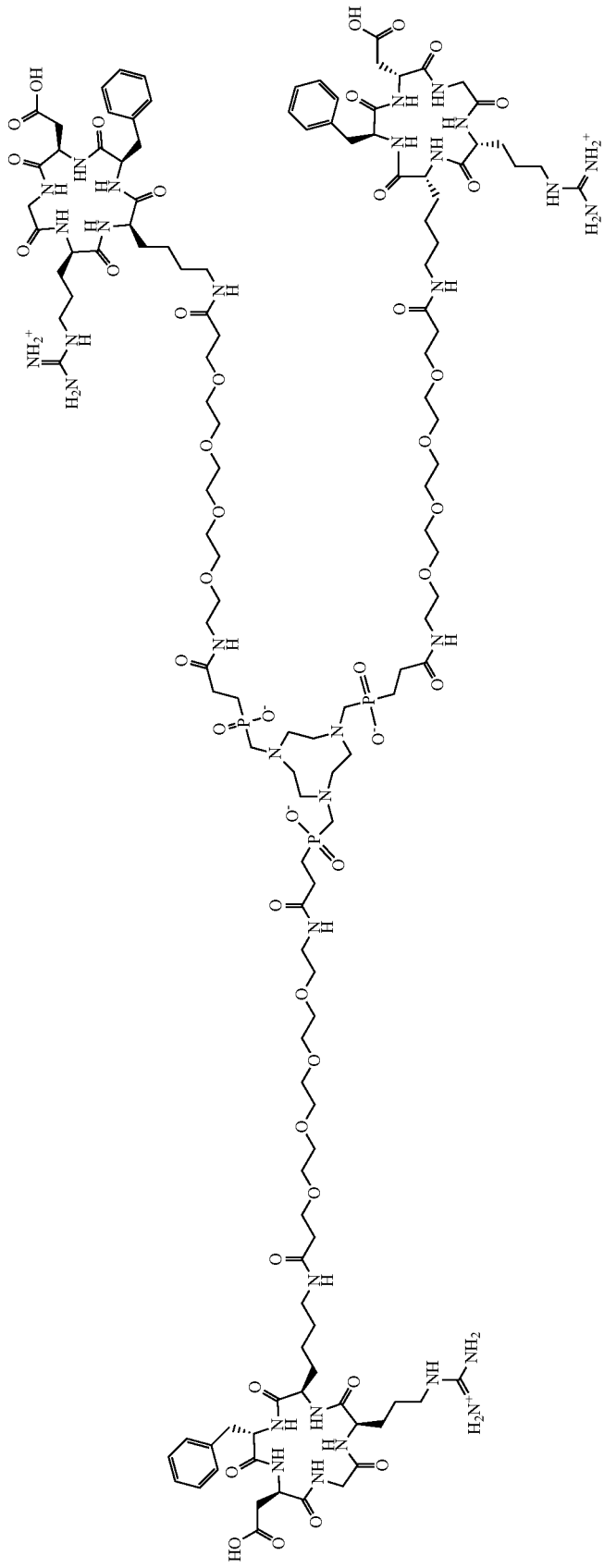

General coupling protocol using PEG4P9 (16 mg) DMSO (0.7 ml), DIPEA (31 mg, 41 µl) cDGRKf(Pbf,tBu) (60 mg), HATU (37 mg). Reaction time: 10 min. $t_R$ (Gradient B): 10.7 min. Workup: Precipitation, followed by acidic deprotection. Purification by preparative HPLC (25% MeCN, $t_R$ ca. 14 min). Yield: 11 mg.

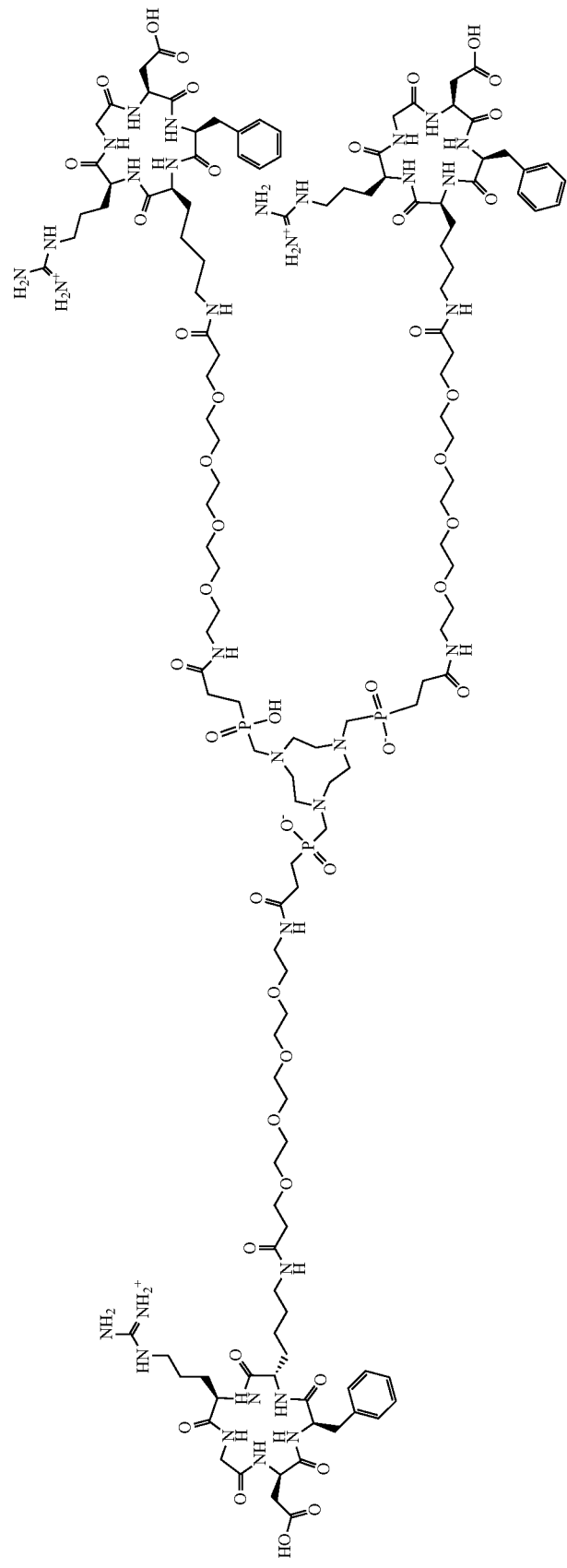

General coupling protocol using PEG4P9 (24 mg) DMSO (0.7 ml), DIPEA (39 mg, 51 µl) cRGDfK(Pbf,tBu) (80 mg), HATU (46 mg). Reaction time: 10 min. $t_R$ (Gradient B): 10.3 min. Workup: Precipitation, followed by acidic deprotection. Purification by preparative HPLC (27% MeCN, $t_R$ ca. 15 min). Yield: 28 mg.

PEG8P9

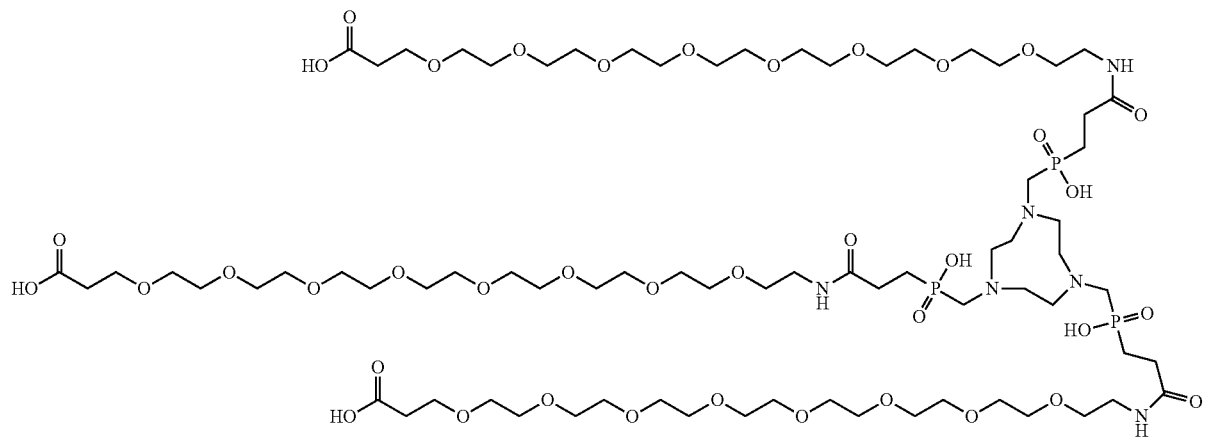

General coupling protocol using PrP9 (246 mg), DIPEA (516 mg, 680 µl), DMSO (4 ml), H$_2$N-dPEG™(8)-COOtBu (from Iris Biotech, Marktredwitz, Germany; 994 mg), HATU (1.22 g). Reaction time: 10 min. $t_R$ (Gradient A): 15 min. Workup: Ultrafiltration, followed by acidic deprotection. Purification by preparative HPLC (22% MeCN, $t_R$ ca. 12 min). Yield: 539 mg.

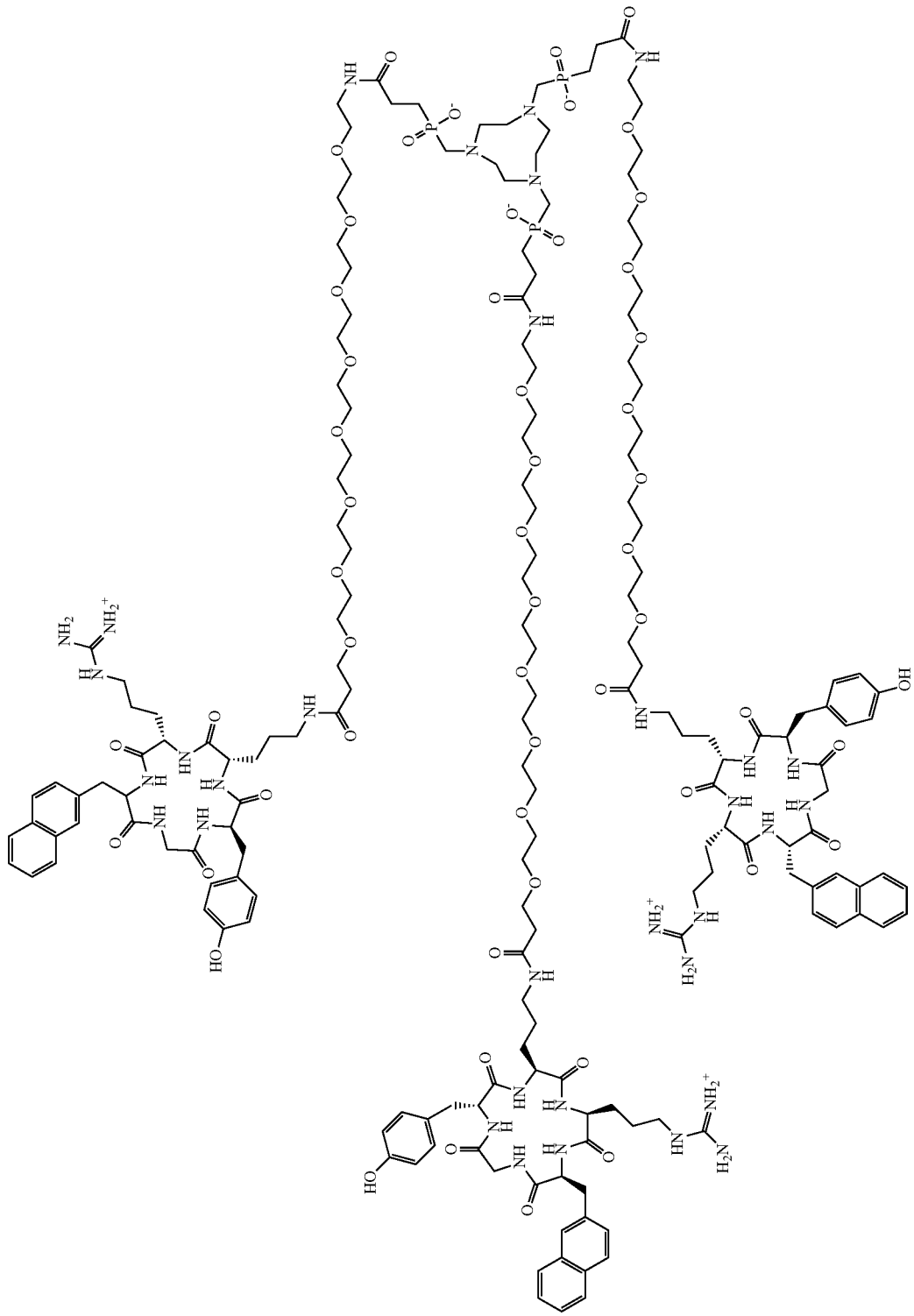

General coupling protocol using PEG8P9 (27 mg), DMSO (0.5 ml), DIPEA (36 mg, 48 µl), CPCR4 (50 mg), HATU (43 mg). Reaction time: 10 min. $t_R$ (Gradient A):

Purification: Precipitation, followed by preparative HPLC (49% MeCN, $t_R$ ca. 12 min). Yield: 18 mg.

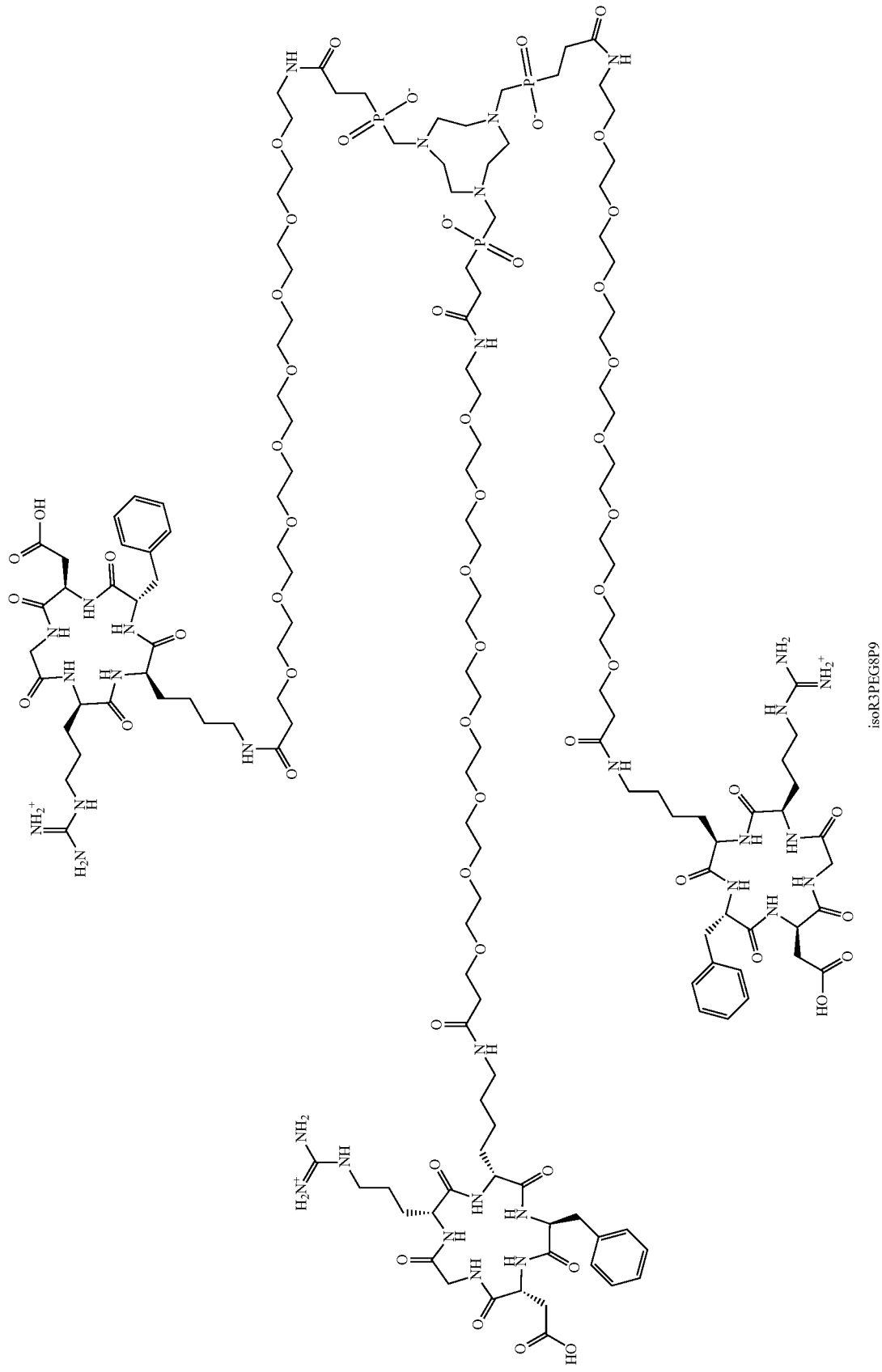

General coupling protocol using PEG8P9 (12 mg) DMSO (0.7 ml), DIPEA (15 mg, 20 μl) cDGRKf(Pbf,tBu) (30 mg), HATU (19 mg). Reaction time: 10 min. $t_R$ (Gradient B): 11.1 min. Workup: Precipitation, followed by acidic deprotection. Purification by preparative HPLC (31% MeCN, $t_R$ ca. 15 min). Yield: 7 mg.

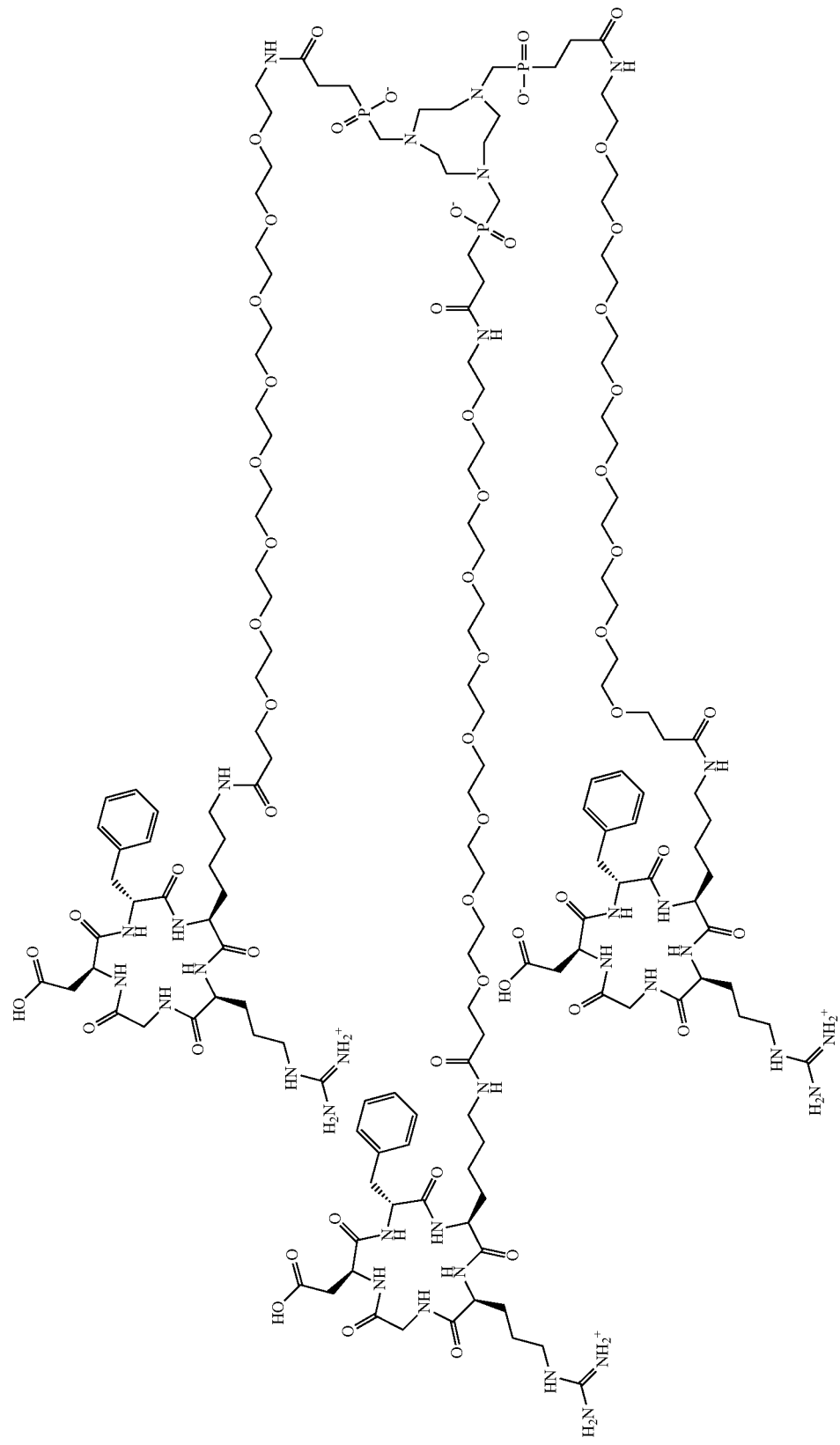

General coupling protocol using PEG8P9 (32 mg) DMSO (0.7 ml), DIPEA (41 mg, 54 μl) cRGDfK(Pbf,tBu) (80 mg), HATU (49 mg). Reaction time: 10 min. $t_R$ (Gradient B): 11.2 min.

Workup: Precipitation, followed by acidic deprotection. Purification by preparative HPLC (30% MeCN, $t_R$ ca. 16 min). Yield: 22 mg.

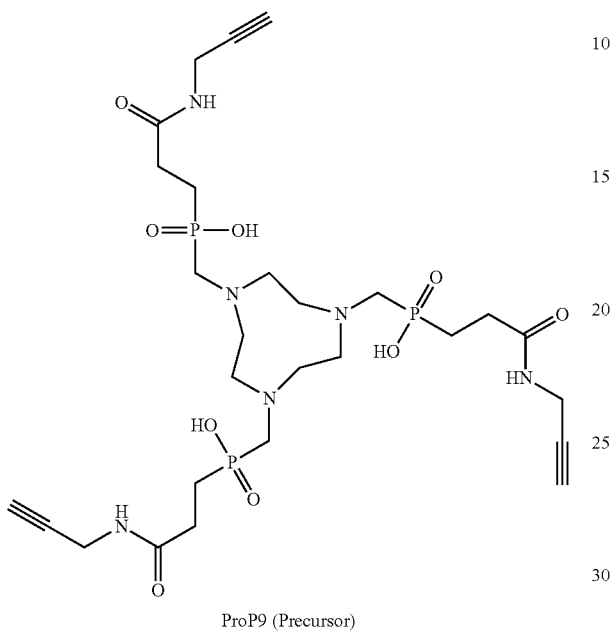

ProP9 (Precursor)

General coupling protocol using PrP9 (308 mg), DMSO (3 ml), DIPEA (645 mg, 850 μl), propargylamine (138 mg, 172 μl), HATU (1.5 g). Reaction time: 15 min. Workup: Ultrafiltration; no further purification necessary. Yield: 354 mg.

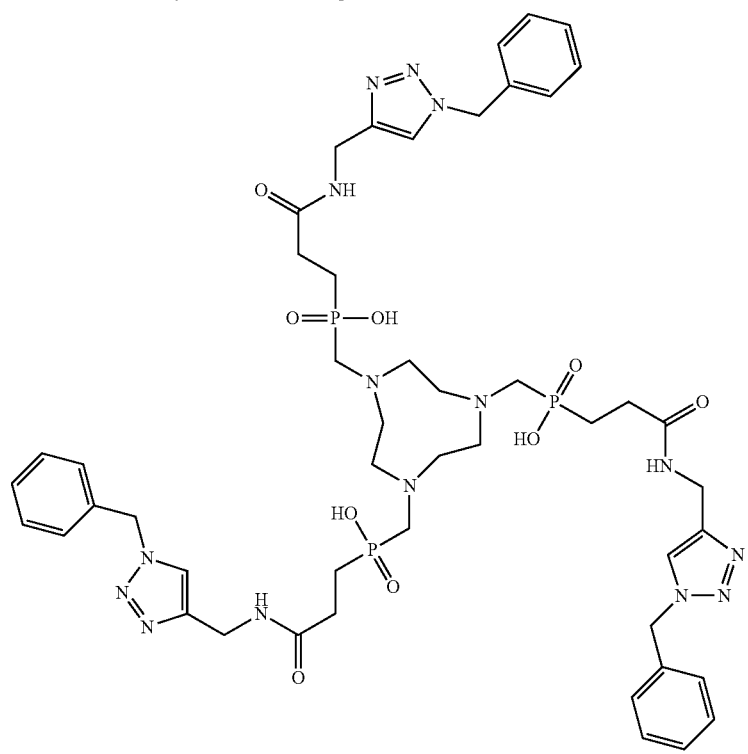

BnProP9 (model compound)

ProP9 (40 mg) and sodium ascorbate (100 mg) were dissolved in water (0.5 ml). Then a solution of benzyl azide (20 mg, 19 μl) in 0.5 ml MeOH was added. Upon addition of a solution of Cu(OAc)$_2$*H$_2$O (12 mg) in water (0.5 ml) a clear green reaction mixture was obtained. Purification was done by ultrafiltration. After concentration of the UF cell contents to 10 ml, solid Na$_2$S (50 mg) was added, whereupon a black precipitate was formed. Filtration over celite yielded a clear brown solution, presumably due to remaining colloidal sulfide precipitate. Purification was done by preparative HPLC. Yield: 25 mg.

ProP9 (12 mg) and sodium ascorbate (30 mg) were dissolved in methanol (0.2 ml). Then a solution of azido-cRGDfK(Pbf,tBu) (50 mg) in DMF (0.5 ml) was added. The mixture turned brown when a suspension of Cu(OAc)$_2$*H$_2$O (12 mg) in MeOH (0.5 ml) was added. After 70 min the product was precipitated by slow addition of the reaction mixture to 10 ml of brine, the precipitate separated by centrifugation and dried in vacuo. After acidic deprotection a light-green solid was obtained, which was dissolved in methanol/water mixture. Upon addition of sodium sulfide (50 mg) a brown precipitate was formed, which was filtered off. The filtrate was evaporated and the crude product purified by preparative HPLC (27% MeCN, t$_R$ ca. 11 min). Yield: 11 mg.

R3N3P9

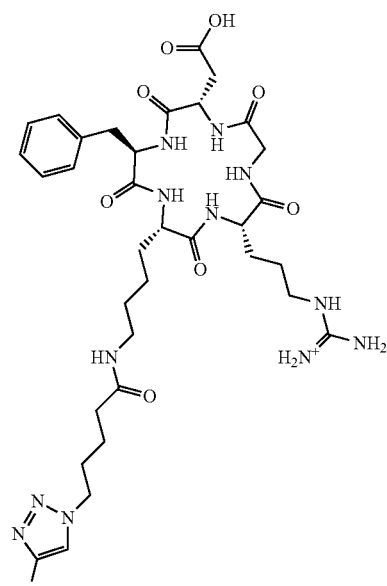

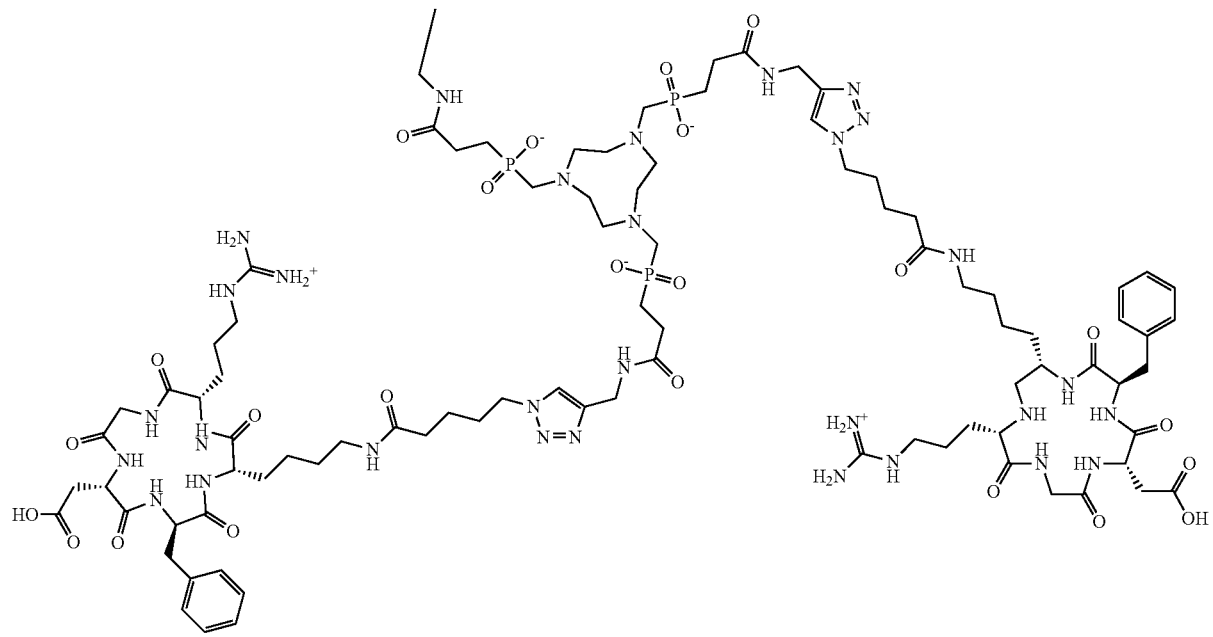

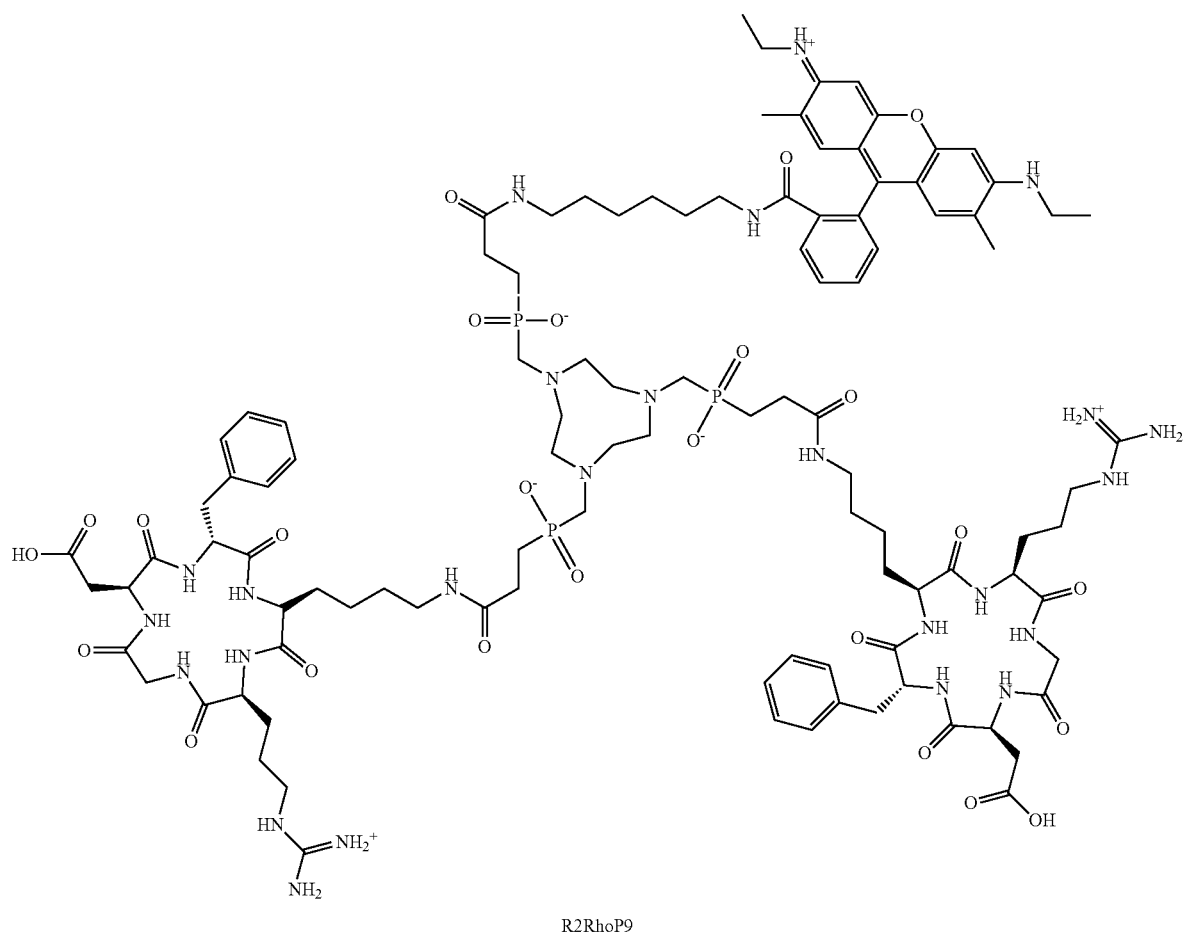

R2RhoP9

General coupling protocol using pR2P9 (15 mg), DMF (0.2 ml), DIPEA (8.5 mg, 11 μl) and aminohexyl-rhodamine-6G*2TFA (from Sigma, 10 mg) and HATU (13 mg). Reaction time: 10 min. $t_R$ (Gradient B): 19.5 min. Workup: Precipitation, followed by acidic deprotection. Purification by preparative HPLC (38% MeCN, $t_R$ ca. 18 min.). Yield: 10 mg.

$^{68}$Ga Labelling $^{68}$Ga-labelling was performed on an automated system (GaIIElute+ module from Scintomics, Fürstenfeldbruck, Germany), carrying out the following steps. $^{68}$Ga was obtained from a generator with $SnO_2$ matrix (manufactured by IThembaLABS, South Africa, distributed by IDB Holland) which was eluted with 1.0 M HCl.

The precursor (e.g. R3PEG4P9, different molar amounts) was placed in a 4 ml conical reaction vial (AllTech), together with a solution of 260 mg 2-(4-(2-Hydroxyethyl)-1-piperazinyl)-ethansulfonsäure (HEPES) in 220 μl Wasser. Then a 1.25 ml fraction of the generator eluate, containing the hightest activity (between 500 and 600 MBq) was added, resulting in a pH of 1.8. The vial was heated to 100° C. for 5 min. Then the reaction mixture was passed over a SPE cartridge (Waters SepPak Classic C18), the cartridge purged with 10 ml of water to remove free $^{68}Ga^{3+}$, inorganic ions and HEPES, and purged with air. The product was eluted with 2 ml of a 1:1 mixture of ethanol and water and the cartridge and lines purged with 1 ml of water. For animal experiments, 1 ml of PBS (pH 7.4) was added and the solution concentrated in vacuo to 1 ml, thus removing all ethanol and producing a formulation suitable for injection.

For comparison purposes, the labeling of DOTATOC and NODAGA-RGD was carried out in exactly the same way as described above, only using 600 mg HEPES in 500 ml water to achieve a labelling pH of 3.2-3.3 which is ideal for these compounds.

Log P Determination

Octanol-water partition coefficients were determined by addition of ca. 50 kBq of the respective labelled compound to Eppendorf cup containing each 500 μl of 1-octanol and isotonic phosphate buffered saline (PBS). After 2 min of vigorous stirring, the phases were separated by centrifugation, 100 μl aliquots of each phase taken out and the activity contained determined with a gamma counter. Each experiment was repeated 5-8 times.

In Vitro Binding Assay

Binding assays were done for all RGD conjugates, their natGa complexes, and also for echistatin and 19F-galacto-RGD to act as standards.

Determination of integrin receptor affinity was carried out using M21 human melanoma cells, possessing high $\alpha_v\beta_3$ expression. Experiments were carried out in 24-well plates. Ca. $2\times10^5$ cells were seeded into wells containing RPMI 1640 media and incubated for 24 h at 37° C. and 5% $CO_2$. Then the medium was exchanged with 0.5 ml, binding buffer (20 mmol/l Tris, pH 7.4, 150 mmol/l NaCl, 2 mmol/l $CaCl_2*2H_2O$, 1 mmol/l $MgCl_2*6H_2O$, 1 mmol/l $MnCl_2*4H_2O$, 0.1% (m/m) BSA), containing 30.000-50.000 cpm $^{125}$I-echistatin and the respective RGD peptide conjugate in increasing concentrations from $10^{-11}$-$10^{-4}$ M. After incubation at room temperature for 2 h, the supernatant is removed, the cells washed twice with PBS, lysed with 1 M NaOH (1 ml) and the lysates counted for 60 s in a gamma counter. Experiments were performed at minimum three times in duplicates and $IC_{50}$ values calculated using Graph-Pad prism for sigmoidal (dose-response) regression analysis.

In the table below, logarithmic $IC_{50}$ values with logarithmic errors, corresponding $IC_{50}$ values, and log P values for the standard, all RGD conjugates and their Ga(III)-complexes are given (see Synthesis section).

| Compound | log $IC_{50}$ | $IC_{50}$ (nM) | logP |
|---|---|---|---|
| Echistatin | −9.01 ± 0.033 | 0.98 | — |
| 19F-Galacto-RGD | −6.45 ± 0.157 | 319 | — |
| R3PEG4P9 | −7.37 ± 0.053 | 43 | — |
| Ga-R3PEG4P9 | −7.36 ± 0.049 | 44 | −3.90 ± 0.10 |
| R3PEG8P9 | −7.30 ± 0.029 | 50 | — |
| Ga-R3PEG8P9 | −7.13 ± 0.034 | 74 | −4.13 ± 0.16 |
| R3GlutP9 | −6.90 ± 0.069 | 125 | — |
| Ga-R3GlutP9 | −6.66 ± 0.068 | 220 | −4.03 ± 0.12 |
| R3HexP9 | −7.07 ± 0.075 | 85 | — |
| Ga-R3HexP9 | −7.25 ± 0.080 | 56 | −3.99 ± 0.13 |
| R1P9 | −5.53 ± 0.047 | 2890 | — |
| Ga-R1P9 | −5.64 ± 0.058 | 2270 | −3.91 ± 0.11 |
| R2P9 | −6.43 ± 0.128 | 370 | — |
| Ga-R2P9 | −6.29 ± 0.107 | 512 | −4.12 ± 0.06 |
| R2RhoP9 | −7.04 ± 0.031 | 92 | — |
| Ga-R2RhoP9 | −7.11 ± 0.043 | 78 | −1.27 ± 0.04 |

Biodistribution of $^{68}$Ga-R3PEG4P9

Biodistribution studies were performed using CD-1 athymic nude mice bearing human melanoma xenografts on both shoulders (right: M21 cell line with high $\alpha_v\beta_3$ integrin xexpression, left: M21L cell line with low $\alpha_v\beta_3$ integrin expression). The mice were injected 6-9 MBq of $^{68}$Ga-R3PEG4P9 (specific activity: ca. 900 GBq/μmol, corresponding to approx. 7-10 pmol of the tracer). After the specified time points (60 and 120 min, respectively), the mice were sacrificed, the organs taken out and counted in a gamma counter. For blockade, the mice were administered 200 μg (approx. 10 mg/kg) of unlabeled R3PEG4P9 10 min before tracer injection.

The table shows uptake values (given as percent injected dose per gram tissue) 60 and 120 min after tracer injection, as well as 60 min after injection with blockade. Data is visualized in the chart (FIG. 3).

| | % ID/g | % ID/g time | % ID/g |
|---|---|---|---|
| | 60 min | 120 min | 60 min, blocked |
| | | number of animals | |
| | 5 | 5 | 3 |
| blood | 0.31 | 0.16 | 0.09 |
| heart | 1.29 | 1.47 | 0.08 |
| lung | 2.96 | 2.15 | 0.54 |
| liver | 5.18 | 3.97 | 0.32 |
| spleen | 3.38 | 3.50 | 0.24 |
| pancreas | 0.88 | 0.81 | 0.07 |
| stomach | 4.43 | 3.56 | 0.17 |
| small int. | 4.92 | 3.75 | 0.24 |
| large int. | 2.44 | 2.27 | 0.11 |
| kidneys | 10.16 | 8.63 | 1.97 |
| adrenal gland | 27.77 | 24.17 | 0.36 |
| muscle | 0.95 | 0.67 | 0.05 |
| thyroid | 3.27 | 2.89 | 0.17 |
| tumor M21L | 1.48 | 1.70 | 0.31 |
| tumor M21 | 6.08 | 4.63 | 0.62 |

Metabolite Studies for $^{68}$Ga-R3PEG4P9

Metabolite studies were performed using mice similar as used for biodistribution. The mice were anaesthesized with isoflurane and injected 30-40 MBq of $^{68}$Ga-R3PEG4P9 (specific activities between 1200-3200 MBq/nmol, injected molar amounts ranging from 9-18 pmol). After 30 min the animals were sacrificed, the blood was collected in a heparine syringe and centrifuged. The respective organs were removed, frozen with liquid nitrogen and homogenized by means of a ball mill. The resulting powder was suspended in 0.5-1 mL of PBS, together with 30 μg of R3PEG4P9, stirred for 1 min, and centrifuged. For both organs and blood, the supernatant (plasma, respectively) was separated, both the pellet and supernatant counted in a gamma-counter in order to determine extraction efficiency or blood cell binding. Supernatants, plasma and urine were subjected to ultrafiltration (30 kDa MWCO) and analyzed by radio-HPLC (Merck chromolith column 100×4.6 mm; flux rate 2 ml/min; eluents: A, water with 0.1% TFA, B, acetonitrile with 0.1% TFA; isocratic elution for 2 min with 3% B, followed by gradient from 3-60% B in 6 min and purging with 95% B for 3 min). For determination of adrenal gland/pancreas/spleen metabolites, organs of three animals were pooled.

The table shows extraction efficiencies for the tissues worked up with the above described procedure; * the fraction of the blood activity in the plasma after centrifugation is given.

| tissue | extraction efficiency* |
|---|---|
| kidney | 92% |
| tumor M21 | 92% |
| liver | 81% |
| spleen/pancreas | 88% |
| adrenal gland | 95% |
| blood plasma | 96% |

In FIG. 4, HPLC chromatograms of $^{68}$Ga-R3PEG4P9 (for reference) and the analyzed extracts are shown, indicating that no metabolites could be detected.

PET Imaging

Preclinical imaging was done with mice similar as used for biodistribution. The mice were anaesthesized with isoflurane, placed in the PET camera, and 13-14 MBq of $^{68}$Ga-R3PEG4P9 (without blockade and with prior injection of 100 μg of unlabelled R3PEG4P9) or $^{68}$Ga-isoR3PEG4P9 were administered via tail vein injection. The calculated molar amount of labelled tracer per injection was ca. 20 pmol with a calculated minimum specific activity of ca. 900 GBq/μmol. PET scans were recorded dynamically for 90 min.

The graphic (FIG. 5) shows PET images derived from data measured 60-90 min after injection (maximum intensity projections; left: R3PEG4P9, center: R3PEG4P9 with blockade, right: isoR3PEG4P9).

The charts (FIG. 6) show distribution kinetics derived from PET data.

The invention also refers to the following items:

(1) Chelate ligands according to general formula (II)

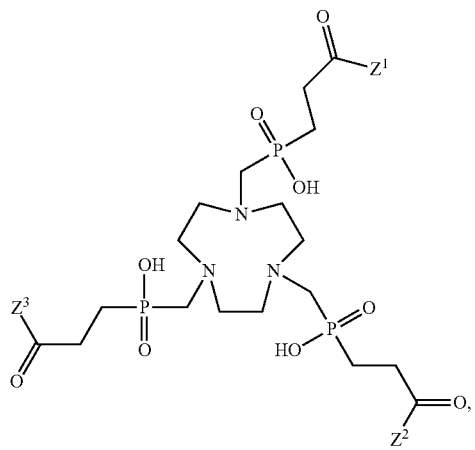

(II)

wherein
$Z^1$ is OH or $NR^1R^4$,
$Z^2$ is OH or $NR^2R^5$,
$Z^3$ is OH or $NR^3R^6$, $R^1$, $R^2$, $R^3$ is independently of another selected from the group consisting of linear or cyclic, substituted or unsubstituted, aliphatic, heteroaliphatic, aromatic, heteroaromatic, saturated or unsaturated radicals, wherein said $R^1$, $R^2$ and/or $R^3$ is optionally attached to the core molecule via at least one linking group, $R^4$, $R^5$, $R^6$ is independently of another selected from the group consisting of hydrogen, linear or cyclic, substituted or unsubstituted, aliphatic, heteroaliphatic, aromatic, heteroaromatic, saturated or unsaturated radicals, wherein at least one of $Z^1$, $Z^2$ and $Z^3$ is different from OH.

(2) Chelate ligand according to item 1 wherein, $R^4$, $R^5$ and $R^6$ are hydrogen.

(3) Chelate ligand according to item 1, wherein $R^1$, $R^2$ and $R^3$ are independently of another based on amines being selected from the group consisting of cyclic, aliphatic amines, amino acids esters, amino acid esters, biotin, aliphatic phosphonates, peptides, proteins, residues thereof, antibodies, antibody fragments and engineered antibody formats, anticalines, biomolecules that bind with high affinity (low nM affinity) to other proteins, receptors, transporters of other molecular targets in vivo and in vitro, biomolecules, fluorophores and mixtures thereof.

(4) Chelate ligand according to any of items 1 to 3 having one of the following formulae

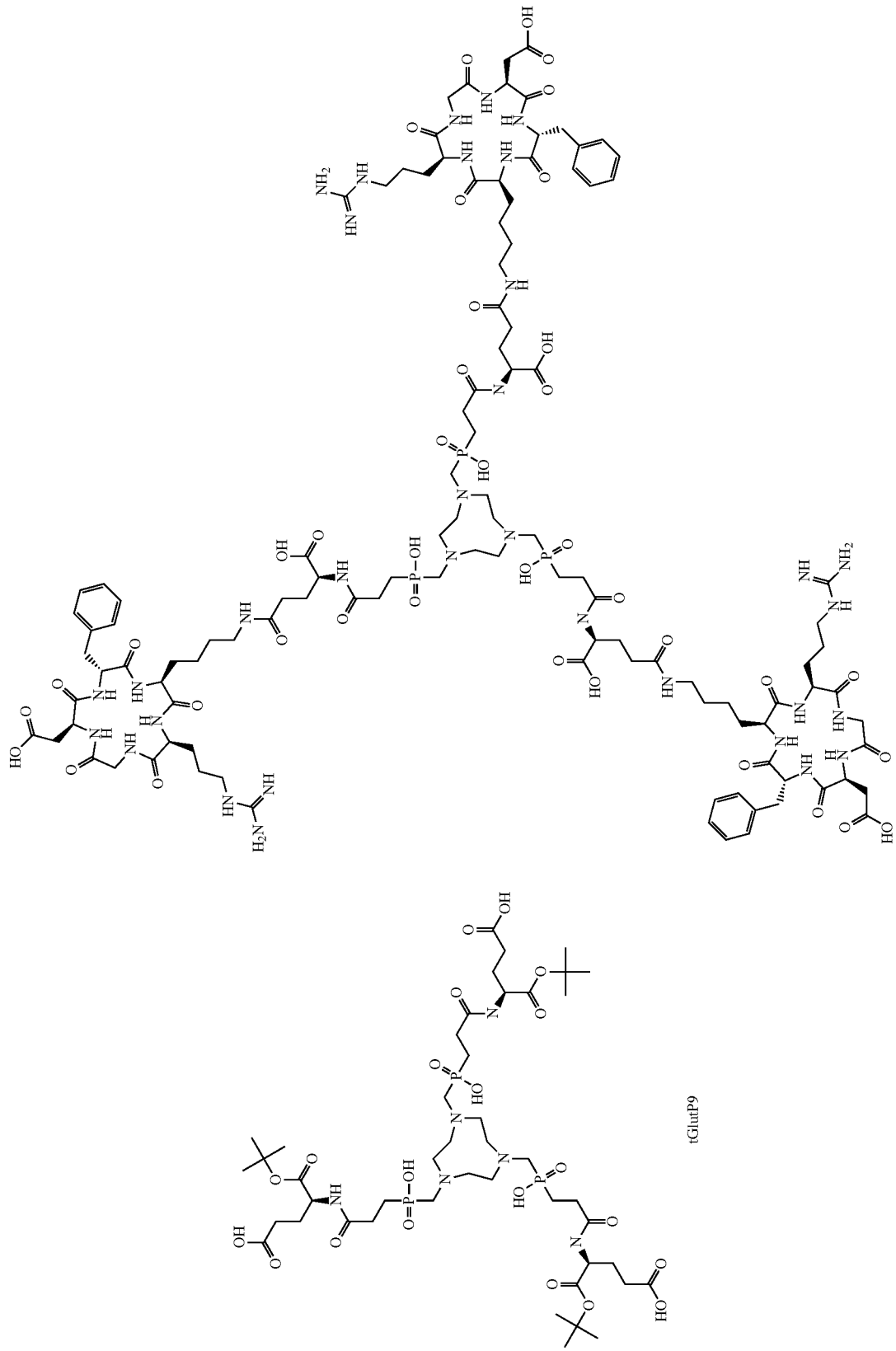

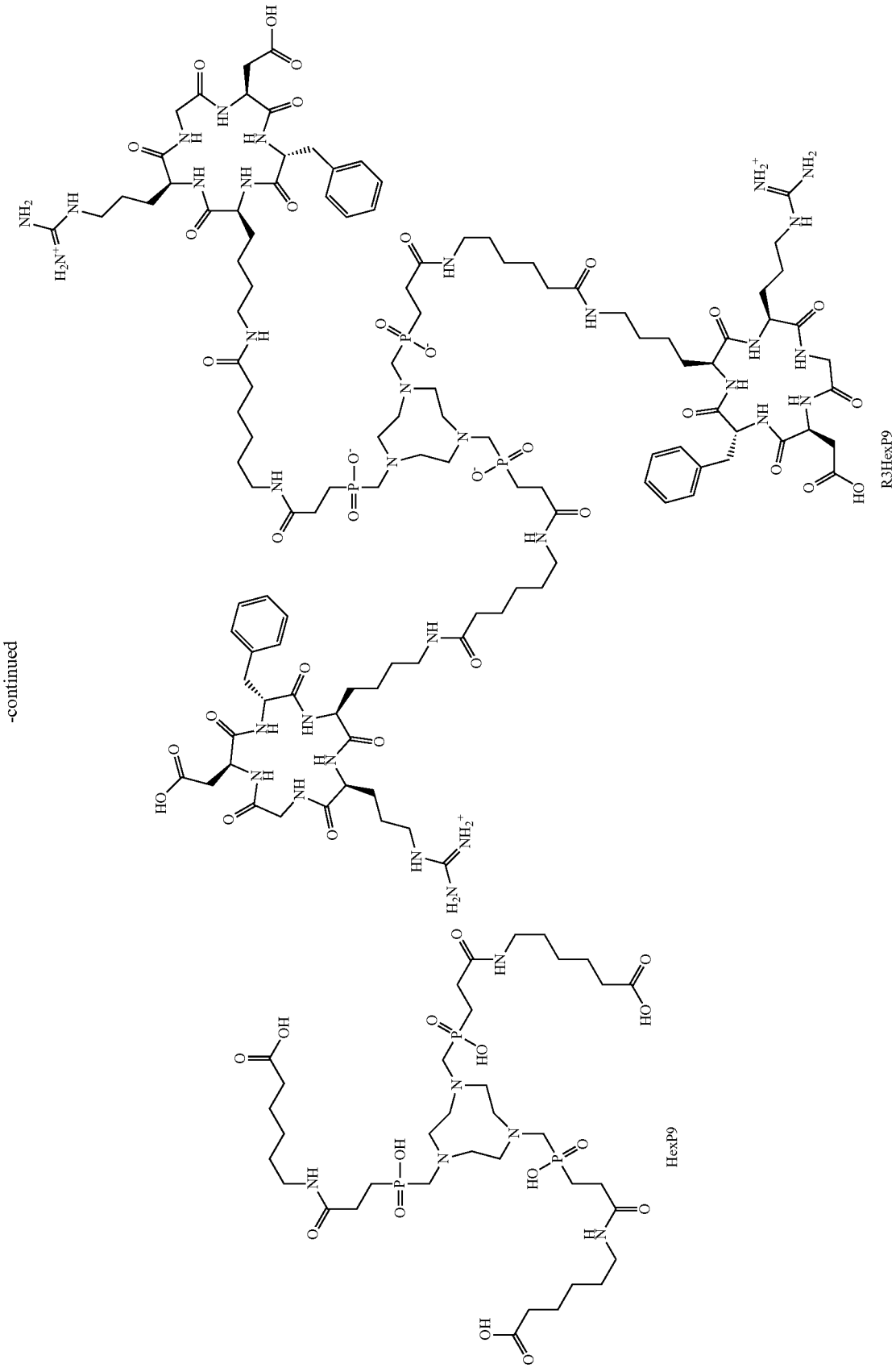

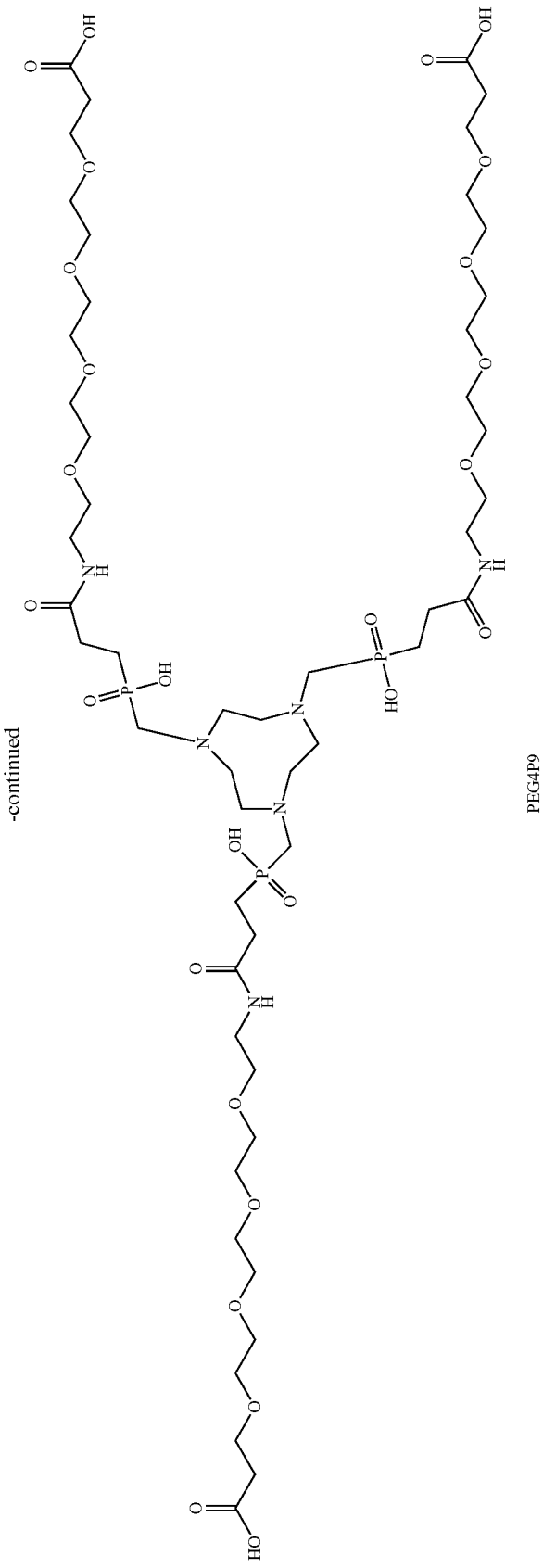
PEG4P9

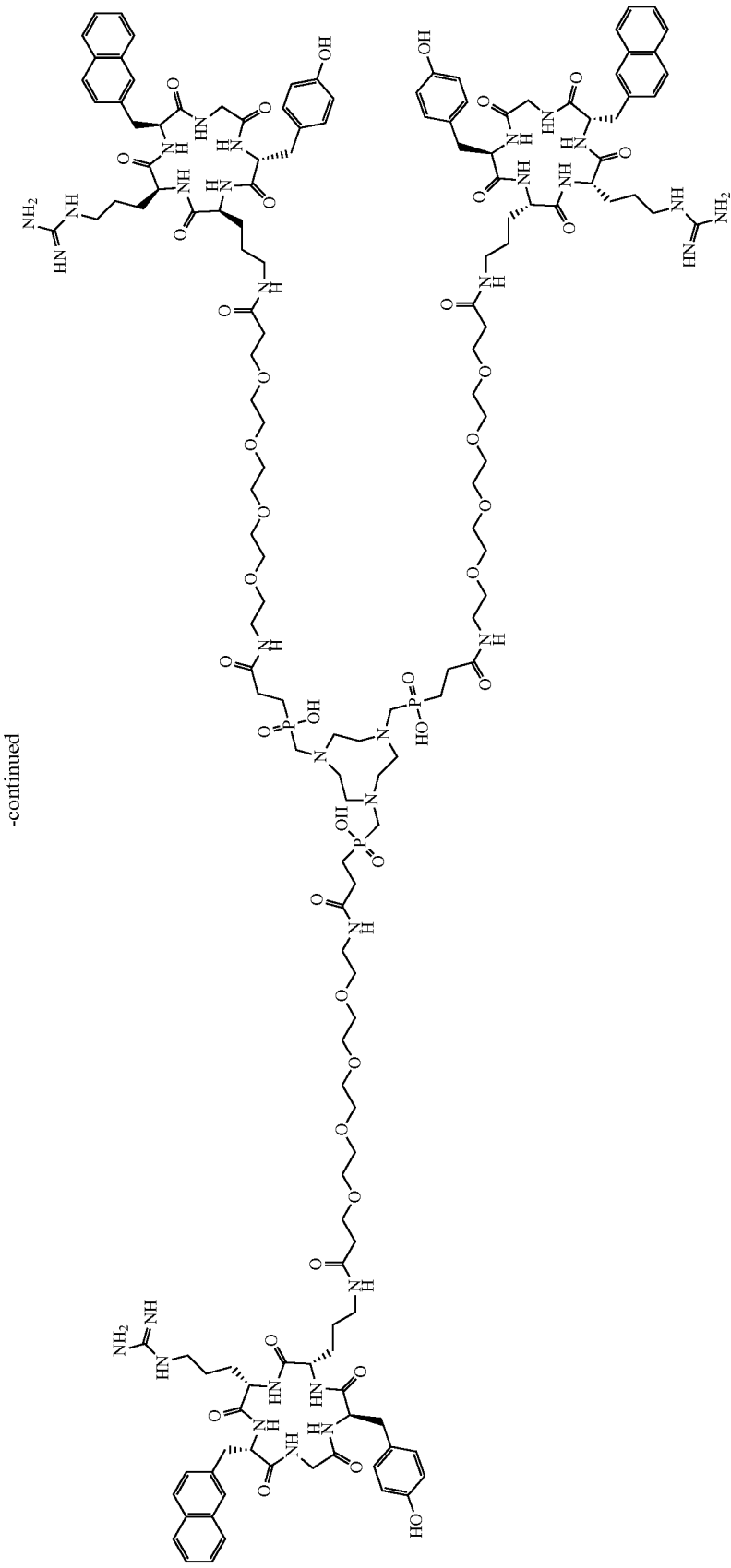
C3PEG4P9

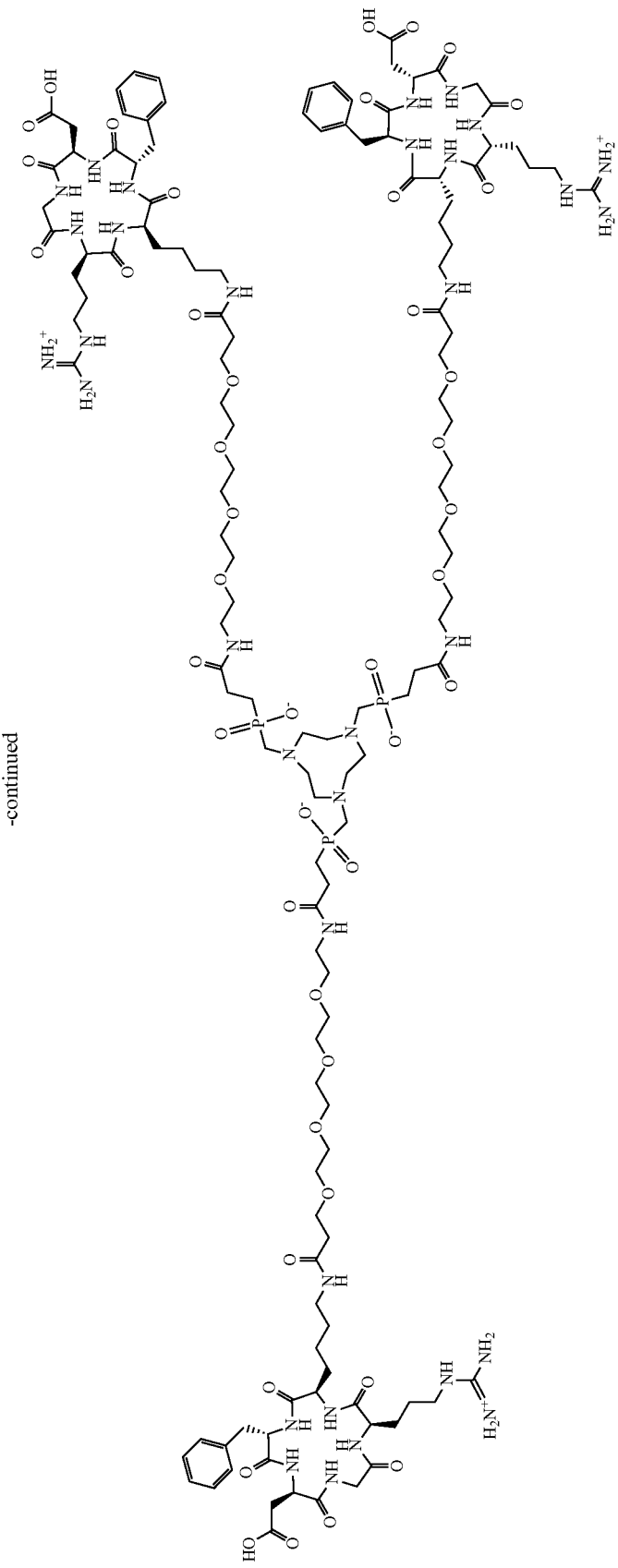

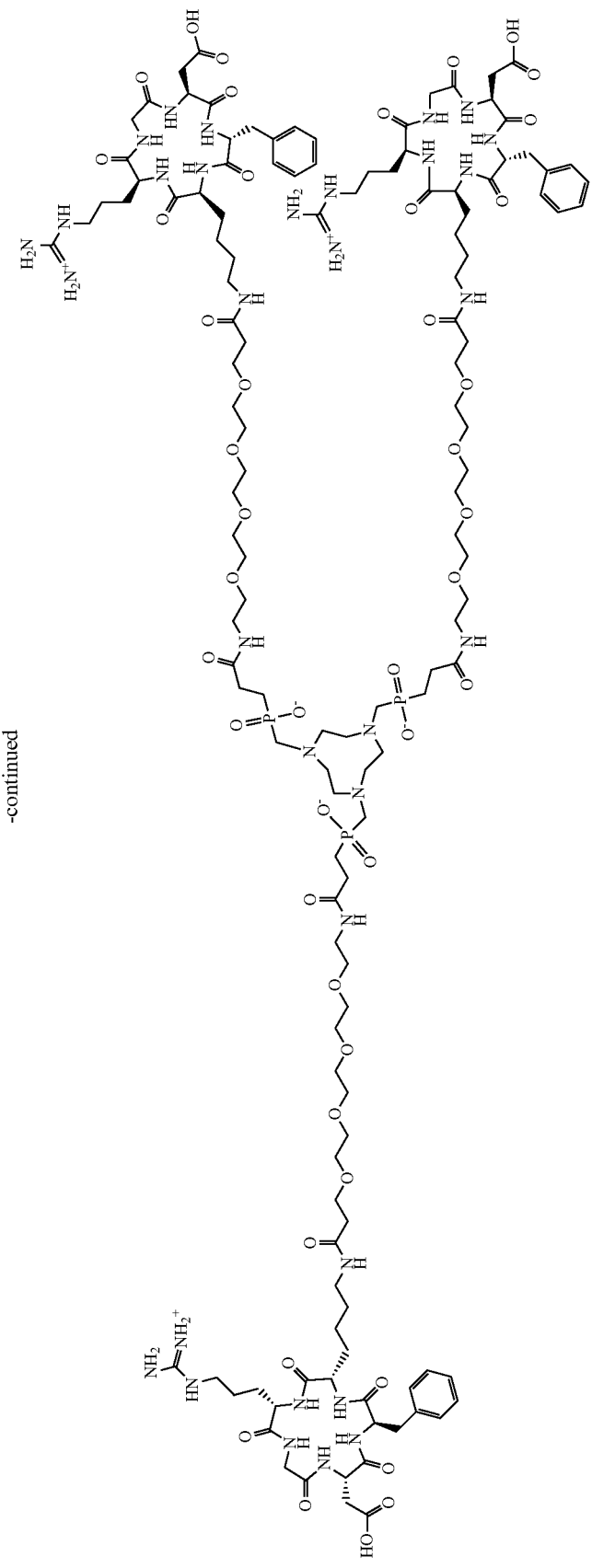
R3PEG4P9

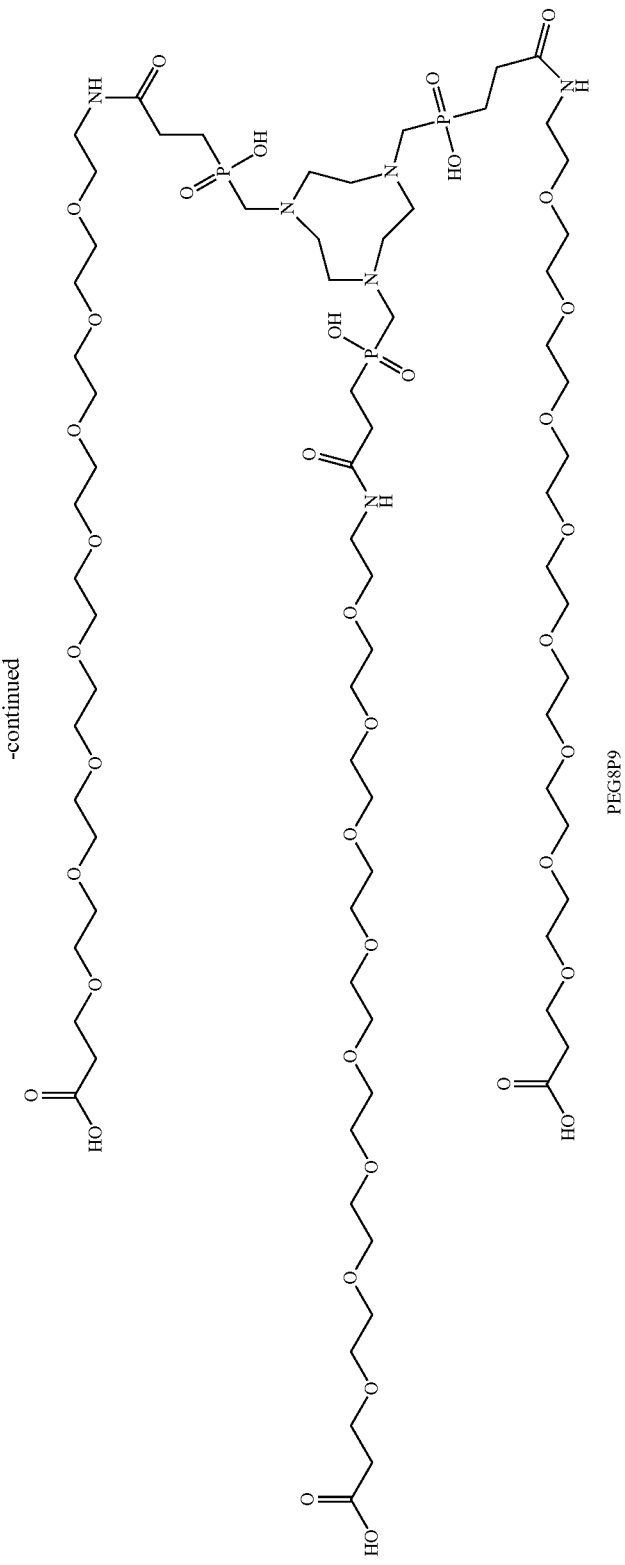

-continued
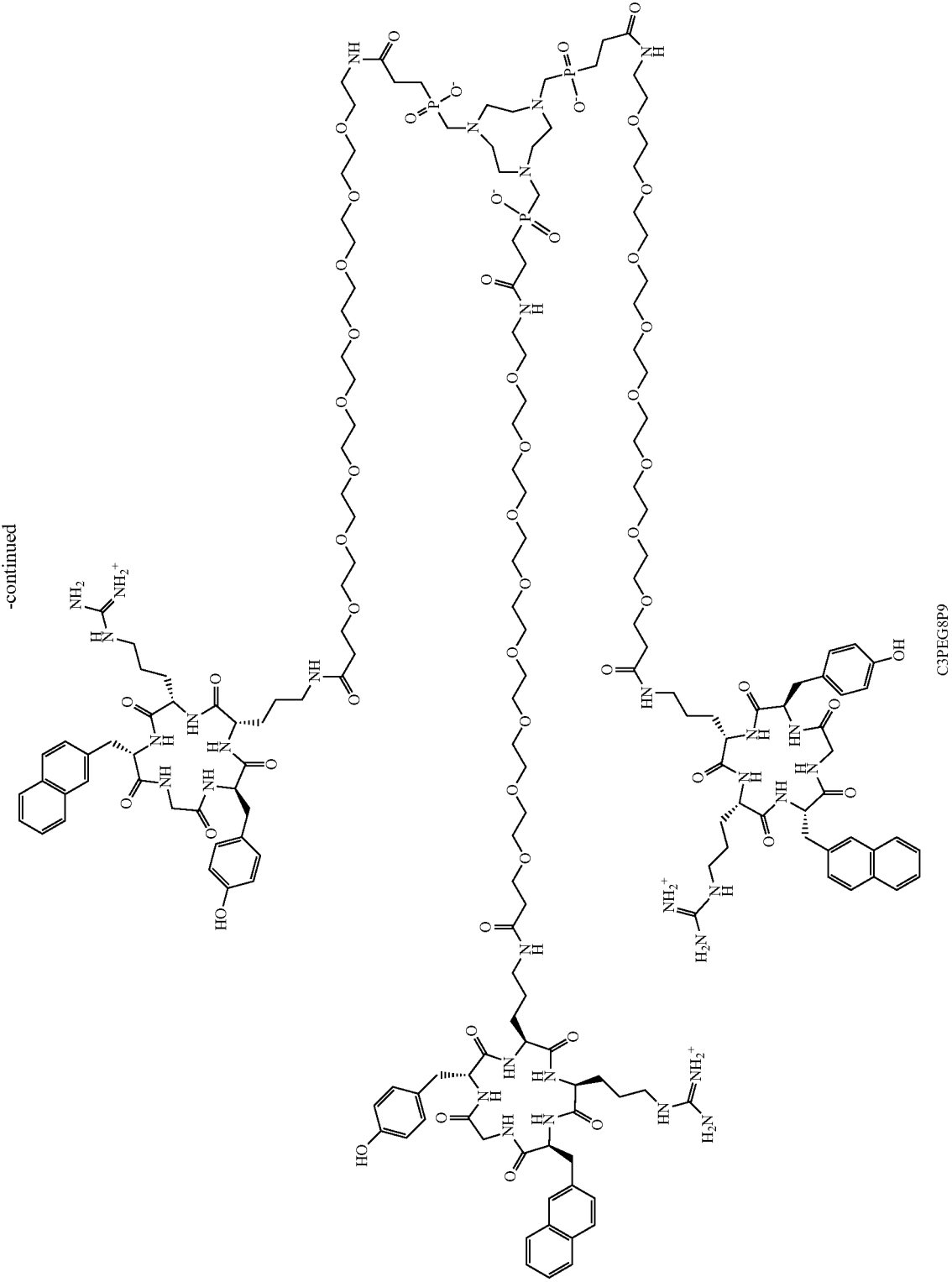
C3PEG8P9

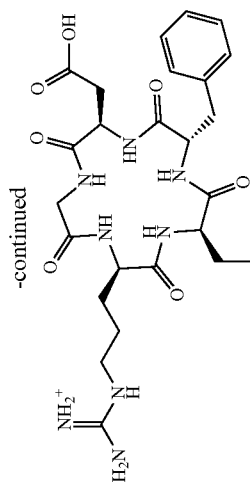
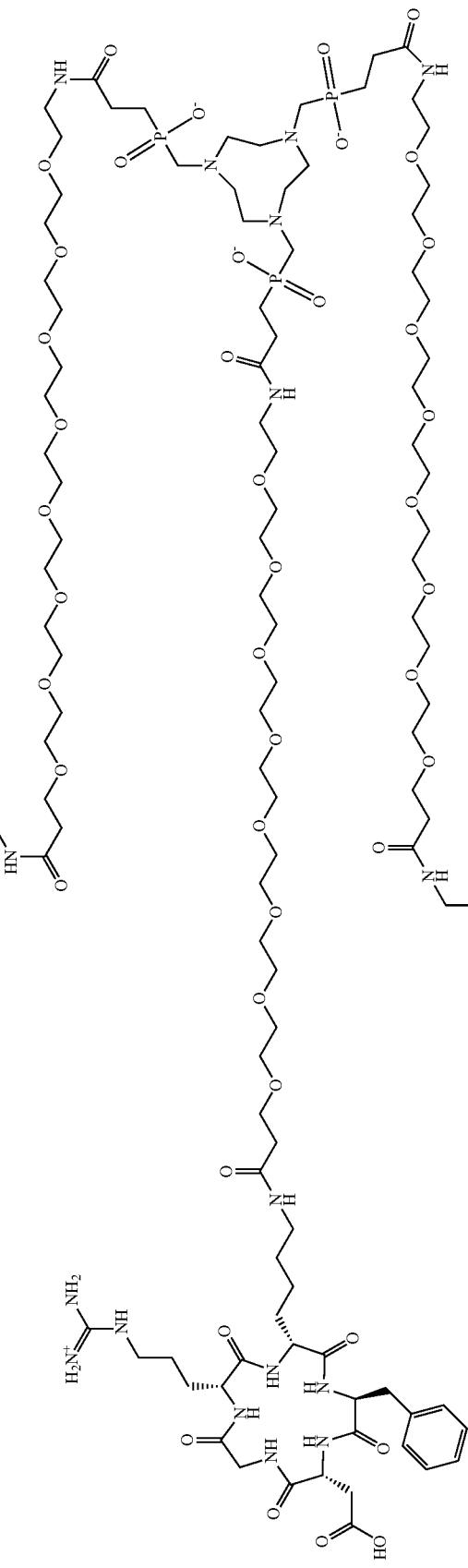
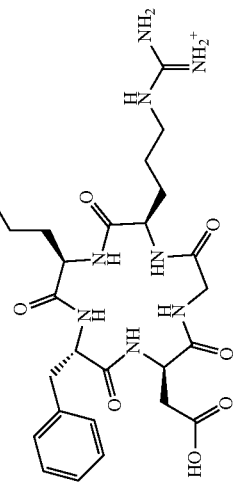

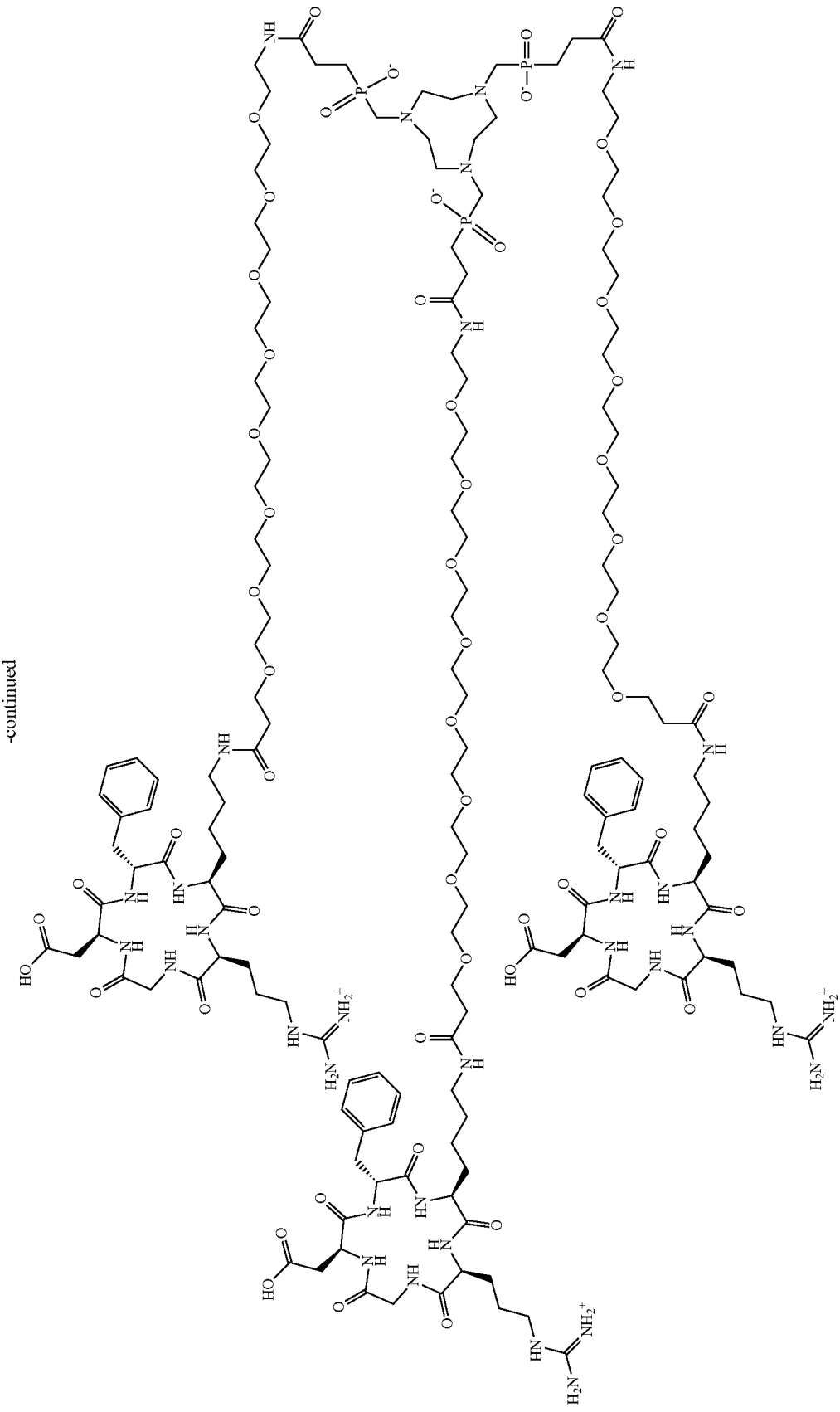

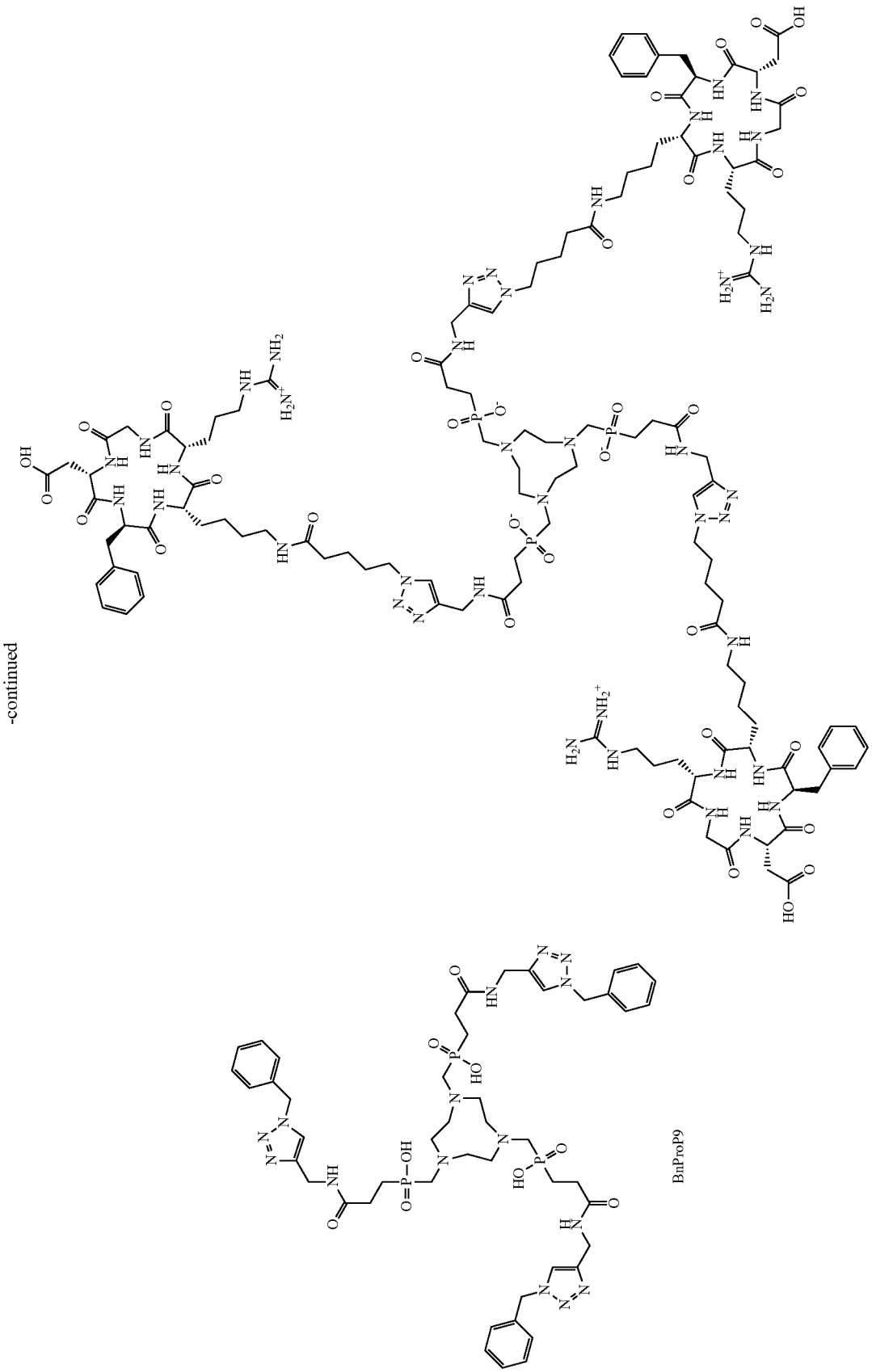

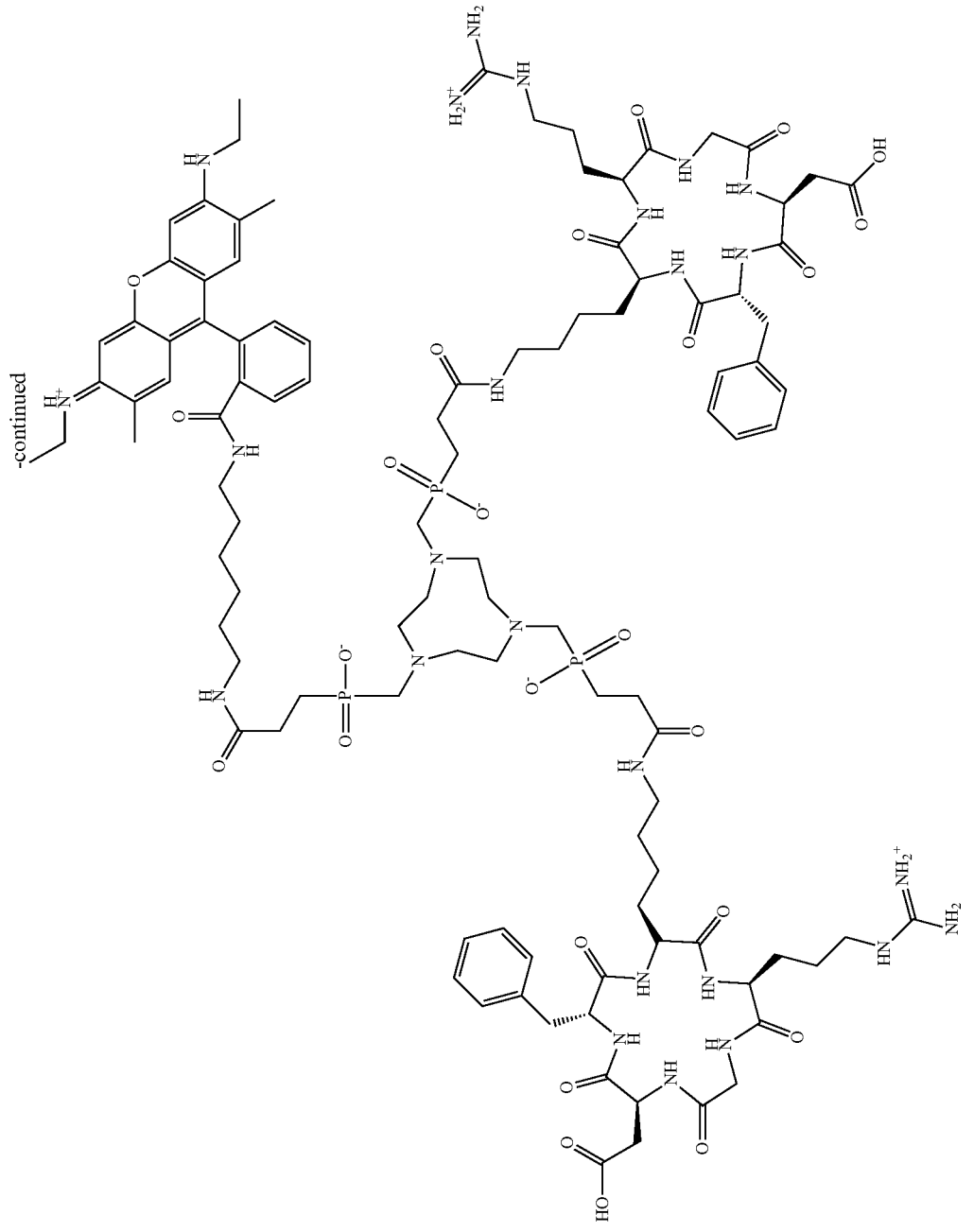
R2RhoP9

(5) Process for the preparation of chelate ligands according to any of items 1 to 4 by reaction of chelate ligands of formula (I)

(I)

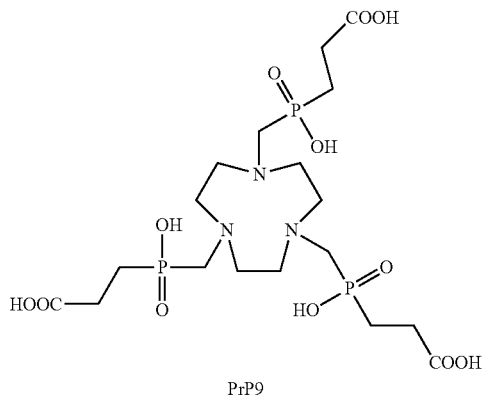

PrP9 with $R^1R^4NH$, $R^2R^5NH$, $R^3R^6NH$, wherein $R^1$, $R^2$, $R^3$, $R^4$, $R^5$, $R^6$ have the same meanings as defined in any of items 1 to 4.

(6) Chelate comprising at least one chelate ligand according to general formula (II) as defined in any of items 1 to 4 and at least one metal or radiometal.

(7) Chelate according to item 6, wherein the at least one metal or radiometal is selected from the group consisting of $La^{3+}$, $Ce^{3+}$, $Pr^{3+}$, $Nd^{3+}$, $Sm^{3+}$, $Eu^{2+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, $Sc^{3+}$, $Y^{3+}$, $Al^{3+}$, $Ga^{3+}$, $Ge^{4+}$, $In^{3+}$, $As^{3+}$, $Sn^{2+}$, $Sn^{4+}$, $Sc^{3+}$, $Ti^{4+}$, $V^{5+}$, $Cr^{3+}$, $Mn^{2+}$, $Fe^{3+}$, $Co^{2+}$, $Co^{3+}$, $Ni^{2+}$, $Cu^{1+}$, $Cu^{2+}$, $Zn^{2+}$, $Cd^{2+}$ and mixtures thereof.

(8) Chelate according to item 6 or 7, wherein the at least one radiometal is selected from the group consisting of $^{44}Sc$, $^{46}Sc$, $^{55}Co$, $^{99m}Tc$, $^{203}Pb$, $^{66}Ga$, $^{67}Ga$, $^{68}Ga$, $^{72}As$, $^{111}In$, $^{113m}In$, $^{114m}In$, $^{97}RU$, $^{62}Cu$ $^{64}Cu$, $^{52}Fe$, $^{52m}Mn$, $^{51}Cr$, $^{186}Re$, $^{188}Re$, $^{77}As$, $^{90}Y$, $^{67}Cu$, $^{169}Er$, $^{117m}Sn$, $^{121}Sn$, $^{127}Te$, $^{142}Pr$, $^{143}Pr$, $^{198}Au$, $^{199}Au$, $^{149}Tb$, $^{161}Tb$, $^{109}Pd$, $^{65}Dy$, $^{149}Pm$, $^{151}Pm$, $^{153}Sm$, $^{157}Gd$, $^{66}Ho$, $^{172}Tm$, $^{169}Yb$, $^{176}Yb$, $^{177}Lu$, $^{105}Rh$, $^{111}Ag$ and mixtures thereof, preferably selected from the group consisting of $^{44}Sc$, $^{99m}Tc$, $^{67}Ga$, $^{68}Ga$, $^{111}In$, $^{64}Cu$, $^{188}Re$, $^{90}Y$, $^{177}Lu$ and mixtures thereof.

(9) Process for the preparation of a chelate according to item 6, wherein at least one residue $R^1$, $R^2$, $R^3$ according to general formula (II) and the PrP9 core is labelled with at least one metal or radiometal.

(10) Process according to item 9, wherein the at least one metal or radiometal is selected from the group consisting of $La^{3+}$, $Ce^{3+}$, $Pr^{3+}$, $Nd^{3+}$, $Sm^{3+}$, $Eu^{2+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, $Sc^{3+}$, $Y^{3+}$, $Al^{3+}$, $Ga^{3+}$, $Ge^{4+}$, $In^{3+}$, $As^{3+}$, $Sn^{2+}$, $Sn^{4+}$, $Sc^{3+}$, $Ti^{4+}$, $V^{5+}$, $Cr^{3+}$, $Mn^{2+}$, $Fe^{3+}$, $Co^{2+}$, $Co^{3+}$, $Ni^{2+}$, $Cu^{1+}$, $Cu^{2+}$, $Zn^{2+}$, $Cd^{2+}$ and mixtures thereof.

(11) Process according to item 9 or 10, wherein the at least one radiometal is selected from the group consisting of $^{44}Sc$, $^{46}Sc$, $^{55}Co$, $^{99m}Tc$, $^{203}Pb$, $^{66}Ga$, $^{67}Ga$, $^{68}Ga$, $^{72}As$, $^{111}In$, $^{113m}In$, $^{114m}In$, $^{97}Ru$, $^{62}Cu$, $^{64}Cu$, $^{52}Fe$, $^{52m}Mn$, $^{51}Cr$, $^{186}Re$, $^{188}Re$, $^{77}As$, $^{90}Y$, $^{67}Cu$, $^{169}Er$, $^{117m}Sn$, $^{121}Sn$, $^{127}Te$, $^{142}Pr$, $^{143}Pr$, $^{198}Au$, $^{199}Au$, $^{49}Tb$, $^{161}Tb$, $^{109}Pd$, $^{165}Dy$, $^{49}Pm$, $^{151}Pm$, $^{153}Sm$, $^{157}Gd$, $^{66}Ho$, $^{172}Tm$, $^{169}Yb$, $^{175}Yb$, $^{177}Lu$, $^{105}Rh$, $^{111}Ag$ and mixtures thereof, preferably selected from the group consisting of $^{44}Sc$, $^{99m}Tc$, $^{67}Ga$, $^{68}Ga$, $^{111}In$, $^{64}Cu$, $^{188}Re$, $^{90}Y$, $^{177}Lu$ and mixtures thereof.

(12) Method of using chelate ligands according to any of items 1 to 4 or chelates according to any of items 6 to 8 in molecular imaging.

(13) The method according to item 12, wherein molecular imaging is multimodal molecular imaging.

The invention claimed is:
1. A chelate ligand having one of the following formulae

R3GlutP9

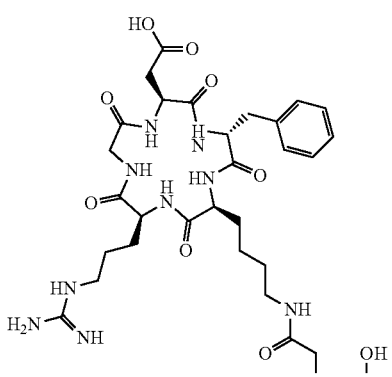

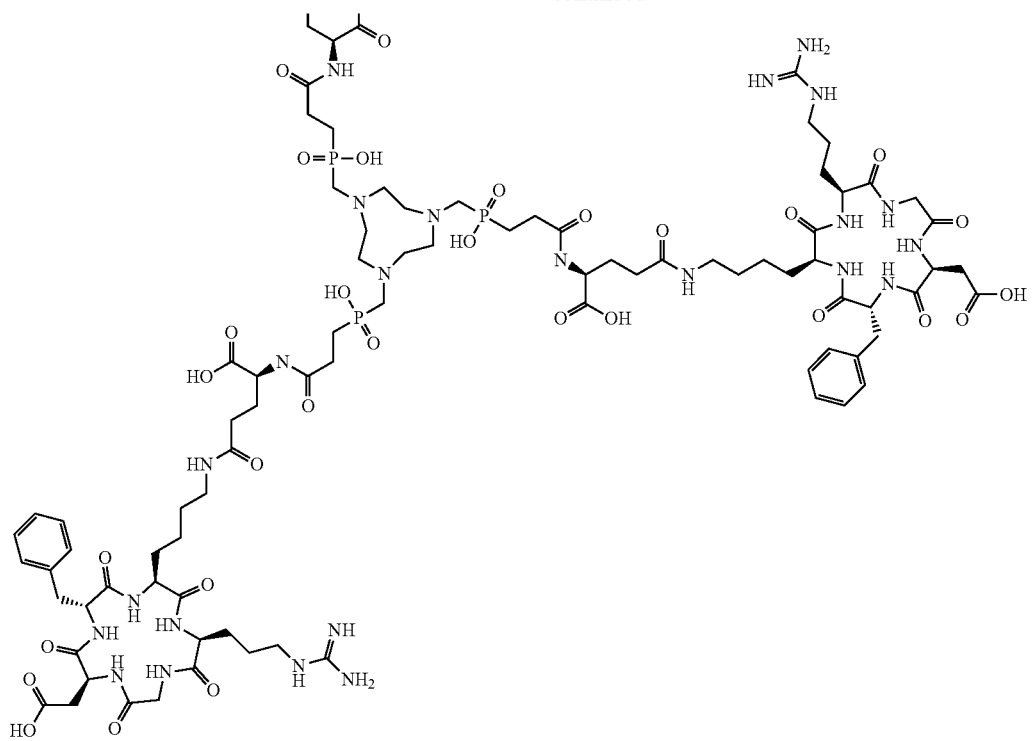

113 114
-continued
R3HexP9
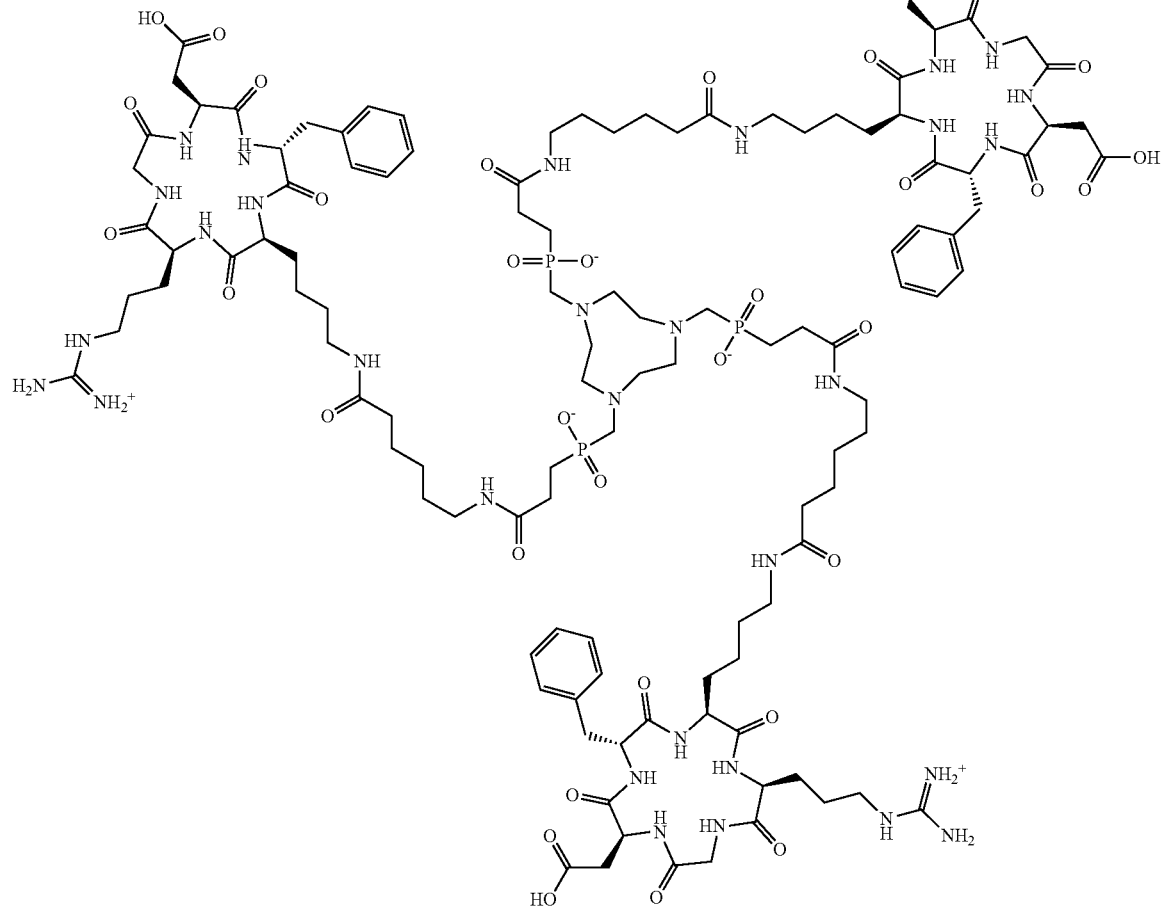
isoR3PEG4P9
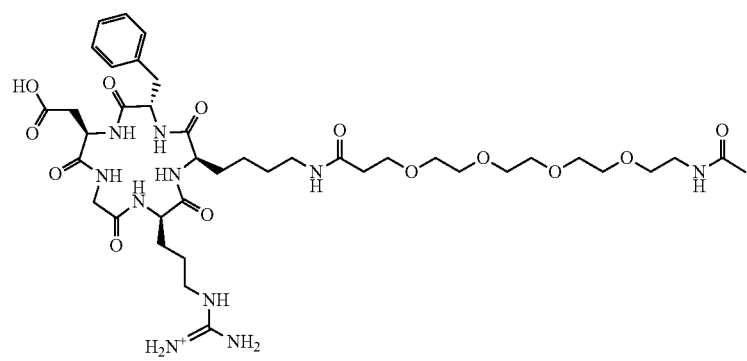

-continued
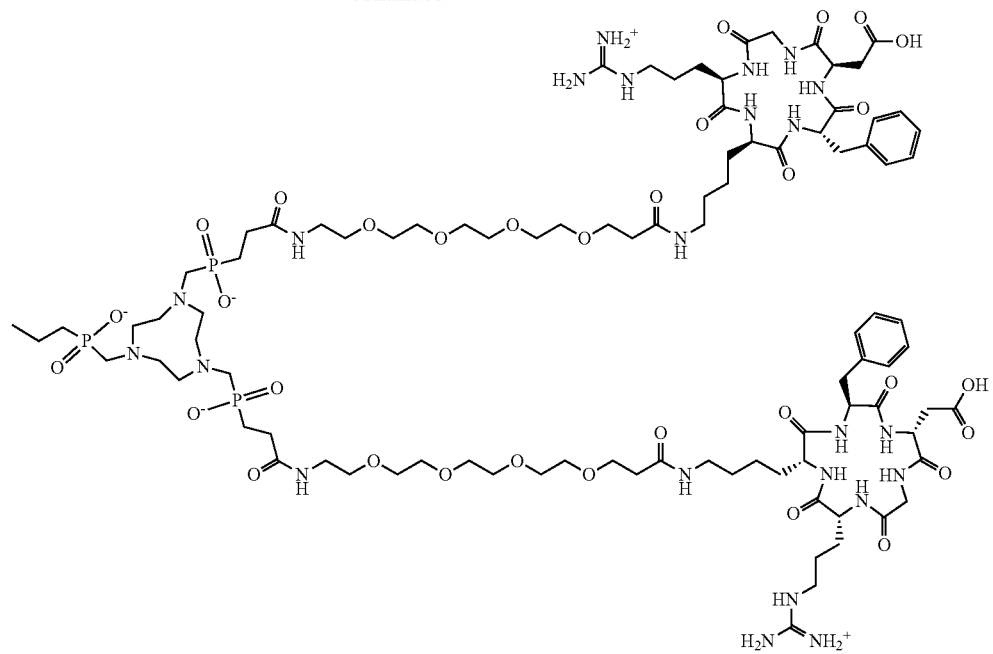
R3PEG4P9
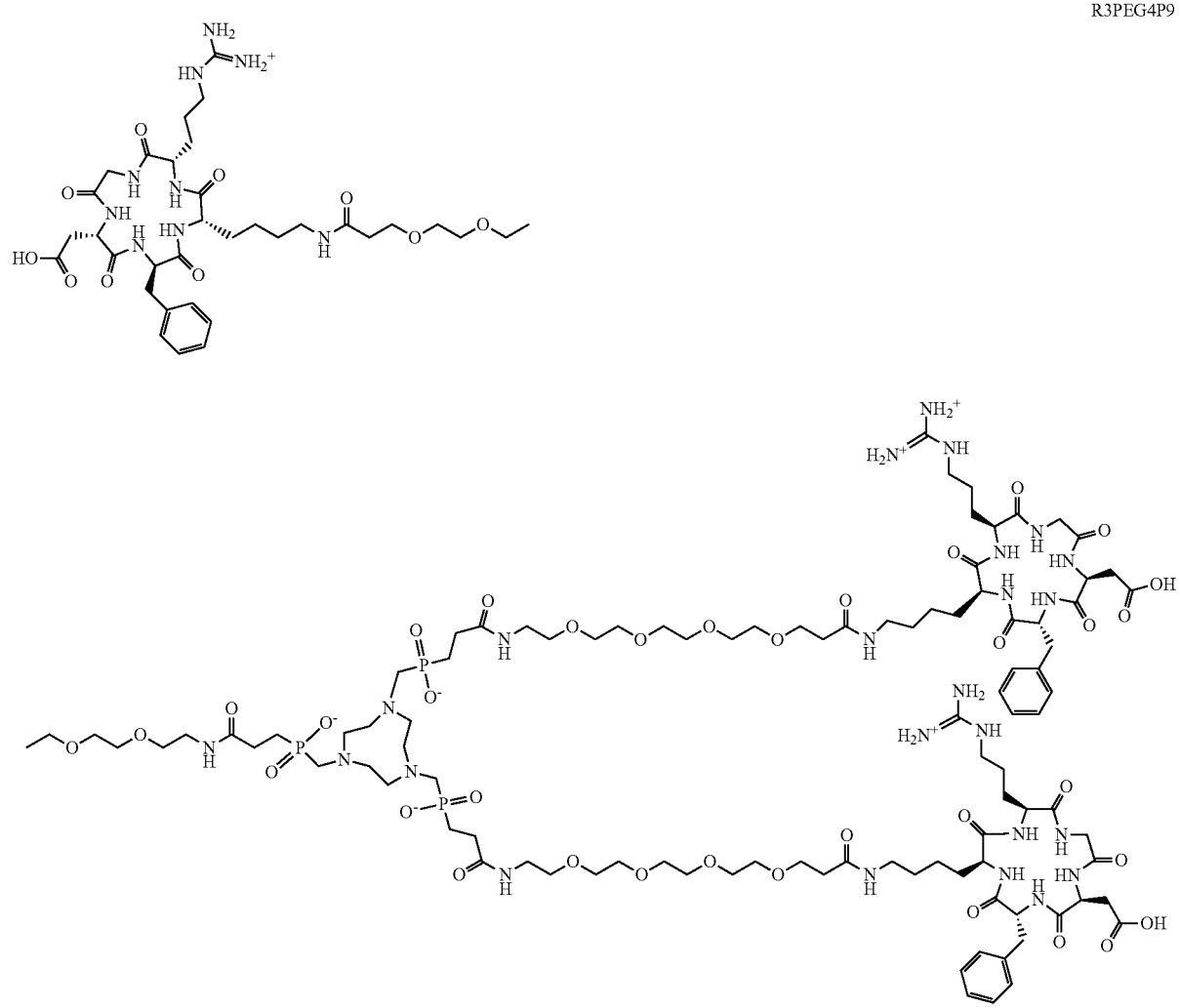

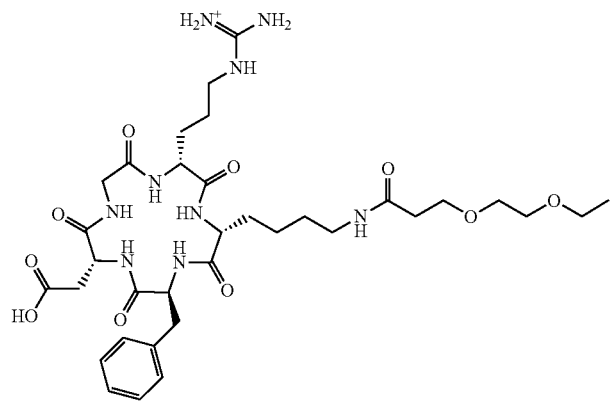
isoR3PEG8P9
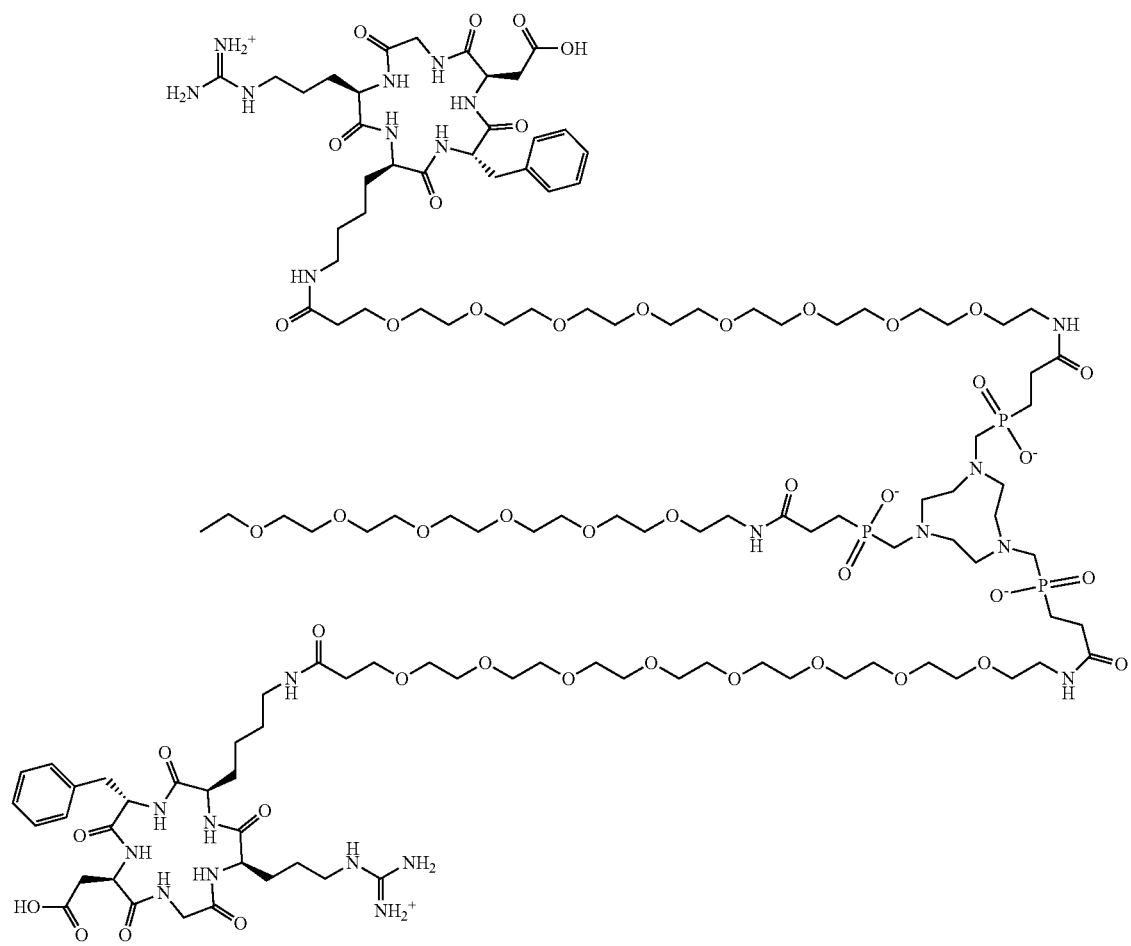

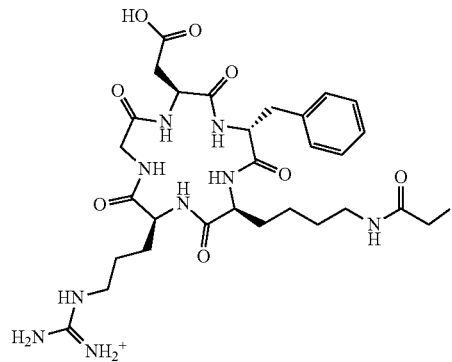
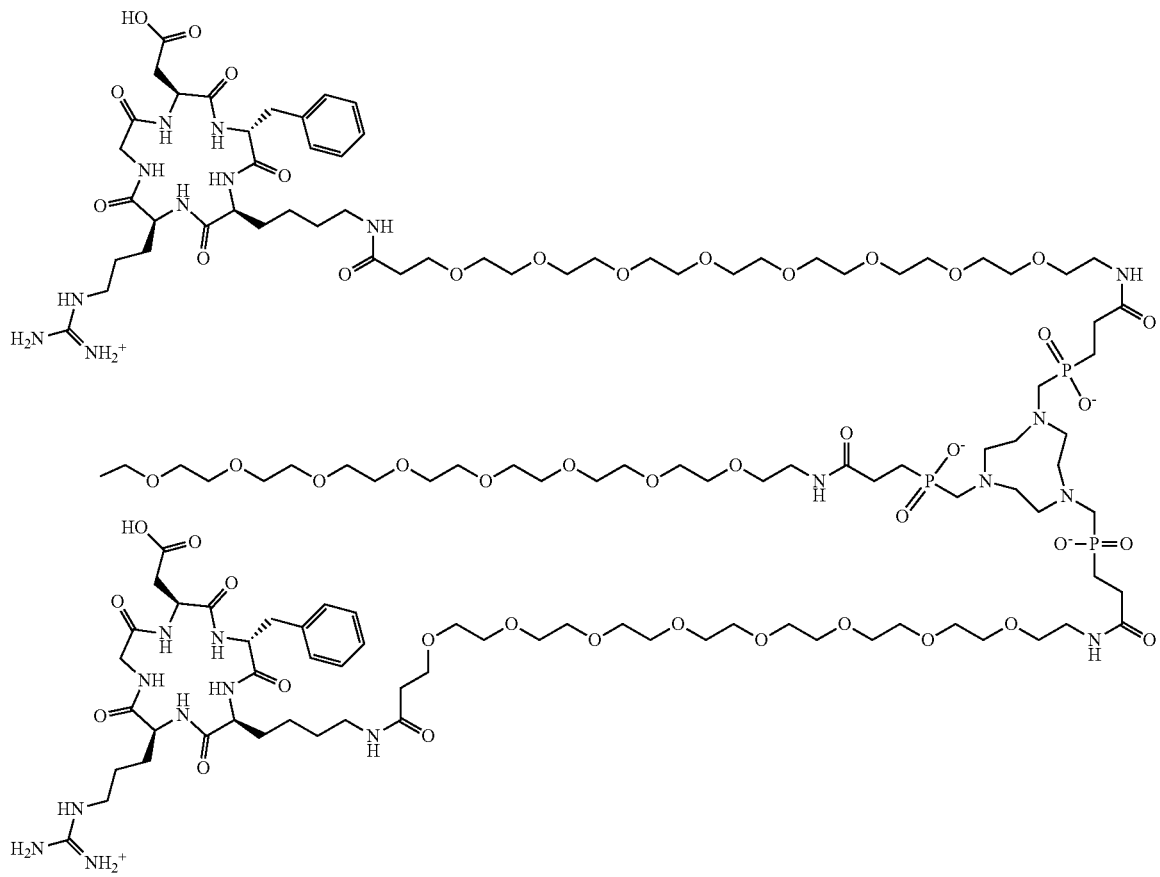
R3PEG8P9
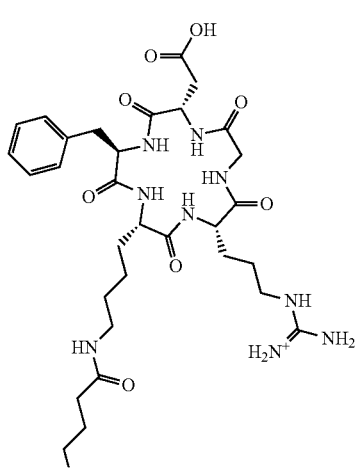
R3N3P9

-continued

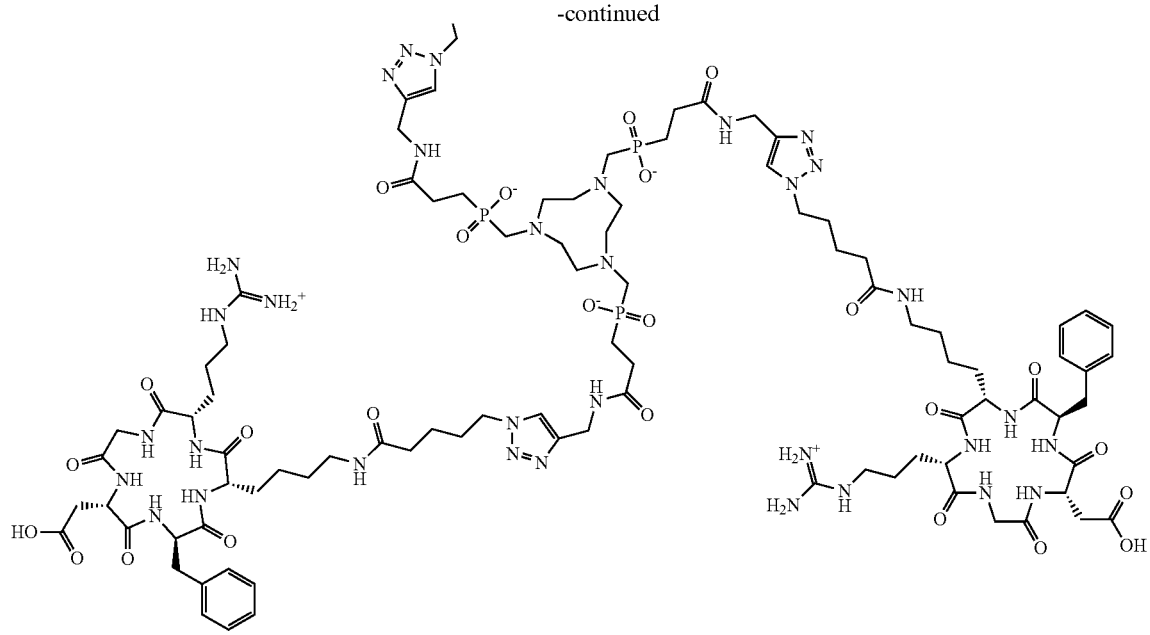

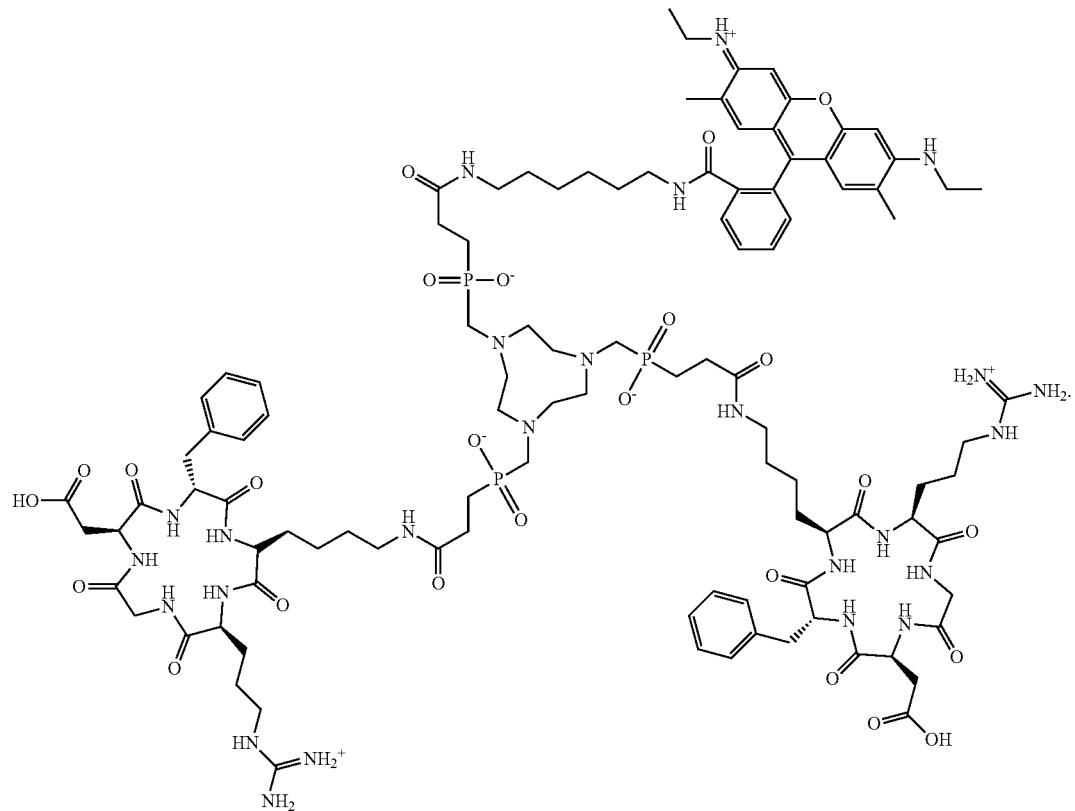

2. A chelate comprising at least one chelate ligand as defined in claim 1 and at least one metal or radiometal.

3. The chelate according to claim 2, wherein the at least one metal or radiometal is selected from the group consisting of $La^{3+}$, $Ce^{3+}$, $Pr^{3+}$, $Nd^{3+}$, $Sm^{3+}$, $Eu^{2+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, $Sc^{3+}$, $Y^{3'}$, $Al^{3+}$, $Ga^{3+}$, $Ge^{4+}$, $In^{3+}$, $As^{3+}$, $Sn^{2+}$, $Sn^{4+}$, $Sc^{3+}$, $Ti^{4+}$, $V^{5+}$, $Cr^{3+}$, $Mn^{2+}$, $Fe^{3+}$, $Co^{2+}$, $Co^{3+}$, $Ni^{2+}$, $Cu^{1+}$, $Cu^{2+}$, $Zn^{2+}$, $Cd^{2+}$ and mixtures thereof.

4. The chelate according to claim 2 or 3, wherein the at least one radiometal is selected from the group consisting of $^{44}Sc$, $^{46}Sc$, $^{55}Co$, $^{99m}Tc$, $^{203}Pb$, $^{66}Ga$, $^{67}Ga$, $^{68}Ga$, $^{72}As$, $^{111}In$, $^{113m}In$, $^{114m}In$, $^{97}Ru$, $^{62}Cu$, $^{64}Cu$, $^{52}Fe$, $^{52m}Mn$, $^{51}Cr$, $^{186}Re$, $^{188}Re$, $^{77}As$, $^{90}Y$, $^{67}Cu$, $^{169}Er$, $^{117m}Sn$, $^{121}Sn$, $^{127}Te$, $^{142}Pr$, $^{143}Pr$, $^{198}Au$, $^{199}Au$, $^{149}Tb$, $^{161}Tb$, $^{109}Pd$, $^{165}Dy$, $^{149}Pm$, $^{51}Pm$, $^{153}Sm$, $^{157}Gd$, $^{166}Ho$, $^{172}Tm$, $^{169}Yb$, $^{175}Yb$, $^{177}Lu$, $^{105}Rh$, $^{111}Ag$ and mixtures thereof, preferably selected from the group consisting of $^{44}$Sc, $^{99m}$Tc, $^{67}$Ga, $^{68}$Ga, $^{111}$In, $^{64}$Cu, $^{188}$Re, $^{90}$Y, $^{177}$Lu and mixtures thereof.

5. A method of molecular imaging comprising administering a chelate ligand or chelate, according to either claim 2 or claim 3, to a patient and performing an imaging step.

6. The method according to claim 5, wherein said molecular imaging is multimodal molecular imaging of the distribution of said chelate ligand or chelate in said patient.

* * * * *